(12) United States Patent
da Costa e Silva et al.

(10) Patent No.: US 7,709,698 B2
(45) Date of Patent: May 4, 2010

(54) TRANSCRIPTION FACTOR STRESS-RELATED PROTEINS AND METHODS OF USE IN PLANTS

(75) Inventors: Oswaldo da Costa e Silva, Neustadt (DE); Nocha Van Thielen, Durham, NC (US); Ruoying Chen, Apex, NC (US); Hans Bohnert, Tucson, AZ (US)

(73) Assignee: BASF Plant Science GmbH (DE)

( * ) Notice: Subject to any disclaimer, the term of this patent is extended or adjusted under 35 U.S.C. 154(b) by 157 days.

(21) Appl. No.: 12/168,972

(22) Filed: Jul. 8, 2008

(65) Prior Publication Data

US 2008/0307543 A1    Dec. 11, 2008

Related U.S. Application Data

(60) Division of application No. 09/828,303, filed on Apr. 6, 2001, now Pat. No. 6,677,504, and a continuation of application No. 11/566,282, filed on Dec. 4, 2006, now Pat. No. 7,427,696, and a continuation of application No. 10/716,089, filed on Nov. 18, 2003, now Pat. No. 7,161,063, and a division of application No. 09/828, 303, filed on Apr. 6, 2001, now Pat. No. 6,677,504.

(60) Provisional application No. 60/196,001, filed on Apr. 7, 2000.

(51) Int. Cl.
*C12N 15/82* (2006.01)
*C12N 15/29* (2006.01)
*A01H 5/00* (2006.01)
*A01H 5/10* (2006.01)

(52) U.S. Cl. ............... 800/289; 435/419; 435/468; 800/298; 536/23.6

(58) Field of Classification Search ............... None
See application file for complete search history.

(56) References Cited

U.S. PATENT DOCUMENTS 5,929,305 A * 7/1999 Thomashow et al. ........ 800/295

* cited by examiner

*Primary Examiner*—Cynthia Collins
(74) *Attorney, Agent, or Firm*—Patricia A. McDaniels

(57) ABSTRACT

A transgenic plant transformed by a Transcription Factor Stress-Related Protein (TFSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated TFSRPs, and isolated nucleic acid coding TFSRPs, and vectors and host cells containing the latter.

21 Claims, 12 Drawing Sheets

LB OCS3 NPTII  AtAct2-i  Super promoter  "Gene of Interest"  NOSpA  RB

Figure 2
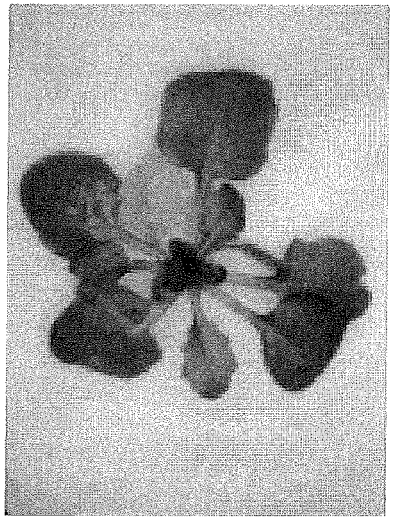
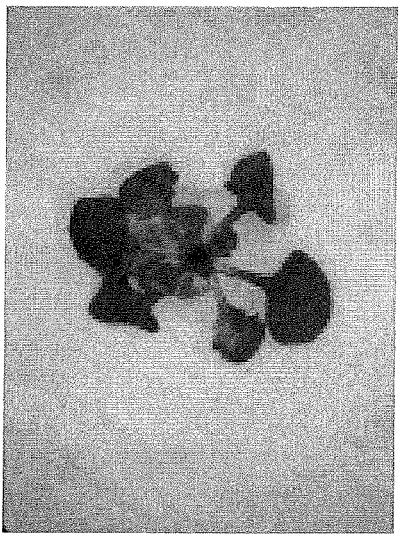
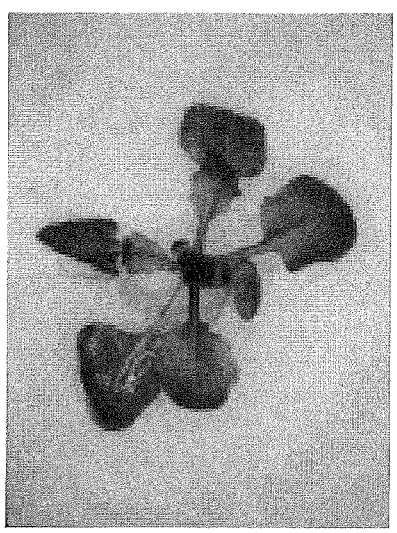
PpZF-2
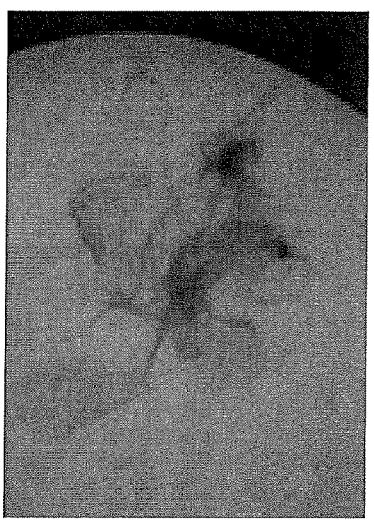
Wild Type

Figure 3
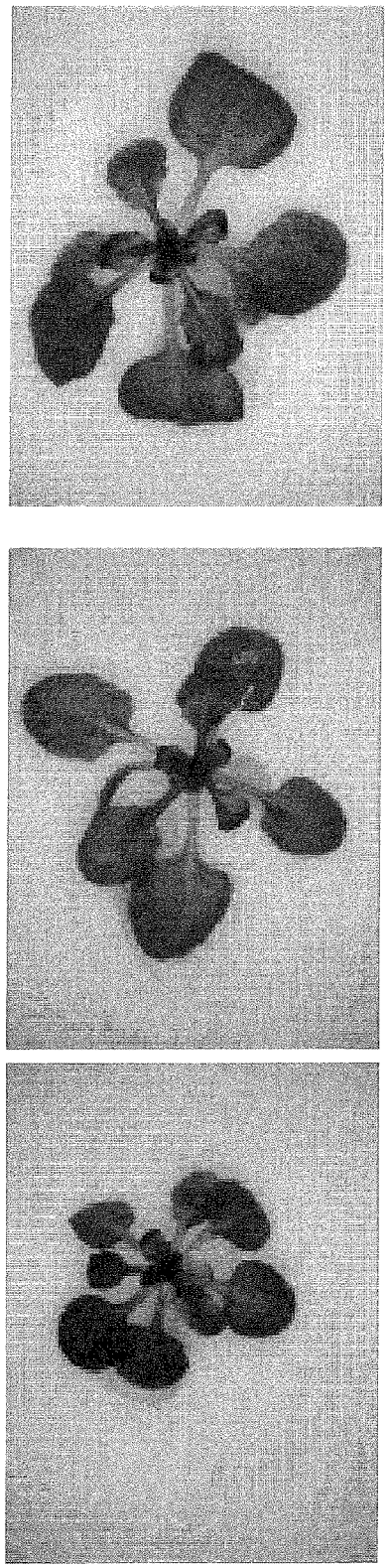
PpZF-3
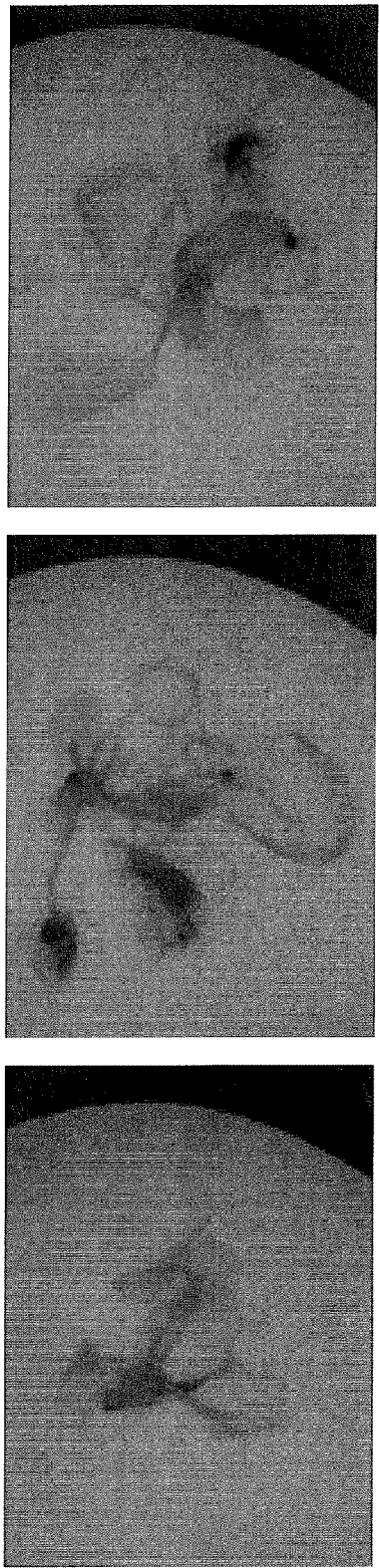
Wild Type

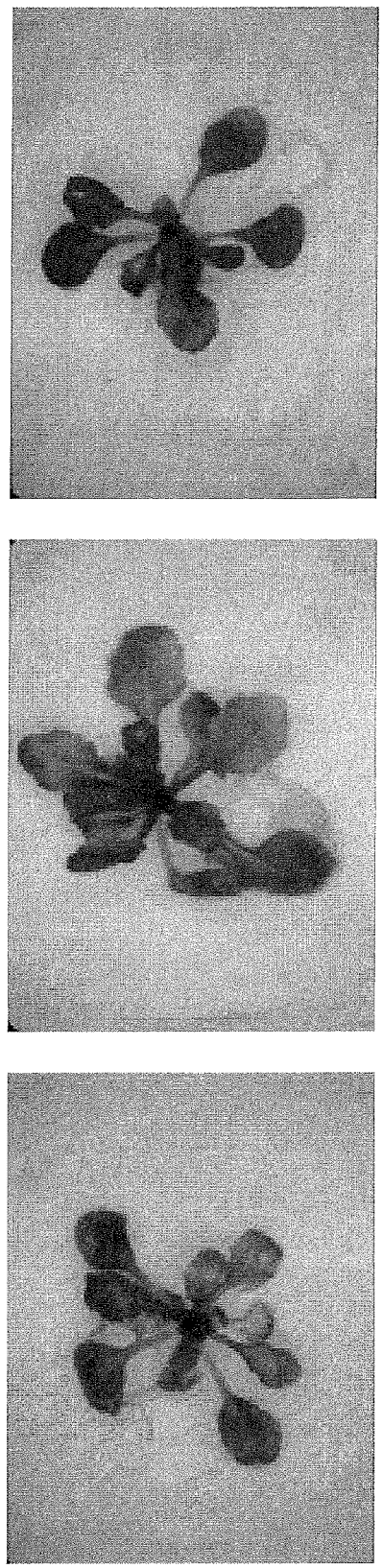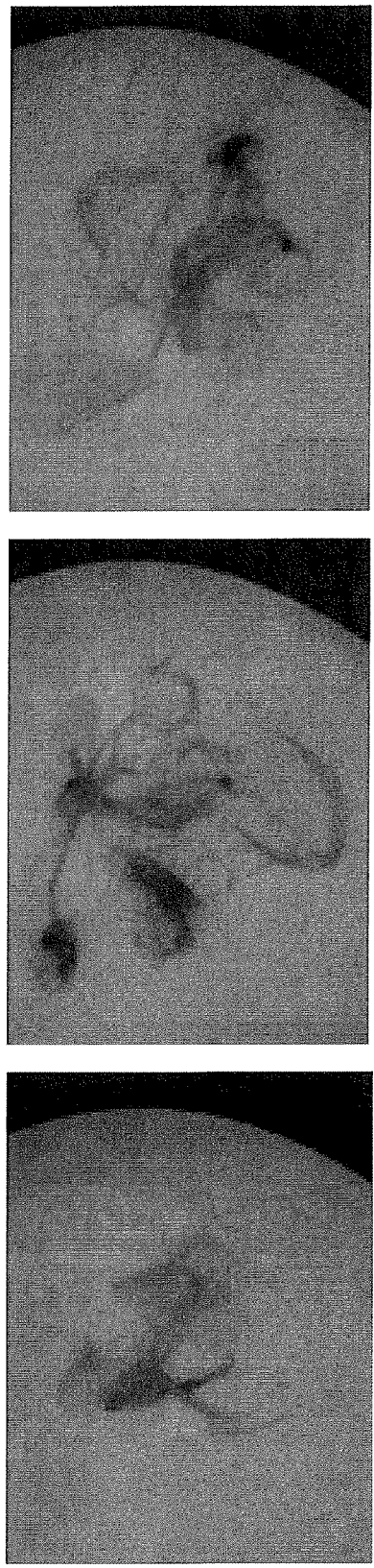
Figure 4  PpZF-4  Wild Type

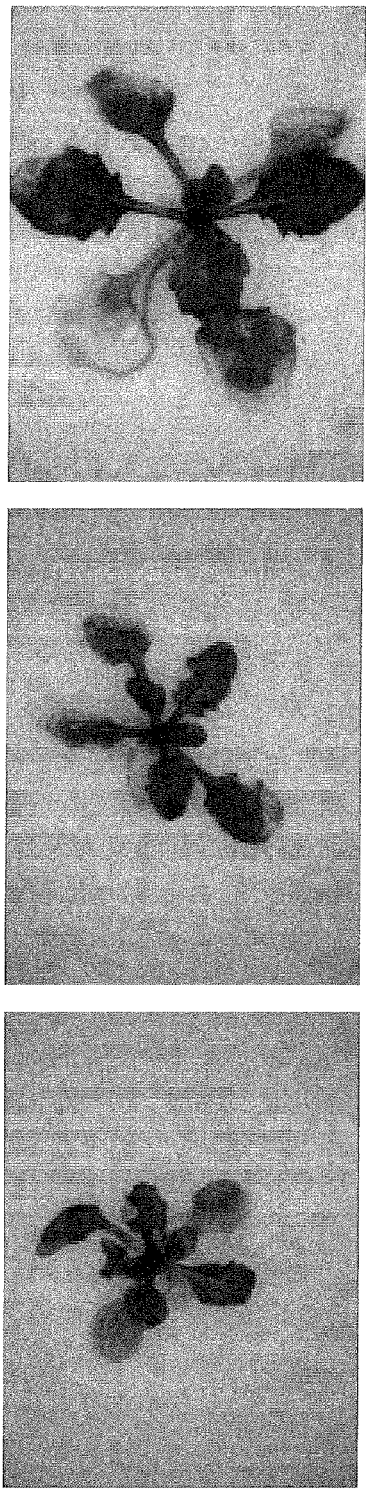
Figure 5 — PpZF-5 | Wild Type

Figure 6
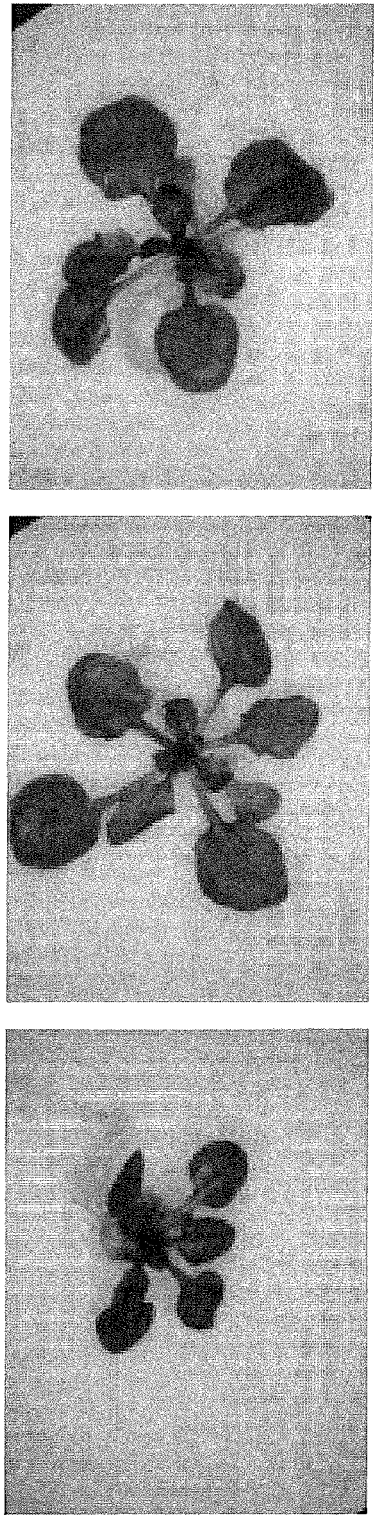 
PpCABF-3 | Wild Type

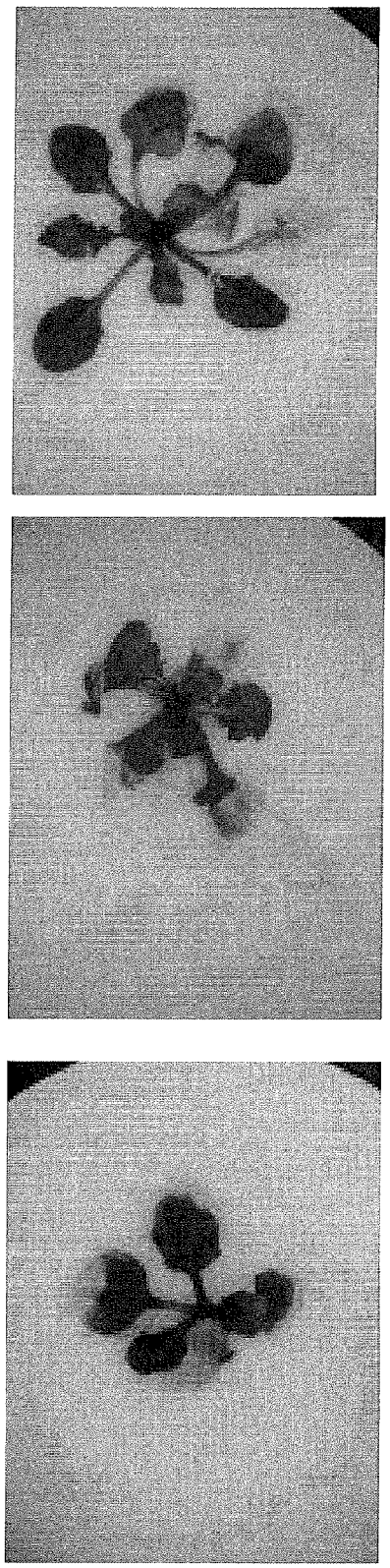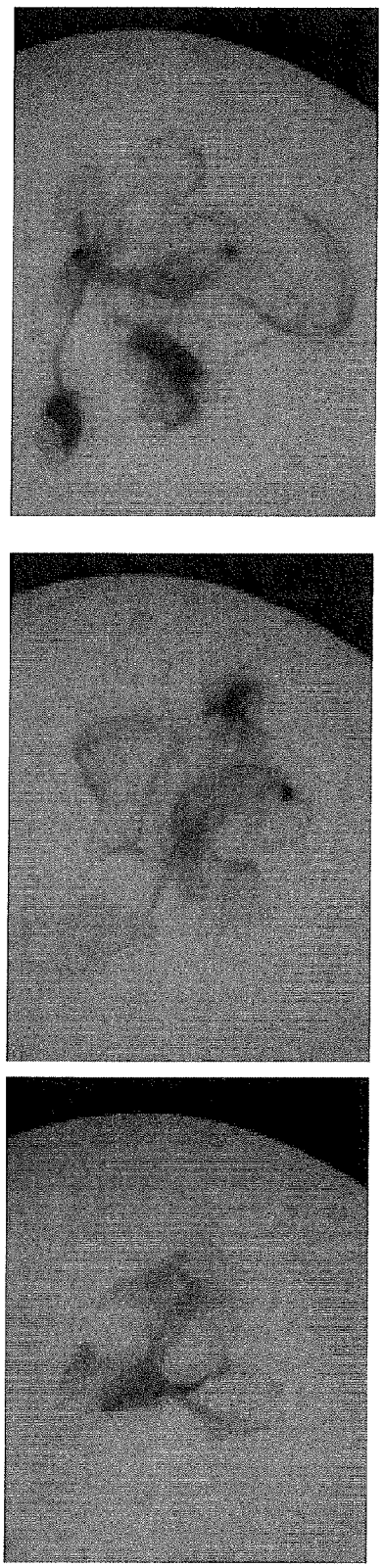
Figure 7

Figure 9
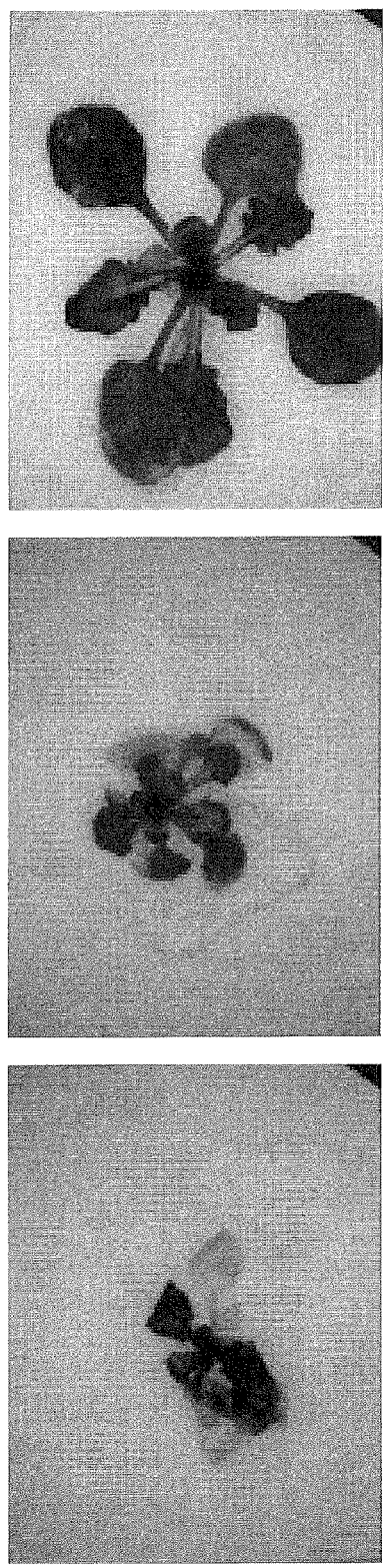
PpMYB-1
Wild Type

Figure 10
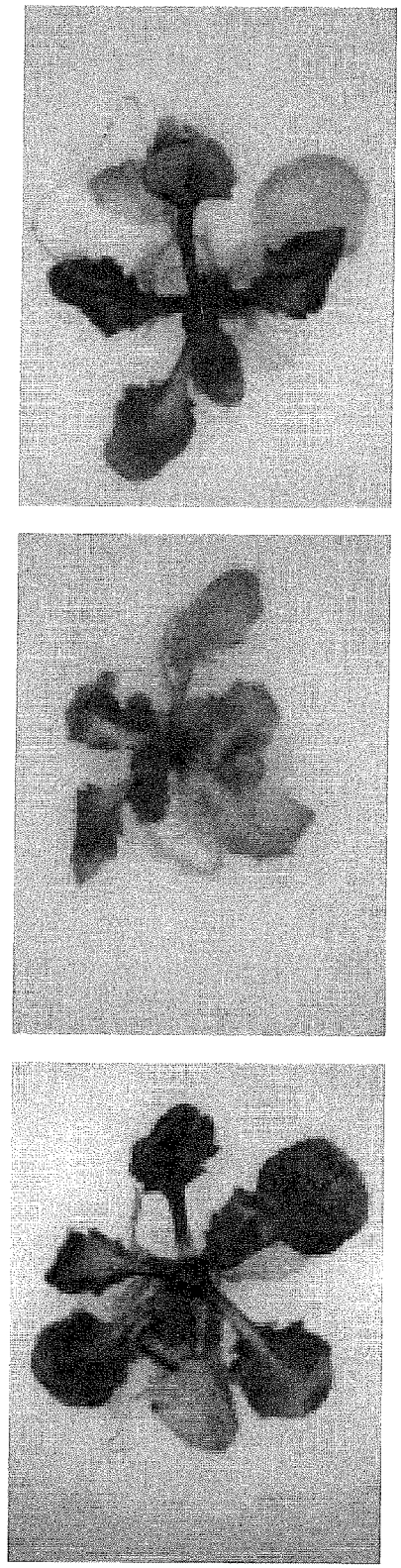 PpCABF-3
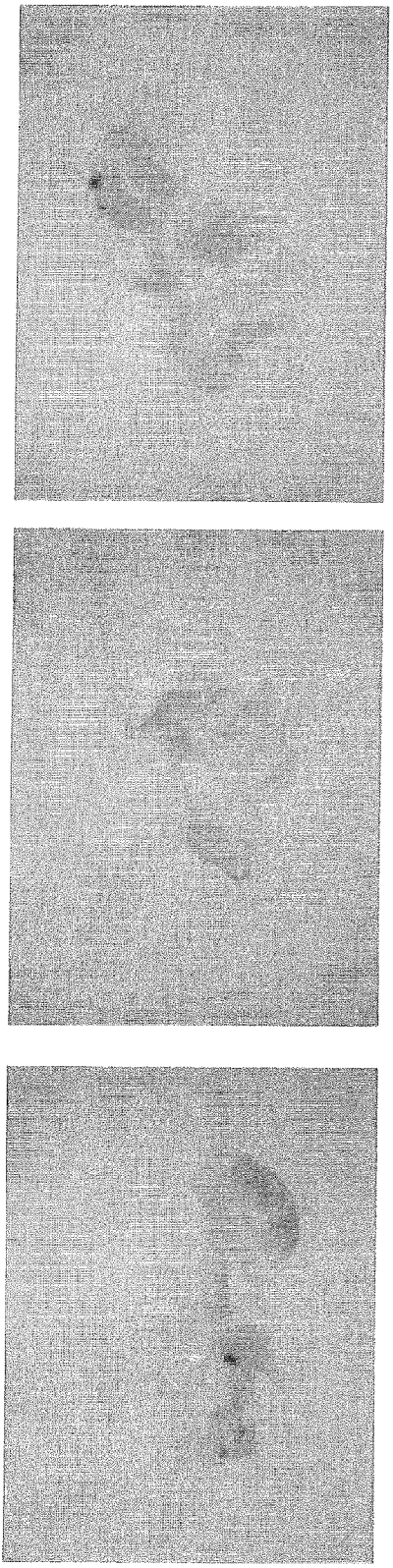 Wild Type

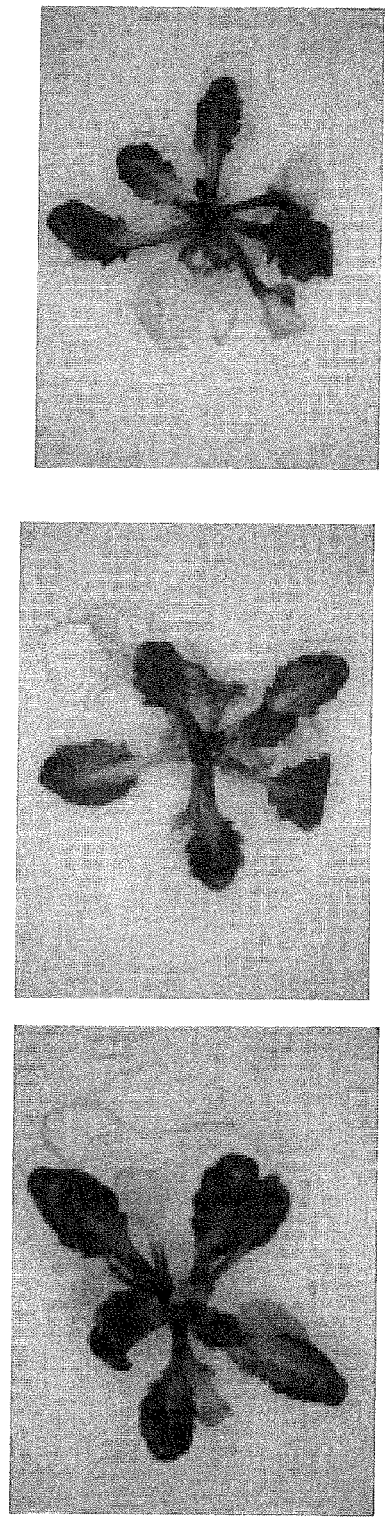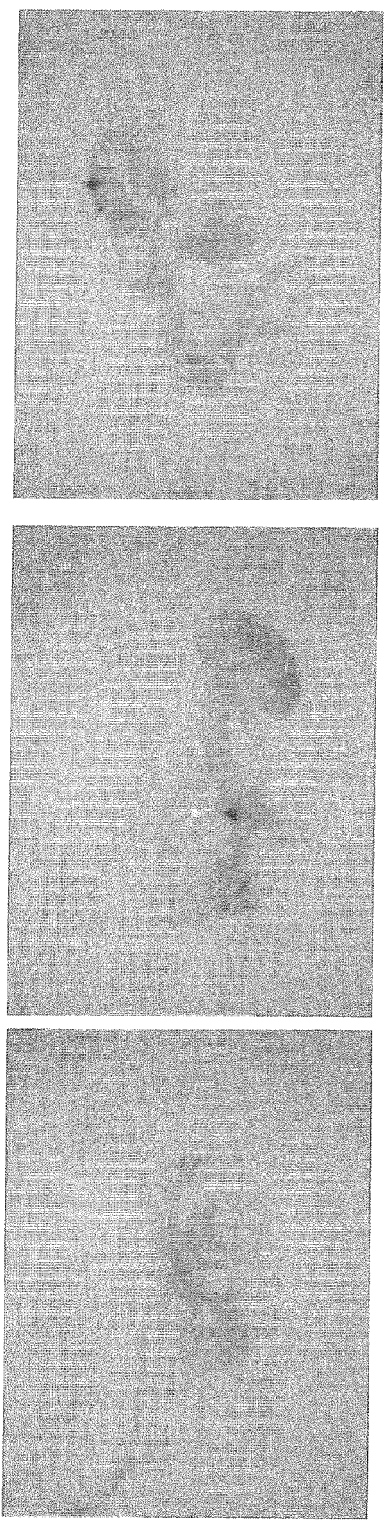
Figure 11
PpZF-2
Wild Type

Figure 12
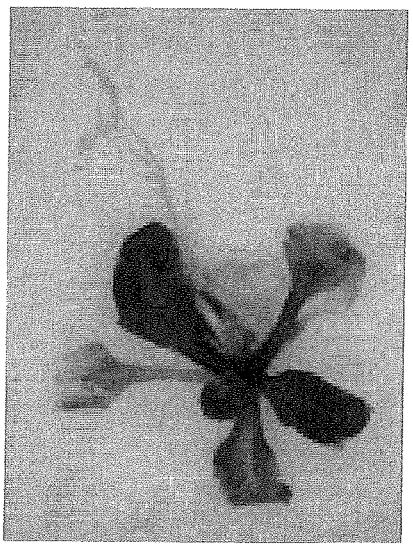
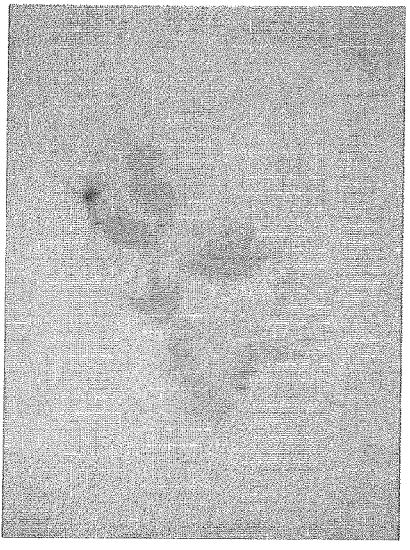
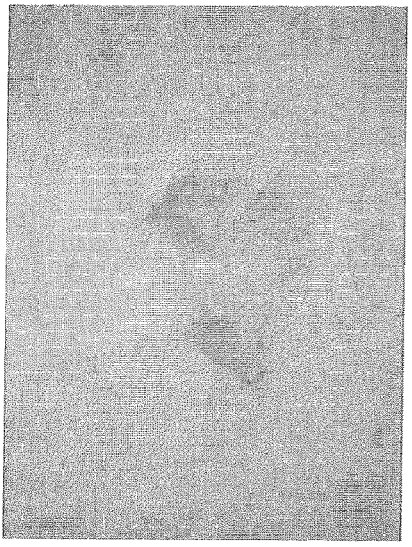
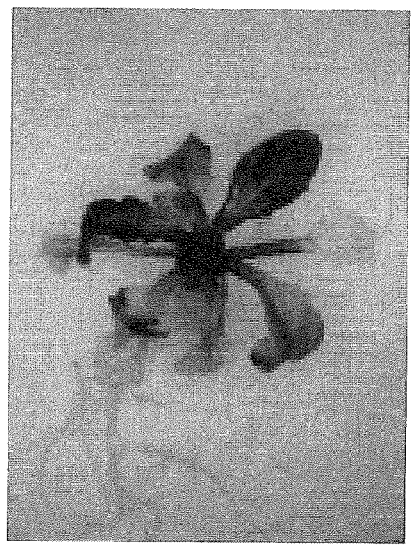
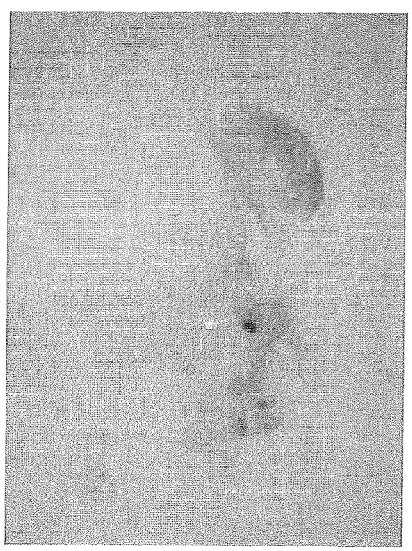
PpZF-3 | Wild Type

SEQUENCE LISTING

<160> NUMBER OF SEQ ID NOS: 79

<210> SEQ ID NO 1
<211> LENGTH: 986
<212> TYPE: DNA
<213> ORGANISM: Physcomitrella patens

<400> SEQUENCE: 1
tcaagccact catccgagca tagaacatca caacccacct tgatgatcat tctctcagcc    60
gaccagcgtc aattacgctg cgtatcgctc tagcttgagg aaggcaccct cgccctcttc   120

```
gccgcggaag tagccctctg cttcacgagg gcggcaaaac tctcccaagg cagttccggg    180
gggatgggat atagctgcag ctgctgtggg gaatcctcaa aattgtacgg gatcttcttc    240
tttgtgtaga agatgccaac atcgtaggcc cgggcagctt cttccggagt ttcatatgtt    300
cccagccata tcttacgttt ctgagatgtg gtcgaattt ctgtcaccca tttgtttagc     360
tcgggccggt gccgaacccc cctaaaactg gtcgtatcgc cagtgttgct agcagaaact    420
tcttcggtat cccatgccga tggggcctta tttaaatcaa tattccgaaa tttaaaggca    480
ttccgaccgc tagtgtcttt cgccgctaac cgcattccct tggattcttc ttccaaacta    540
gattcagact tgctctcctg ccaacttctt ttttcacttt cggggattct attttagtcg    600
ttaactgcaa cgcctgttct ttgaccttgc caccacaagg atcccacttc tttgttttgg    660
gcttcccctg ttcaataatg ctggaaattg tcaaattcat gaactaccca attgcaaccc    720
ctcccaccgg gatggattga tcgccaaaat ttcgtagtaa cttaactttc atacaacaac    780
ttgagttcct tcgctattag ggacacgtgg cagaaacttg gacgtgcaag cgtatgtact    840
catcagagtt tgacagcgca taaaatcata taaaaagtct tgaagaagcg ttgtttaatt    900
catgggtaac cacgagttac gcggagcgtc ggcagcaagg agaggacgac caggcggcaa    960
gaagatgcgt cggcaagagc tcgtgc                                         986

<210> SEQ ID NO 2
<211> LENGTH: 1690
<212> TYPE: DNA
<213> ORGANISM: Physcomitrella patens

<400> SEQUENCE: 2 tttttttttgg cgaaaatggg taaaaatttc cgtggccgta aaatcagttg tggcgcttgc    60
cttgcaataa gctggttatc gtaaaatggc aattaccttg atatgttcac taggttcgtg   120
tcagtgagat gccttgcaga aggcgatttc ccgtttattt acaactctac atgttactga   180
agcactgtgg cattcaatct cctaacctag agatgcttaa ctgcttcgtg catgatctat   240
attacatctt gagcctcaga ctgtggcgtc ttattgcaca tctagcgcta tatattacac   300
tacggtacac catcggaaga agtgaagaag gaatagctac tattttgcat ctccagtgtc   360
aaatgtgatg ctgacctgac ctaatcggca gagacgcaga tctccaatgc tcacacttca   420
catcctaaaa cgcacttgca gtgtaccctg ctctcaattc ccattgcaat tccacatctg   480
ggatctaagg gcatgctttg tgggcactaa agccgcgatt tcctcctcaa tgcgaaggtt   540
gaccttactg aggaaagtgc gcatcgtaat cggcgatgta ggcttaggga tttcgccggg   600
taacactcaa cgcaatcgtg acgttcgcta gatagcttgg ttgatatcag gtgcaaatcc   660
cacaaaatcc tttgcatggt cgggcattta tgtctaccag ggaagtatca gtttctcttcc   720
agaataaaat ttccacttta acagcacctg ctcacgaaat cctcaggcat gtggtggtgg    780
tggacggggt gaagaagaag gccgccctc gtcaacacca tcttctccag tttggggcga    840
caccacactc ttccctcggc tcaacaaacg tcggaagctc gctgaagcac gcgccatcgg    900
cgacaaaaca ttcgacgaat tgctgacagc cgctggacca gacctcggaa tgtcgatagt    960
aacctgaaac ggcgcacgaa tactggacgc gccctcgct tctgcactcc ctcctgcacc   1020
tgcactgctc atctgcgcat gattcccca gaataacaca ttggacggga ttccggacgg   1080
tgtctcgtaa tcttttatgt tttgctgctg atcaaccgca acggccgttt ccgacgtacc   1140
acttcggcga tgattctccc cgccctgatc ctccgcagtg cggggcaaac tattgcctct   1200
```

-continued

| | |
|---|---|
| tggggaacta ttcaacgccg gcaactgtcc ccggctccgt tggctcctcc tggaagctcg | 1260 |
| catgccgcc atgaacggcg ctcctacgtc acccataacg ggcgcttcca tctgaggagg | 1320 |
| ctcgcttatc tgcatcacgg tggcggcctc ggtcttcttc tcagtttcat cagctcccac | 1380 |
| actcgtgcga cacaacgggc atgtcgagtg cgagtgcaac cacatgtcaa tacaatccaa | 1440 |
| gtggaaacta tggtcacact tcggcaacgt gcggcctttc tcacccaact caaattcttc | 1500 |
| caaacaaacc gcgcactcga acccacgctt tgccctctca ccgtcgaatt cgaaagtggg | 1560 |
| cagagcttca ataacagccc gctcaagccc cactgcctgc gtcaccggag tagcgttcac | 1620 |
| agggacagtg taacggcgtc ttcgccatga taacgtacgc aaggtgccat cgcttgcgac | 1680 |
| gatctggtgc | 1690 |

<210> SEQ ID NO 3
<211> LENGTH: 502
<212> TYPE: DNA
<213> ORGANISM: Physcomitrella patens

<400> SEQUENCE: 3

| | |
|---|---|
| gcaccagcgc ttttaaacaa tcaaatatct gagcaggttg atggcgaaga ttcagatgta | 60 |
| tcaagaagtg gcgctagtga tcaatctggg catgaaagac cccttgacgt tttacgcaag | 120 |
| gtgaaaggaa atgatgcttg tgccgactgc ggtgctgctg atcccgattg ggcttcgctg | 180 |
| aatcttggga ttcttctgtg tattgagtgc tcaggagtac acagaaacat gagcgttcag | 240 |
| atttctaagg tccgttcgtt gacgttagat gtcaaagttt gggagccttc tgtaatgagc | 300 |
| tattttcaat ctgtcggaaa ctcctacgct aattctatat gggaagagct tttgaatccc | 360 |
| aagtcctcag aggagtcaag tgagagaaac gttaatgacg agggacaatc gggcgtttta | 420 |
| agtgctagca gagcaaggcc aagacctaga gaccccatac ctatcaaaga aagatttatc | 480 |
| aatgcaaagt atgtggagaa aa | 502 |

<210> SEQ ID NO 4
<211> LENGTH: 1531
<212> TYPE: DNA
<213> ORGANISM: Physcomitrella patens

<400> SEQUENCE: 4

| | |
|---|---|
| gcacgagctg ccccattcga gcccactcgc acgagaagat acgagccgcg ctttggccga | 60 |
| gtggtcgtaa gtagaagtaa aggtccgcgg ccgctgcggt ctgtgaaatt ctctcgcacg | 120 |
| gagagaagcg tgttctgctg gtttcttcgc acagagactt ctcctgcacc tttttcttctt | 180 |
| cctctacatc gtctcctgcg acgactacat tgtgtgggag cagtggcaac cttcctggcc | 240 |
| accccgggct tcctctcagt cagtggctca cgtctcccag ctaggcctcc catcgcgtct | 300 |
| tgccggctca atcgggtgtc ttgctctgtt ttttaacctc tctcccttcc ggccctctta | 360 |
| ttcctctcca gtcacttccg ccggatcgcg acttttgtac ccatttgggg gttgggtgtt | 420 |
| ataagtttgc cctcagggtg tgagttgctt tgtgtgtctt ttgtagtagt actttgcttg | 480 |
| ttgggtgcgg aagggaacct ttgagaagtc gacccattct ctagttttgc accagtcccg | 540 |
| cttagtgtgt gtgtcattag tgttggttgc aagtctgaag ccttgagcga gatttgcagg | 600 |
| atttttctcat acgcttctga ttaggaaaga tacatcctta ttagtctgtt aaagatggcc | 660 |
| accgagcgtg tgtctcagga gacgacctcg caggcccctg agggtccagt tatgtgcaag | 720 |
| aaccttgcg gcttcttcgg cagccaagct accatggggt tgtgctcgaa gtgctaccga | 780 |
| gagacagtca tgcagcgaag atgacggctt tagctgagca agccactcag gctgctcagg | 840 |

| | |
|---|---|
| cgacatctgc cacagctgct gctgttcagc cccccgctcc tgtacatgag accaagctca | 900 |
| catgcgaggt tgagagaaca atgattgtgc cgcatcaatc ttccagctat caacaagacc | 960 |
| tggttacccc cgctgcagct gcccctcagg cagtgaagtc ctctatcgca gctccctcta | 1020 |
| gacccgagcc aatcgatgc ggatcttgca ggaagcgtgt tggattgaca ggatttaagt | 1080 |
| gtcgctgtgg caacctctac tgcgctttac atcggtactc ggacaaacac acttgcacat | 1140 |
| atgactacaa agccgcaggg caggaagcga ttgcgaaagc taatcctctt gtcgtggccg | 1200 |
| agaaggttgt caagttttga tgagcatccg ttaagctttt ctgccgacga tttaggcttc | 1260 |
| atacattgag taactctaca tctttcttct ttatcgagag agcgagtcgc atcaagatga | 1320 |
| agtcgagggg tgcgcgtcgg ttttggggag aggggatttc tttccccttt ccccccttgg | 1380 |
| cggcatcgtg ttttatgtgt acagaagtag gttaggacaa gatagaatca tatgccagat | 1440 |
| caattgatag tcctctttaa ggaggacact tattacacaa taaaaaatcc tgggtaatgc | 1500 |
| atgccttgat tgtgttgttt tttcctcgtg c | 1531 |

<210> SEQ ID NO 5
<211> LENGTH: 689
<212> TYPE: DNA
<213> ORGANISM: Physcomitrella patens

<400> SEQUENCE: 5

| | |
|---|---|
| gcgtggggcg tctacactag tttatccccg ggctgaggaa ttcggcacca gatttgtcaa | 60 |
| tcaaagaag ttagttgcgg gtgatgctat tgtatttctt cgcatcgcat ctggcgaact | 120 |
| ttgtgtcggc gtgcgccgtt caatgagggg tgtcagcaac ggagaatcct catcttggca | 180 |
| ctcctcaatc agtaatgctt caacgattcg gccatctcga tgggaggtga agggcacaga | 240 |
| aagtttctcg gacttttttag gtggcgttgg tgataatggg tacgcactga atagctcaat | 300 |
| tcggtctgaa aaccagggct ctccaacaac gagtagcttt gcacgggacc gtgctcgtgt | 360 |
| tactgcgaag tccgttctag aagctgctgc actcgccgtc tccggtgaac gttttgaggt | 420 |
| tgtgtattat cctcgtgcta gcacagctga gttctgtgtc aaagctgggc ttgttaaacg | 480 |
| tgcgctagag caatcgtggt acgctggaat gcgcttcaaa atggcatttg aaactgaaga | 540 |
| ctcctcgagg ataagctggt ttatgggaac tattgctgct gttcaagcag cagatccagt | 600 |
| aacttgtggc ctagttctcc atggcgggtc tgcaggtcac cttgggatga gcggacctat | 660 |
| tgcaggagtg atcgtgtagc catggagta | 689 |

<210> SEQ ID NO 6
<211> LENGTH: 506
<212> TYPE: DNA
<213> ORGANISM: Physcomitrella patens

<400> SEQUENCE: 6

| | |
|---|---|
| gcaccagtgt tccctttcat atgctcagca tgtccgccaa tgagcgcgcc tgttgtgtac | 60 |
| agtctgtgga gagctgtaga aaattcaatt ccgatttcaa aatatccagc gacgatgaca | 120 |
| cggaacatgg gagtttggag gacgacatga aggagttgaa cgaagacatg gaaattccct | 180 |
| taggtcgaga tggcgagggt atgcagtcaa agcagtgccc gcgcggccac tggcgtccag | 240 |
| cggaagacga caagctgcga gaactagtgt cccagtttgg acctcaaaac tggaatctca | 300 |
| tagcagagaa acttcagggt cgatcaggga aaagctgcag gctacggtgg ttcaatcagc | 360 |
| tggaccctcg catcaaccgg cacccattct cggaagaaga ggaagagcgg ctgcttatag | 420 |

| cacacaagcg ctacggcaac aagtgggcat tgatcgcgcg cctctttccg ggccgcacag | 480 |
| acaacgcggt gaagaatcac tggccc | 506 |

<210> SEQ ID NO 7
<211> LENGTH: 536
<212> TYPE: DNA
<213> ORGANISM: Physcomitrella patens

<400> SEQUENCE: 7

| gcaccaggtc ttcgactttg cttcagcacg cgcgcgttgt ggtcgatctc tcgctggagc | 60 |
| aacaggttgt cttgtcgctg ccattgctaa agccattctt acttctagca cttctcggag | 120 |
| gttattgatt tctcgcaaat tgctcttcca cctgccctct tcgtgaggg agttcgaagc | 180 |
| tgaaaagtaa tgagctgaag attaaggtct tttacgagtg aacagcgagc acacagctag | 240 |
| caactctttc ggagaatact ccaggcgaaa ttggtcggat ggccgatagc tacggtcaca | 300 |
| acgcaggttc accagagagc agcccgcatt ctgataacga gtccgggggt cattaccgag | 360 |
| accaggatgc ttctgtacgg gaacaggatc ggttcctgcc catcgcgaac gtgagccgaa | 420 |
| tcatgaagaa ggcgttgccg tctaatgcaa aaatttcgaa ggacgcgaaa gagactgtgc | 480 |
| aggagtgtgt gtccgagttc atcagcttca tcactggtga ggcgtcagat aagtgc | 536 |

<210> SEQ ID NO 8
<211> LENGTH: 599
<212> TYPE: DNA
<213> ORGANISM: Physcomitrella patens
<220> FEATURE:
<221> NAME/KEY: modified_base
<222> LOCATION: (463)
<223> OTHER INFORMATION: a, t, c, g, other or unknown

<400> SEQUENCE: 8

| gcacgagttt tcttgtgtca aagcagcaga agaaatccac ttctggtagt attcaaacat | 60 |
| aaaagaatgg aaacttatgt aacagtctac tttctgatcg aaacattacc aaatgccttt | 120 |
| ttcctggttt ggtaggtact atcaatcagc agcaattaaa tagcgtcaga tttcacatct | 180 |
| aagtactctc gtagaatgct gttccggctg ggttgcctca gcttgcgcat cgcttttgcc | 240 |
| tcaatttgtc ttatcctttc ccgagtaact ttaaagattt gacctatttc ttctaaagtc | 300 |
| ttggaccgcc catcgtccaa tccaaaacgc agtcttagca cctccctctc tcttgggttc | 360 |
| aatgtgcgta gaacgccctc tatatcttgt cgcatcaatt gctttacgat tgcgtcctca | 420 |
| ggtgaatcca catctgtgtc tgcgacaagt tccccaagtg tantgtcccc atctttgcca | 480 |
| atgggccgct ccatcgaacc tggtgccttt gctgatttca ctacagattt cagtttctca | 540 |
| acagtcaagc ccactagctc agccacttcc tcgttacgtg cttcccgccc atgctcctg | 599 |

<210> SEQ ID NO 9
<211> LENGTH: 1057
<212> TYPE: DNA
<213> ORGANISM: Physcomitrella patens

<400> SEQUENCE: 9

| gcgatatcgg aagaagaacc aagggaatgc ggttagcggc gaaagacact agcggtcgga | 60 |
| atgcctttaa atttcggaat attgatttaa ataaggcccc atcggcatgg gataccgaag | 120 |
| aagtttctgc tagcaacact ggcgatacga ccagttttag gggggttcgg caccggcccg | 180 |
| agctaaacaa atgggtgaca gaaattcgac ccacatctca gaaacgtaag atatggctgg | 240 |
| gaacatatga aactccggaa gaagctgccc gggcctacga tgttggcatc ttctacacaa | 300 |

```
agaagaagat cccgtacaat tttgaggatt ccccacagca gctgcagcta tatcccatcc    360
ccccggaact gccttgggag agttttgccg ccctcgtgaa gcagagggct acttccgcgg    420
cgaagagggc gagggtgcct tcctcaagct agagcgatac gcagcgtaat tgacgctggt    480
cggctgagag aatgatcatc aaggtgggtt gtgatgttct atgctcggat gagtggcttg    540
aagggttctg gttccaacca tgagagcatg acgcgagtcc cacacggatg gagcttgtga    600
atggagtggt agactgtaga tggttttgt aacggcttga gtaataacgg aagcttcatg    660
gcttgaatga ccagccatgg tggtgtgcaa gtgaagatcg ctgcttgtgt gaaggtttcc    720
atctttccca tccccgtctt ccactttgct acacgttgct agtgtcactt gaacaattca    780
ttcatggacc ctgctctcct ttccctgtt acgaagttct tatggtagag ttcaccgaac    840
gcaagctgtc taggaagttg acagtttgtg ggagccaaaa actctacttg agctactgtg    900
tgcacgcctt ctgagtcctc cagcgaggag cctgtatatt attggatggt gcaggatggg    960
tcgcttggtg ccttctctct tttccttttc ctcttttgt aaatggtttt ccttctatga   1020
atatgtgaag ctcctcccac ggaagcatag agctcgc                           1057

<210> SEQ ID NO 10
<211> LENGTH: 1839
<212> TYPE: DNA
<213> ORGANISM: Physcomitrella patens

<400> SEQUENCE: 10
atcccgggat caggaagctg tcaaggaaga gatggaaatc ttgctccata caattactac     60
gggccgccac cgggcagtaa caattatgtc gtcaacagca agattatggt cgtggctgtc    120
gcggttctct tcgctgtcgt cctcttcatc ctctgcctcc acatctacgc caagtggttc    180
tggcgcaatc aaggtgccat cgtcgcaagc gatggcacct gcgtacgtt atcatggcga    240 agacgccgtt acactgtccc tgtgaacgct actccggtga cgcaggcagt ggggcttgag    300
cgggctgtta ttgaagctct gcccactttc gaattcgacg gtgagagggc aaagcgtgtg    360
ttcgagtgcg cggtttgttt ggaagaattt gagttgggtg agaaaggccg cacgttgccg    420
aagtgtgacc atagtttcca cttggattgt attgacatgt ggttgcactc gcactcgaca    480
tgcccgttgt gtcgcacgag tgtgggagct gatgaaactg agaagaagac cgaggccgcc    540
accgtgatgc agataagcga gcctcctcag atggaagcgc ccgttatggg tgacgtagga    600
gcgccgttca tggcggccat gcgagcttcc aggaggagcc aacggagccg ggacagttg    660 ccggcgttga atagttcccc aagaggcaat agtttgcccc gcactgcgga ggatcagggc    720
ggggagaatc atcgccgaag tggtacgtcg gaaacggccg ttgcggttga tcagcagcaa    780
aacataaaag attacgagac accgtccgga atcccgtcca atgtgttatt ctgggggaat    840
catgcgcaga tgagcagtgc aggtgcagga gggagtgcag aagcgagggc ggcgtccagt    900
attcgtgcgc cgtttcaggt tactatcgac attccgaggt ctggtccagc ggctgtcagc    960
aattcgtcga atgttttgtc gccgatgcg cgtgcttcag cgagcttccg acgtttgttg   1020
agccgaggga agagtgtggt gtcgccccaa actggagaag atggtgttga cgagggcggg   1080
ccttcttctt cacccgtcc accaccacca catgcctgag gatttcgtga gcaggtgctg   1140
ttaaagtgga aattttattc tggaagaaaa ctgatacttc cctggtagac ataaatgccc   1200
gaccatgcaa aggattttgt gggatttgca cctgatatca accaagctat ctagcgaacg   1260
tcacgattgc gttgagtgtt acccggcgaa atccctaagc ctacatcgcc gattacgatg   1320
```

| | |
|---|---:|
| cgcactttcc tcagtaaggt caaccttcgc attgaggagg aaatcggcgc tttagtgccc | 1380 |
| acaaagcatg cccttagatc ccagatgtgg aattgcaatg ggaattgaga gcagggtaca | 1440 |
| ctgcaagtgc gttttaggat gtgaagtgtg agcattggag atctgcgtct ctgccgatta | 1500 |
| ggtcaggtca gcatcacatt tgacactgga gatgcaaaat agtagctatt ccttcttcac | 1560 |
| ttcttccgat ggtgtaccgt agtgtaatat atagcgctag atgtgcaata agacgccaca | 1620 |
| gtctgaggct caagatgtaa tatagatcat gcacgaagca gttaagcatc tctaggttag | 1680 |
| gagattgaat gccacagtgc ttcagtaaca tgtagagttg taaataaacg ggaaatcgcc | 1740 |
| ttctgcaagg catctcactg acacgaacct agtgaacata tcaaggtaat tgccatttta | 1800 |
| cgataaccag cttattgcaa ggcaagcgcc agagctcgc | 1839 |

<210> SEQ ID NO 11
<211> LENGTH: 2041
<212> TYPE: DNA
<213> ORGANISM: Physcomitrella patens

<400> SEQUENCE: 11

| | |
|---|---:|
| atcccgggag gaggacttgc ggaatgcaaa atcacaattt gagcaggctc gattcaattt | 60 |
| gatgacagca cttaccaata gtgaggcaaa aaagaagttc gagttccttg aagccgtgag | 120 |
| tggtacaatg gatgcacatc tcaggtactt caagcagggc tatgagttgc tacatcaaat | 180 |
| ggaaccttac atccatcagg tgttaacata tgctcaacag tccagagaaa gggccaacta | 240 |
| cgagcaagca gcacttgcag atcgtatgca ggagtacagg caggaagttg agagagagag | 300 |
| ccaaaggtcg attgattttg acagctcttc tggagatggt attcaaggtg ttggccgcag | 360 |
| ttcacataag atgattgagg cagtcatgca atcgacccca aaagggcaga tccagactct | 420 |
| taagcaggga tacctgttaa agcgttcaac aaatttgcga ggtgactgga gcggaggtt | 480 |
| ttttgtgttg gatagcagag gaatgctgta ttattatcgg aaacagtggg gcaagcctac | 540 |
| agacgagaaa aatgtagcac atcacactgt gaatctgctg acgtctacaa tcaagataga | 600 |
| cgcagaacaa tcgatctctc gtttctgctt tcggattatt tctccagcta aaagttatac | 660 |
| cctccaggca gaaaatgcca ttgacagaat ggattggatg acaaaaatta cagggtgat | 720 |
| ttcgtcgctt ttaaacaatc aaatatctga gcaggttgat ggcgaagatt cagatgtatc | 780 |
| aagaagtggc gctagtgatc aatctgggca tgaaagaccc cttgacgttt tacgcaaggt | 840 |
| gaaaggaaat gatgcttgtg ccgactgcgg tgctgctgat cccgattggg cttcgctgaa | 900 |
| tcttgggatt cttctgtgta ttgagtgctc aggagtacac agaaacatga gcgttcagat | 960 |
| ttctaaggtc cgttcgttga cgttagatgt caaagtttgg gagccttctg taatgagcta | 1020 |
| ttttcaatct gtcggaaact cctacgctaa ttctatatgg gaagagcttt tgaatcccaa | 1080 |
| gtcctcagag gagtcaagtg agagaaacgt taatgacgag ggacaatcgg gcgttttaag | 1140 |
| tgctagcaga gcaaggccaa gacctagaga ccccatacct atcaaagaaa gatttatcaa | 1200 |
| tgcaaagtat gtggagaaaa aatttgtcca aaagttgaag gtggattctc gaggcccgtc | 1260 |
| agtgacacgg cagatctggg atgctgtcca gaacaaaaaa gtgcagcttg ctcttcgtct | 1320 |
| tcttatcact gctgatgcta acgccaacac aaccttcgag caagtaatgg gtggtaccga | 1380 |
| gtcttcgtgt tcgtctccac ttgcaagcct cgctggagct ctcttacgaa agaactctct | 1440 |
| cagtgcctct cagagtggtc gcaggaactg gagcgtacct tcactattgt cttctccaga | 1500 |
| cgatccgggg tcccgttcag gagctttaag ccctgtttcg agaagtcctg atgcagcagg | 1560 |
| cagcggaggg attgatgaga aagatttgcg gggctgcagt ttgctccatg ttgcctgcca | 1620 |

```
aatcggagat attagcctga tcgagctgct acttcaatac ggggcgcaaa tcaattgtgt    1680
ggatacccty ggtcgaactc ctcttcatca ctgtgtcttg tgcggcaaca attcgtgtgc    1740
aaagctcctg ctcacaagag gggcgaaggc gggtgccgta gacaaagagg gaaaaactcc    1800
gctggagtgt gcagtggaga agctaggtgc tatcacggat gaagaattgt tcataatgct    1860
ttctgaaacc agtagatgac accacatttg tgcctgagtt gctttgtgta taaatctcaa    1920
catcaacttg tttcctagca cctgtaaggc tagtttgttt gggtagtttg cattcttgtt    1980
ctaccgtttt atcttcccat tacgtcagca taagtagaga gtggaagcag gtggatatcg    2040
c                                                                   2041

<210> SEQ ID NO 12
<211> LENGTH: 804
<212> TYPE: DNA
<213> ORGANISM: Physcomitrella patens

<400> SEQUENCE: 12
atcccgggca ccagtcccgc ttagtgtgtg tgtcattagt gttggttgca agtctgaagc      60
cttgagcgag atttgcagga ttttctcata cgcttctgat taggaaagat acacccttat     120
tagtctgtta aagatggcca ccgagcgtgt gtctcaggag acgacctcgc aggcccctga     180
gggtccagtt atgtgcaaga acctttgcgg cttcttcggc agccaagcta ccatggggtt     240
gtgctcgaag tgctaccgag agacagtcat gcaagcgaag atgacggctt tagctgagca     300
agccactcag gctgctcagg cgacatctgc cacagctgct gctgttcagc cccccgctcc     360
tgtacatgag accaagctca catgcgaggt tgagagaaca atgattgtgc cgcatcaatc     420
ttccagctat caacaagacc tggttacccc cgctgcagct gcccctcagg cagtgaagtc     480
ctctatcgca gctccctcta gacccgagcc caatcgatgc ggatcttgca ggaagcgtgt     540
tggattgaca ggatttaagt gtcgctgtgg caacctctac tgcgctttac atcggtactc     600
ggacaaacac acttgcacat atgactacaa agccgcaggg caggaagcga ttgcgaaagc     660
taatcctctt gtcgtggccg agaaggttgt caagttttga tgagcatccg ttaagctttt     720
ctgccgacga tttaggcttc atacattgag taactctaca tctttcttct ttatcgagag     780
agcgagtcgc atcaagagct cgcc                                           804

<210> SEQ ID NO 13
<211> LENGTH: 2699
<212> TYPE: DNA
<213> ORGANISM: Physcomitrella patens

<400> SEQUENCE: 13
atcccgggta tcgatctgga gcccgttgca aactcaatgg tgtattttat agggcaaaag      60
tctgatctat atggaatgca tcctctcaga gttgcaaatc atggactgca tgtcactctg     120
ggttattctc gatcacctag ctttgctgga gttcaaattg gtgagtacga gtattatgag     180
tgatctcgag tttatggtcc ccttctttca tgatcaaggg taatttatat caagggtgta     240
tatgagagat acgcacttat tgagtggacc ttttctcata ctgcatttac accctgtca      300 gttgcagcat cctggtttgg aatgcccggt ccagtccctc tattatccat gagtgtaaaa     360
tcggagagtc tcgatgacat tggaggtcac gagaaaaaat ctgtaactgg gtcggaagtg     420
ggtggcctcg atgctcagct gtggcatgcc tgtgctgggg gtatggttca actgcctcat     480
gtgggtgcta aggttgtcta ttttcccaa ggccatggca acaagctgc ttcaactccc       540
```

```
gagttccccc gcactttggt tccaaatgga agtgttccct gccgagttgt gtcagttaac    600
tttctggctg atacagaaac agacgaggta tttgctcgta tttgcctgca gcctgagatt    660
ggctcctccg ctcaggattt aacagatgat tctcttgcgt ctccgcctct agagaaacca    720
gcttcatttg ccaaaacgct cactcaaagt gatgcaaaca acggtggagg cttttcaata    780
cctcgttatt gtgctgaaac tattttccca cctctcgatt actgtatcga tcctcctgtt    840
caaactgttc ttgcaaaaga tgtccatgga gaggtgtgga aatttcgtca catttacagg    900
gggactccac gtcgacattt gttaaccaca ggatggagca catttgtcaa tcaaaagaag    960
ttagttgcgg gtgatgctat tgtatttctt cgcatcgcat ctggcgaact ttgtgtcggc    1020
gtgcgccgtt caatgagggg tgtcagcaac ggagaatcct catcttggca ctcctcaatc    1080
agtaatgctt caacgattcg gccatctcga tgggaggtga agggcacaga aagtttctcg    1140 gacttttttag gtggcgttgg tgataatggg tacgcactga atagctcaat tcggtctgaa    1200
aaccagggct ctccaacaac gagtagcttt gcacgggacc gtgctcgtgt tactgcgaag    1260
tccgttctag aagctgctgc actcgccgtc tccggtgaac gttttgaggt tgtgtattat    1320
cctcgtgcta gcacagctga gttctgtgtc aaagctgggc ttgttaaacg tgcgctagag    1380
caatcgtggt acgctggaat gcgcttcaaa atggcatttg aaactgaaga ctcctcgagg    1440
ataagctggt ttatgggaac tattgctgct gttcaagcag cagatccagt actttggcct    1500
agttctccat ggcgggttct gcaggtcact tgggatgagc cggacctatt gcagggagtg    1560
aatcgtgtaa gcccatggca gttagagctt gtggcgacac ttcctatgca gctgccccct    1620
gtctctcttc ccaaaaagaa actgcgcact gtccagcctc aagagcttcc acttcagccc    1680
cctggactgc taagcctgcc gttggcaggg actagcaact ttggtgggca cttggccacc    1740
ccctggggca gctctgttct tttggatgac gcctctgttg gcatgcaggg ggccaggcat    1800
gatcaattca acgggcttcc aactgtggat ttccgaaaata gtaactacaa acatcctcgg    1860
gagttttcta gggacaatca gtaccagatt caagatcatc aagtcttcca tcctagacct    1920
gtattaaatg agcccctgc gacaaacact ggcaactact tctctctttt acctagtctc    1980
cagcgacggc cagatatctc tcctagtatt cagcccttag ccttcatgtc tgcttctgga    2040
agctcacagc tggagacttc ttcaactaag acagcggcca cctcttttt cctatttggc    2100 caattcattg acccttcttg cacctccaaa cctcagcagc gttccacagt tattaataac    2160
gcttccgttg ctggggatgg taagcatcct ggcactaata actcatcctc ggataacaaa    2220
tcagaggaca aggacaattg tagggatgtt caacccattc tgaatgggat tgctgtaaga    2280
tctggatttc gagcagatat agccgcgaag aagtttcaac agagcgactc tgcacatccc    2340
acggaagcat cacgtggaag ccaagttagc agcttaccgt ggtggcaaac acaggacgct    2400
cacaaggatc aggaattcca tggagacagt cagacgcctc atactcctgc atctggtagc    2460
caatgaggct aaagcttgat catagctcat aaccctctca caggacgtaa tggggtgac    2520 aacatgctaa cagaattgca cggtaaagga aaactgtact aggcatgtta tatgggaatt    2580
cggatcgctt cttgcaatta aacacgctag cgccgtttgg tgccaatgtt attctggcat    2640
ttgttttgtt tcctttggaa acaaattgct atatttcaaa gtcctttgga ggagctcgc     2699
```

<210> SEQ ID NO 14
<211> LENGTH: 2367
<212> TYPE: DNA
<213> ORGANISM: Physcomitrella patens

<400> SEQUENCE: 14

```
atcccgggct gttgtgtaca gtctgtggag agctgtagaa aattcaattc cgatttcaaa    60
atatccagcg acgatgacac ggaacatggg agtttggagg acgacatgaa ggagttgaac   120
gaagacatgg aaattccctt aggtcgagat ggcgagggta tgcagtcaaa gcagtgcccg   180
cgcggccact ggcgtccagc ggaagacgac aagttgcgag aactagtgtc ccagtttgga   240
cctcaaaact ggaatctcat agcagagaaa cttcagggtc gatcagggaa aagctgcagg   300
ctacggtggt tcaatcagct ggaccctcgc atcaaccggc acccattctc ggaagaagag   360
gaagagcggc tgcttatagc acacaagcgc tacggcaaca agtgggcatt gatcgcgcgc   420
ctctttccgg gccgcacaga caacgcggtg aagaatcact ggcacgttgt gacggcaaga   480
cagtcccgtg aacggacacg aacttacggc cgtatcaaag gtccggtaca tcgaagaggc   540
aagggtaacc gtatcaatac ctccgcactt ggaaattacc atcacgattc gaagggagct   600
ctcacagcct ggattgagtc gaagtatgcg acagtcgagc agtctgcgga agggctcgct   660
aggtctcctt gtaccggcag aggctctcct cctctaccca ccggtttcag tataccgcag   720
atttccggcg gcgccttcca tcgaccgaca aacatgagta ctagtcctct tagcgatgtg   780
actatcgagt cgccaaagtt tagcaactcc gaaaatgcgc aaataataac cgcgcccgtc   840
ctgcaaaagc caatgggaga tcccaggtca gtatgcttgc cgaattcgac tgtttccgac   900
aagcagcaag tgctgcagag taattccatc gacggtcaga tctcctccgg gctccagaca   960
agcgcaatag tagcgcatga tgagaaatcg ggcgtcattt caatgaatca tcaagcaccg  1020
gatatgtcct gtgttggatt gaagtcaaat tttcagggga gtctccatcc tggcgctgtt  1080
agatcttctt ggaatcaatc ccttccccac tgttttggcc acagtaacaa gttggtggag  1140
gagtgcagga gttctacagg cgcatgcact gaacgctctg agattctgca agaacagcat  1200
tctagccttc agtttaaatg cagcactgcg tacaatactg gaagatatca acatgaaaac  1260
ctttgtgggc cagcattctc gcaacaagac acagcgaacg aggttgcgaa ttttctacg   1320
ttggcattct ccggcctagt gaagcatcgc caagagaggt tgtgcaaaga tagtggatct  1380
gctctcaagc tgggactatc atgggttaca tccgatagca ctcttgactt gagtgttgcc  1440
aaaatgtcag catcgcagcc agagcagtct gcgccggttg cattcattga ttttctaggc  1500
gtgggagcgg cctgaaggct gcggaaagat tttagcaaag ctttataac gttttttttg   1560
cacagggctg ttttagctt gtataccagt aggcacttct acttcttttt cttcttttct   1620
ttttcccctt ttcttctccc ccactttca ccatttccgc catagcagcc tttgaatcac   1680
gtaatggaac ctttggcggc ctgtatgagg cacttttgga ggcatccctg gacgaagaat  1740
ggatcaaacc gtactgcgga tgtcatgctt tgaagctgca atccgaattc agtagcatgc  1800
tgtggatgac tcaaaaggag tagctgcttt gtgaaactaa tactatacag cggattttga  1860
agacccaagt ttcatgtgga caagtctgaa aaacttatac gccacctcca tgggcttcta  1920
cgatgaatat gcgctttcgg cttacactgc ggctcttttt tgcatatata tatacttcca  1980
ttcaattta tttggaaatg ttttgaatct accttctcgt acaaaactgg gatcagaaat  2040
cttccaggtt gtgggtcgca agttaactct gcagattgtg gctgacactt gggcaatcgg  2100
caactttatc ttttttgtttt ttacgcttga acggacctca gctgtacaga cactcatcat  2160
gtacattcga tgccatctct ggctttcat ggaagttcag atatcggaaa ctgtgacaga  2220
gacagagaga gagagagaga gagagagaga gagattcttg atgcactgtg cgccgagttt  2280
gagactagtt tagaaagatt gatgaagcta gcagtaaatt gttggcctca tctgaaaggt  2340
```

```
acggccttta ctccgtgagc ccgggat                                          2367
```

<210> SEQ ID NO 15
<211> LENGTH: 787
<212> TYPE: DNA
<213> ORGANISM: Physcomitrella patens

<400> SEQUENCE: 15

```
atcccgggca gcgagcacac agctagcaac tctttcggag aatactccag gcgaaattgg        60
tcggatggcc gatagctacg gtcacaacgc aggttcacca gagagcagcc cgcattctga       120
taacgagtcc gggggtcatt accgagacca ggatgcttct gtacgggaac aggatcggtt       180
cctgcccatc gcgaacgtga gccgaatcat gaagaaggcg ttgccgtcta atgcaaaaat       240
ttcgaaggac gcgaaagaga ctgtgcagga gtgtgtgtcc gagttcatca gcttcatcac       300
tggtgaggcg tcagataagt gccagaggga aagagaaag acgatcaacg gtgacgactt        360
gctgtgggcc atgagtacac ttggtttcga agattacgtg gagcctctga aggtttacct       420
acacaaatac cgggagctag agggagagaa ggcttccacg gccaagggtg gtgaccagca       480
aggagggaaa aagggagtc aaggtgttat ggggtccatg ggtatgtcgg gcggaatgaa        540
cggtatgaac ggtacgatga acgggaatat gcatggacat ggaatcccgg tgtcgatgca       600
gatgctgcag cagtcgtacg gacagcaggc acctccaggg atgatgtatt ccctcatca       660
gatgatgccg caataccaga tgccaatgca gtctggtgga aaccagcctc gtggagtgta       720
ggaggttcca cggcgaggag aatttgaaat tggggagatt gtcaaccgcg tgagggagtg       780
agctcgc                                                                 787
```

<210> SEQ ID NO 16
<211> LENGTH: 1669
<212> TYPE: DNA
<213> ORGANISM: Physcomitrella patens

<400> SEQUENCE: 16

```
atcccgggct cggaaggact gtgcattgtc gagcgctgaa ggtggatgat gctttggtga        60
ccgagagcgg tcttatcagt gaagaaggag tttctcgtgc tgcagctgag gaggcgatga       120
cgttagcttt agcagctgca aaggccgcca tggaggctgc ctcgtacgct gatgcgatgc       180
cgtggaacag gaggagtttc cgacggaatt tgatctgctg agactagaga gggccaggtt       240
gagcgatgtt gagcattctt ttcggggttga attggataca gaggctgcca tgatggaggc       300
cgagcagagt tatgtgcaga agctagaatc gttgttggga ggtgtttcca cgctcgtccg       360
tgaggaagag gaaactgcat ccgttttcaga agatgaagat gattcaaaca gcttacctca       420
aattcaagta gccgttaaat cgaagcgaa gggagagagg aggaagaggc gggagcgagc        480
gttggaaagg gcagagaagg ttgccaccga tcttgcatca gcaccccctc tcccaaaacc       540
taagaaacca cagcttgcgg cggatccttc agacccagtc cgtgcatatt gcgagacat        600
aggaaggacg aagttgctaa cagcaagaga agaagtcgat ctctctcatc aaattcagga       660
tcttttgaag ttggagaata tcaagtctaa ccttgagcga gagataggaa ggaatgccac       720
aattggagag tggagtagag cggtaggaat ggaacagaat gcatttgaag cgcggcttaa       780
gaagggtcga ttcgccaagg acaaaatggt gaattcgaat ttgcggttgg ttgtctcgat       840
tgcgaaaaac taccagggcc gaggcatgac tcttcaagat ttaattcagg aagggagcat       900
gggattggtg agaggagcgg agaagttcga cccgaccaag gggtttaagt tcagcactta       960
cgcacattgg tggattaggc aggctgtaac gcgatcaatt gcggatcaat ctaggacttt      1020
```

-continued

```
tcgtttacct attcatttat acgaagttat ctcacgtatc aacaaagcaa agcgaatgct    1080
ggttcaggag catgggcggg aagcacgtaa cgaggaagtg gctgagctag tgggcttgac    1140
tgttgagaaa ctgaaatctg tagtgaaatc agcaaaggca ccaggttcga tggagcggcc    1200
cattggcaaa gatggggaca ctacacttgg gaacttgtc gcagacacag atgtggattc     1260
acctgaggac gcaatcgtaa agcaattgat gcgacaagat atagagggcg ttctacgcac    1320
attgaaccca agagagaggg aggtgctaag actgcgtttt ggattggacg atgggcggtc    1380
caagacttta aagaaatag gtcaaatctt taaagctact cgggaaagga taagacaaat     1440
tgaggcaaaa gcgatgcgca agctgaggca acccagccgg aacagcattc tacgagagta    1500
cttagatgtg aaatctgacg ctatttaatt gctgctgatt gatagtacct accaaaccag    1560
gaaaaaggca tttggtaatg tttcgatcag aaagtagact gttacataag tttccattct    1620
tttatgtttg aatactacca gaagtggatt tcttctgctg cgagctcgc               1669
```

<210> SEQ ID NO 17
<211> LENGTH: 141
<212> TYPE: PRT
<213> ORGANISM: Physcomitrella patens

<400> SEQUENCE: 17

```
Met Arg Leu Ala Ala Lys Asp Thr Ser Gly Arg Asn Ala Phe Lys Phe
 1               5                  10                  15

Arg Asn Ile Asp Leu Asn Lys Ala Pro Ser Ala Trp Asp Thr Glu Glu
            20                  25                  30

Val Ser Ala Ser Asn Thr Gly Asp Thr Thr Ser Phe Arg Gly Val Arg
        35                  40                  45

His Arg Pro Glu Leu Asn Lys Trp Val Thr Glu Ile Arg Pro Thr Ser
    50                  55                  60

Gln Lys Arg Lys Ile Trp Leu Gly Thr Tyr Glu Thr Pro Glu Glu Ala
65                  70                  75                  80

Ala Arg Ala Tyr Asp Val Gly Ile Phe Tyr Thr Lys Lys Ile Pro
                85                  90                  95

Tyr Asn Phe Glu Asp Ser Pro Gln Gln Leu Gln Leu Tyr Pro Ile Pro
            100                 105                 110

Pro Glu Leu Pro Trp Glu Ser Phe Ala Ala Leu Val Lys Gln Arg Ala
        115                 120                 125

Thr Ser Ala Ala Lys Arg Ala Arg Val Pro Ser Ser Ser
    130                 135                 140
```

<210> SEQ ID NO 18
<211> LENGTH: 337
<212> TYPE: PRT
<213> ORGANISM: Physcomitrella patens

<400> SEQUENCE: 18

```
Met Val Val Ala Val Ala Val Leu Phe Ala Val Val Leu Phe Ile Leu
 1               5                  10                  15

Cys Leu His Ile Tyr Ala Lys Trp Phe Trp Arg Asn Gln Gly Ala Ile
            20                  25                  30

Val Ala Ser Asp Gly Thr Leu Arg Thr Leu Ser Trp Arg Arg Arg Arg
        35                  40                  45

Tyr Thr Val Pro Val Asn Ala Thr Pro Val Thr Gln Ala Val Gly Leu
    50                  55                  60

Glu Arg Ala Val Ile Glu Ala Leu Pro Thr Phe Glu Phe Asp Gly Glu
```

```
               65                  70                  75                  80
Arg Ala Lys Arg Val Phe Glu Cys Ala Val Cys Leu Glu Glu Phe Glu
                    85                  90                  95

Leu Gly Glu Lys Gly Arg Thr Leu Pro Lys Cys Asp His Ser Phe His
                100                 105                 110

Leu Asp Cys Ile Asp Met Trp Leu His Ser His Ser Thr Cys Pro Leu
            115                 120                 125

Cys Arg Thr Ser Val Gly Ala Asp Glu Thr Glu Lys Thr Glu Ala
        130                 135                 140

Ala Thr Val Met Gln Ile Ser Glu Pro Gln Met Glu Ala Pro Val
145                 150                 155                 160

Met Gly Asp Val Gly Ala Pro Phe Met Ala Ala Met Arg Ala Ser Arg
                165                 170                 175

Arg Ser Gln Arg Ser Arg Gly Gln Leu Pro Ala Leu Asn Ser Ser Pro
                180                 185                 190

Arg Gly Asn Ser Leu Pro Arg Thr Ala Glu Asp Gln Gly Gly Glu Asn
                195                 200                 205

His Arg Arg Ser Gly Thr Ser Glu Thr Ala Val Ala Val Asp Gln Gln
            210                 215                 220

Gln Asn Ile Lys Asp Tyr Glu Thr Pro Ser Gly Ile Pro Ser Asn Val
225                 230                 235                 240

Leu Phe Trp Gly Asn His Ala Gln Met Ser Ser Ala Gly Ala Gly Gly
                245                 250                 255

Ser Ala Glu Ala Arg Ala Ala Ser Ser Ile Arg Ala Pro Phe Gln Val
                260                 265                 270

Thr Ile Asp Ile Pro Arg Ser Gly Pro Ala Ala Val Ser Asn Ser Ser
            275                 280                 285

Asn Val Leu Ser Pro Met Ala Arg Ala Ser Ala Ser Phe Arg Arg Leu
            290                 295                 300

Leu Ser Arg Gly Lys Ser Val Val Ser Pro Gln Thr Gly Glu Asp Gly
305                 310                 315                 320

Val Asp Glu Gly Gly Pro Ser Ser Ser Pro Arg Pro Pro Pro His
                325                 330                 335

Ala

<210> SEQ ID NO 19
<211> LENGTH: 605
<212> TYPE: PRT
<213> ORGANISM: Physcomitrella patens

<400> SEQUENCE: 19

Met Thr Ala Leu Thr Asn Ser Glu Ala Lys Lys Phe Glu Phe Leu
  1               5                  10                  15

Glu Ala Val Ser Gly Thr Met Asp Ala His Leu Arg Tyr Phe Lys Gln
                 20                  25                  30

Gly Tyr Glu Leu Leu His Gln Met Glu Pro Tyr Ile His Gln Val Leu
             35                  40                  45

Thr Tyr Ala Gln Gln Ser Glu Arg Ala Asn Tyr Glu Gln Ala Ala
     50                  55                  60

Leu Ala Asp Arg Met Gln Glu Tyr Arg Gln Glu Val Glu Arg Glu Ser
 65                  70                  75                  80

Gln Arg Ser Ile Asp Phe Asp Ser Ser Gly Asp Gly Ile Gln Gly
                 85                  90                  95

Val Gly Arg Ser Ser His Lys Met Ile Glu Ala Val Met Gln Ser Thr
```

-continued

```
                100                 105                 110
Pro Lys Gly Gln Ile Gln Thr Leu Lys Gln Gly Tyr Leu Leu Lys Arg
            115                 120                 125

Ser Thr Asn Leu Arg Gly Asp Trp Lys Arg Arg Phe Val Leu Asp
130                 135                 140

Ser Arg Gly Met Leu Tyr Tyr Arg Lys Gln Trp Gly Lys Pro Thr
145                 150                 155                 160

Asp Glu Lys Asn Val Ala His His Thr Val Asn Leu Leu Thr Ser Thr
                165                 170                 175

Ile Lys Ile Asp Ala Glu Gln Ser Asp Leu Arg Phe Cys Phe Arg Ile
                180                 185                 190

Ile Ser Pro Ala Lys Ser Tyr Thr Leu Gln Ala Glu Asn Ala Ile Asp
                195                 200                 205

Arg Met Asp Trp Met Asp Lys Ile Thr Gly Val Ile Ser Ser Leu Leu
                210                 215                 220

Asn Asn Gln Ile Ser Glu Gln Val Asp Gly Asp Ser Asp Val Ser
225                 230                 235                 240

Arg Ser Gly Ala Ser Asp Gln Ser Gly His Glu Arg Pro Leu Asp Val
                245                 250                 255

Leu Arg Lys Val Lys Gly Asn Asp Ala Cys Ala Asp Cys Gly Ala Ala
                260                 265                 270

Asp Pro Asp Trp Ala Ser Leu Asn Leu Gly Ile Leu Leu Cys Ile Glu
                275                 280                 285

Cys Ser Gly Val His Arg Asn Met Ser Val Gln Ile Ser Lys Val Arg
                290                 295                 300

Ser Leu Thr Leu Asp Val Lys Val Trp Glu Pro Ser Val Met Ser Tyr
305                 310                 315                 320

Phe Gln Ser Val Gly Asn Ser Tyr Ala Asn Ser Ile Trp Glu Glu Leu
                325                 330                 335

Leu Asn Pro Lys Ser Ser Glu Glu Ser Glu Arg Asn Val Asn Asp
                340                 345                 350

Glu Gly Gln Ser Gly Val Leu Ser Ala Ser Arg Ala Arg Pro Arg Pro
                355                 360                 365

Arg Asp Pro Ile Pro Ile Lys Glu Arg Phe Ile Asn Ala Lys Tyr Val
                370                 375                 380

Glu Lys Lys Phe Val Gln Lys Leu Lys Val Asp Ser Arg Gly Pro Ser
385                 390                 395                 400

Val Thr Arg Gln Ile Trp Asp Ala Val Gln Asn Lys Lys Val Gln Leu
                405                 410                 415

Ala Leu Arg Leu Leu Ile Thr Ala Asp Ala Asn Ala Asn Thr Thr Phe
                420                 425                 430

Glu Gln Val Met Gly Gly Thr Glu Ser Ser Trp Ser Pro Leu Ala
                435                 440                 445

Ser Leu Ala Gly Ala Leu Leu Arg Lys Asn Ser Leu Ser Ala Ser Gln
                450                 455                 460

Ser Gly Arg Arg Asn Trp Ser Val Pro Ser Leu Leu Ser Ser Pro Asp
465                 470                 475                 480

Asp Pro Gly Ser Arg Ser Gly Ala Leu Ser Pro Val Ser Arg Ser Pro
                485                 490                 495

Asp Ala Ala Gly Ser Gly Gly Ile Asp Glu Lys Asp Leu Arg Gly Cys
                500                 505                 510

Ser Leu Leu His Val Ala Cys Gln Ile Gly Asp Ile Ser Leu Ile Glu
                515                 520                 525
```

```
Leu Leu Leu Gln Tyr Gly Ala Gln Ile Asn Cys Val Asp Thr Leu Gly
        530                 535                 540

Arg Thr Pro Leu His His Cys Val Leu Cys Gly Asn Asn Ser Cys Ala
545                 550                 555                 560

Lys Leu Leu Leu Thr Arg Gly Ala Lys Ala Gly Ala Val Asp Lys Glu
                565                 570                 575

Gly Lys Thr Pro Leu Glu Cys Ala Val Glu Lys Leu Gly Ala Ile Thr
                580                 585                 590

Asp Glu Glu Leu Phe Ile Met Leu Ser Glu Thr Ser Arg
            595                 600                 605

<210> SEQ ID NO 20
<211> LENGTH: 188
<212> TYPE: PRT
<213> ORGANISM: Physcomitrella patens

<400> SEQUENCE: 20

Met Ala Thr Glu Arg Val Ser Gln Glu Thr Thr Ser Gln Ala Pro Glu
  1               5                  10                  15

Gly Pro Val Met Cys Lys Asn Leu Cys Gly Phe Phe Gly Ser Gln Ala
             20                  25                  30

Thr Met Gly Leu Cys Ser Lys Cys Tyr Arg Glu Thr Val Met Gln Ala
         35                  40                  45

Lys Met Thr Ala Leu Ala Glu Gln Ala Thr Gln Ala Ala Gln Ala Thr
 50                  55                  60

Ser Ala Thr Ala Ala Val Gln Pro Pro Ala Pro Val His Glu Thr
 65                  70                  75                  80

Lys Leu Thr Cys Glu Val Glu Arg Thr Met Ile Val Pro His Gln Ser
                 85                  90                  95

Ser Ser Tyr Gln Gln Asp Leu Val Thr Pro Ala Ala Ala Ala Pro Gln
            100                 105                 110

Ala Val Lys Ser Ser Ile Ala Ala Pro Ser Arg Pro Glu Pro Asn Arg
        115                 120                 125

Cys Gly Ser Cys Arg Lys Arg Val Gly Leu Thr Gly Phe Lys Cys Arg
    130                 135                 140

Cys Gly Asn Leu Tyr Cys Ala Leu His Arg Tyr Ser Asp Lys His Thr
145                 150                 155                 160

Cys Thr Tyr Asp Tyr Lys Ala Ala Gly Gln Glu Ala Ile Ala Lys Ala
                165                 170                 175

Asn Pro Leu Val Val Ala Glu Lys Val Lys Phe
            180                 185

<210> SEQ ID NO 21
<211> LENGTH: 714
<212> TYPE: PRT
<213> ORGANISM: Physcomitrella patens

<400> SEQUENCE: 21

Met Pro Gly Pro Val Pro Leu Leu Ser Met Ser Val Lys Ser Glu Ser
  1               5                  10                  15

Leu Asp Asp Ile Gly Gly His Glu Lys Lys Ser Val Thr Gly Ser Glu
             20                  25                  30

Val Gly Gly Leu Asp Ala Gln Leu Trp His Ala Cys Ala Gly Gly Met
         35                  40                  45

Val Gln Leu Pro His Val Gly Ala Lys Val Val Tyr Phe Pro Gln Gly
 50                  55                  60
```

```
His Gly Glu Gln Ala Ala Ser Thr Pro Glu Phe Pro Arg Thr Leu Val
 65                  70                  75                  80

Pro Asn Gly Ser Val Pro Cys Arg Val Val Ser Val Asn Phe Leu Ala
                 85                  90                  95

Asp Thr Glu Thr Asp Glu Val Phe Ala Arg Ile Cys Leu Gln Pro Glu
            100                 105                 110

Ile Gly Ser Ser Ala Gln Asp Leu Thr Asp Asp Ser Leu Ala Ser Pro
                115                 120                 125

Pro Leu Glu Lys Pro Ala Ser Phe Ala Lys Thr Leu Thr Gln Ser Asp
130                 135                 140

Ala Asn Asn Gly Gly Gly Phe Ser Ile Pro Arg Tyr Cys Ala Glu Thr
145                 150                 155                 160

Ile Phe Pro Pro Leu Asp Tyr Cys Ile Asp Pro Pro Val Gln Thr Val
                165                 170                 175

Leu Ala Lys Asp Val His Gly Glu Val Trp Lys Phe Arg His Ile Tyr
                180                 185                 190

Arg Gly Thr Pro Arg Arg His Leu Leu Thr Thr Gly Trp Ser Thr Phe
            195                 200                 205

Val Asn Gln Lys Lys Leu Val Ala Gly Asp Ala Ile Val Phe Leu Arg
210                 215                 220

Ile Ala Ser Gly Glu Leu Cys Val Gly Val Arg Arg Ser Met Arg Gly
225                 230                 235                 240

Val Ser Asn Gly Glu Ser Ser Ser Trp His Ser Ser Ile Ser Asn Ala
                245                 250                 255

Ser Thr Ile Arg Pro Ser Arg Trp Glu Val Lys Gly Thr Glu Ser Phe
            260                 265                 270

Ser Asp Phe Leu Gly Gly Val Gly Asp Asn Gly Tyr Ala Leu Asn Ser
            275                 280                 285

Ser Ile Arg Ser Glu Asn Gln Gly Ser Pro Thr Thr Ser Ser Phe Ala
290                 295                 300

Arg Asp Arg Ala Arg Val Thr Ala Lys Ser Val Leu Glu Ala Ala Ala
305                 310                 315                 320

Leu Ala Val Ser Gly Glu Arg Phe Glu Val Val Tyr Tyr Pro Arg Ala
                325                 330                 335

Ser Thr Ala Glu Phe Cys Val Lys Ala Gly Leu Val Lys Arg Ala Leu
            340                 345                 350

Glu Gln Ser Trp Tyr Ala Gly Met Arg Phe Lys Met Ala Phe Glu Thr
            355                 360                 365

Glu Asp Ser Ser Arg Ile Ser Trp Phe Met Gly Thr Ile Ala Ala Val
370                 375                 380

Gln Ala Ala Asp Pro Val Leu Trp Pro Ser Pro Trp Arg Val Leu
385                 390                 395                 400

Gln Val Thr Trp Asp Glu Pro Asp Leu Leu Gln Gly Val Asn Arg Val
                405                 410                 415

Ser Pro Trp Gln Leu Glu Leu Val Ala Thr Leu Pro Met Gln Leu Pro
            420                 425                 430

Pro Val Ser Leu Pro Lys Lys Leu Arg Thr Val Gln Pro Gln Glu
            435                 440                 445

Leu Pro Leu Gln Pro Pro Gly Leu Leu Ser Leu Pro Leu Ala Gly Thr
450                 455                 460

Ser Asn Phe Gly Gly His Leu Ala Thr Pro Trp Gly Ser Ser Val Leu
465                 470                 475                 480
```

-continued

```
Leu Asp Asp Ala Ser Val Gly Met Gln Gly Ala Arg His Asp Gln Phe
                485                 490                 495
Asn Gly Leu Pro Thr Val Asp Phe Arg Asn Ser Asn Tyr Lys His Pro
            500                 505                 510
Arg Glu Phe Ser Arg Asp Asn Gln Tyr Gln Ile Gln Asp His Gln Val
        515                 520                 525
Phe His Pro Arg Pro Val Leu Asn Glu Pro Ala Thr Asn Thr Gly
    530                 535                 540
Asn Tyr Phe Ser Leu Leu Pro Ser Leu Gln Arg Arg Pro Asp Ile Ser
545                 550                 555                 560
Pro Ser Ile Gln Pro Leu Ala Phe Met Ser Ala Gly Ser Ser Gln
                565                 570                 575
Leu Glu Thr Ser Ser Thr Lys Thr Ala Ala Thr Ser Phe Phe Leu Phe
                580                 585                 590
Gly Gln Phe Ile Asp Pro Ser Cys Thr Ser Lys Pro Gln Gln Arg Ser
            595                 600                 605
Thr Val Ile Asn Asn Ala Ser Val Ala Gly Asp Gly Lys His Pro Gly
        610                 615                 620
Thr Asn Asn Ser Ser Ser Asp Asn Lys Ser Glu Asp Lys Asp Asn Cys
625                 630                 635                 640
Arg Asp Val Gln Pro Ile Leu Asn Gly Ile Ala Val Arg Ser Gly Phe
                645                 650                 655
Arg Ala Asp Ile Ala Ala Lys Lys Phe Gln Gln Ser Asp Ser Ala His
                660                 665                 670
Pro Thr Glu Ala Ser Arg Gly Ser Gln Val Ser Ser Leu Pro Trp Trp
            675                 680                 685
Gln Thr Gln Asp Ala His Lys Asp Gln Glu Phe His Gly Asp Ser Gln
        690                 695                 700
Thr Pro His Thr Pro Ala Ser Gly Ser Gln
705                 710

<210> SEQ ID NO 22
<211> LENGTH: 469
<212> TYPE: PRT
<213> ORGANISM: Physcomitrella patens

<400> SEQUENCE: 22

Met Lys Glu Leu Asn Glu Asp Met Glu Ile Pro Leu Gly Arg Asp Gly
  1               5                  10                  15
Glu Gly Met Gln Ser Lys Gln Cys Pro Arg Gly His Trp Arg Pro Ala
            20                  25                  30
Glu Asp Asp Lys Leu Arg Glu Leu Val Ser Gln Phe Gly Pro Gln Asn
        35                  40                  45
Trp Asn Leu Ile Ala Glu Lys Leu Gln Gly Arg Ser Gly Lys Ser Cys
    50                  55                  60
Arg Leu Arg Trp Phe Asn Gln Leu Asp Pro Arg Ile Asn Arg His Pro
65                  70                  75                  80
Phe Ser Glu Glu Glu Glu Arg Leu Leu Ile Ala His Lys Arg Tyr
                85                  90                  95
Gly Asn Lys Trp Ala Leu Ile Ala Arg Leu Phe Pro Gly Arg Thr Asp
            100                 105                 110
Asn Ala Val Lys Asn His Trp His Val Val Thr Ala Arg Gln Ser Arg
        115                 120                 125
Glu Arg Thr Arg Thr Tyr Gly Arg Ile Lys Gly Pro Val His Arg Arg
    130                 135                 140
```

Gly Lys Gly Asn Arg Ile Asn Thr Ser Ala Leu Gly Asn Tyr His His
145                 150                 155                 160

Asp Ser Lys Gly Ala Leu Thr Ala Trp Ile Glu Ser Lys Tyr Ala Thr
            165                 170                 175

Val Glu Gln Ser Ala Glu Gly Leu Ala Arg Ser Pro Cys Thr Gly Arg
        180                 185                 190

Gly Ser Pro Pro Leu Pro Thr Gly Phe Ser Ile Pro Gln Ile Ser Gly
            195                 200                 205

Gly Ala Phe His Arg Pro Thr Asn Met Ser Thr Ser Pro Leu Ser Asp
    210                 215                 220

Val Thr Ile Glu Ser Pro Lys Phe Ser Asn Ser Glu Asn Ala Gln Ile
225                 230                 235                 240

Ile Thr Ala Pro Val Leu Gln Lys Pro Met Gly Asp Pro Arg Ser Val
                245                 250                 255

Cys Leu Pro Asn Ser Thr Val Ser Asp Lys Gln Gln Val Leu Gln Ser
            260                 265                 270

Asn Ser Ile Asp Gly Gln Ile Ser Ser Gly Leu Gln Thr Ser Ala Ile
        275                 280                 285

Val Ala His Asp Glu Lys Ser Gly Val Ile Ser Met Asn His Gln Ala
    290                 295                 300

Pro Asp Met Ser Cys Val Gly Leu Lys Ser Asn Phe Gln Gly Ser Leu
305                 310                 315                 320

His Pro Gly Ala Val Arg Ser Ser Trp Asn Gln Ser Leu Pro His Cys
                325                 330                 335

Phe Gly His Ser Asn Lys Leu Val Glu Glu Cys Arg Ser Ser Thr Gly
            340                 345                 350

Ala Cys Thr Glu Arg Ser Glu Ile Leu Gln Glu Gln His Ser Ser Leu
        355                 360                 365

Gln Phe Lys Cys Ser Thr Ala Tyr Asn Thr Gly Arg Tyr Gln His Glu
    370                 375                 380

Asn Leu Cys Gly Pro Ala Phe Ser Gln Gln Asp Thr Ala Asn Glu Val
385                 390                 395                 400

Ala Asn Phe Ser Thr Leu Ala Phe Ser Gly Leu Val Lys His Arg Gln
                405                 410                 415

Glu Arg Leu Cys Lys Asp Ser Gly Ser Ala Leu Lys Leu Gly Leu Ser
            420                 425                 430

Trp Val Thr Ser Asp Ser Thr Leu Asp Leu Ser Val Ala Lys Met Ser
        435                 440                 445

Ala Ser Gln Pro Glu Gln Ser Ala Pro Val Ala Phe Ile Asp Phe Leu
    450                 455                 460

Gly Val Gly Ala Ala
465

<210> SEQ ID NO 23
<211> LENGTH: 218
<212> TYPE: PRT
<213> ORGANISM: Physcomitrella patens

<400> SEQUENCE: 23

Met Ala Asp Ser Tyr Gly His Asn Ala Gly Ser Pro Glu Ser Ser Pro
 1               5                  10                  15

His Ser Asp Asn Glu Ser Gly Gly His Tyr Arg Asp Gln Asp Ala Ser
            20                  25                  30

Val Arg Glu Gln Asp Arg Phe Leu Pro Ile Ala Asn Val Ser Arg Ile

```
                        35                  40                  45
Met Lys Lys Ala Leu Pro Ser Asn Ala Lys Ile Ser Lys Asp Ala Lys
         50                  55                  60

Glu Thr Val Gln Glu Cys Val Ser Glu Phe Ile Ser Phe Ile Thr Gly
 65                  70                  75                  80

Glu Ala Ser Asp Lys Cys Gln Arg Glu Lys Arg Lys Thr Ile Asn Gly
                 85                  90                  95

Asp Asp Leu Leu Trp Ala Met Ser Thr Leu Gly Phe Glu Asp Tyr Val
             100                 105                 110

Glu Pro Leu Lys Val Tyr Leu His Lys Tyr Arg Glu Leu Glu Gly Glu
         115                 120                 125

Lys Ala Ser Thr Ala Lys Gly Gly Asp Gln Gln Gly Gly Lys Glu Gly
     130                 135                 140

Ser Gln Gly Val Met Gly Ser Met Gly Met Ser Gly Gly Met Asn Gly
145                 150                 155                 160

Met Asn Gly Thr Met Asn Gly Asn Met His Gly His Gly Ile Pro Val
                165                 170                 175

Ser Met Gln Met Leu Gln Gln Ser Tyr Gly Gln Gln Ala Pro Pro Gly
            180                 185                 190

Met Met Tyr Ser Pro His Gln Met Met Pro Gln Tyr Gln Met Pro Met
        195                 200                 205

Gln Ser Gly Gly Asn Gln Pro Arg Gly Val
    210                 215

<210> SEQ ID NO 24
<211> LENGTH: 412
<212> TYPE: PRT
<213> ORGANISM: Physcomitrella patens

<400> SEQUENCE: 24

Met Met Glu Ala Glu Gln Ser Tyr Val Gln Lys Leu Glu Ser Leu Leu
  1               5                  10                  15

Gly Gly Val Ser Thr Leu Val Arg Glu Glu Glu Thr Ala Ser Val
             20                  25                  30

Ser Glu Asp Glu Asp Ser Asn Ser Leu Pro Gln Ile Gln Val Ala
         35                  40                  45

Val Lys Ser Lys Arg Lys Gly Glu Arg Lys Arg Arg Glu Arg Ala
     50                  55                  60

Leu Glu Arg Ala Glu Lys Val Ala Thr Asp Leu Ala Ser Ala Pro Pro
 65                  70                  75                  80

Leu Pro Lys Pro Lys Lys Pro Gln Leu Ala Ala Asp Pro Ser Asp Pro
                 85                  90                  95

Val Arg Ala Tyr Leu Arg Asp Ile Gly Arg Thr Lys Leu Leu Thr Ala
             100                 105                 110

Arg Glu Glu Val Asp Leu Ser His Gln Ile Gln Asp Leu Leu Lys Leu
         115                 120                 125

Glu Asn Ile Lys Ser Asn Leu Glu Arg Glu Ile Gly Arg Asn Ala Thr
     130                 135                 140

Ile Gly Glu Trp Ser Arg Ala Val Gly Met Glu Gln Asn Ala Phe Glu
145                 150                 155                 160

Ala Arg Leu Lys Lys Gly Arg Phe Ala Lys Asp Lys Met Val Asn Ser
                165                 170                 175

Asn Leu Arg Leu Val Val Ser Ile Ala Lys Asn Tyr Gln Gly Arg Gly
            180                 185                 190
```

```
Met Thr Leu Gln Asp Leu Ile Gln Glu Gly Ser Met Gly Leu Val Arg
        195                 200                 205

Gly Ala Glu Lys Phe Asp Pro Thr Lys Gly Phe Lys Phe Ser Thr Tyr
    210                 215                 220

Ala His Trp Trp Ile Arg Gln Ala Val Thr Arg Ser Ile Ala Asp Gln
225                 230                 235                 240

Ser Arg Thr Phe Arg Leu Pro Ile His Leu Tyr Glu Val Ile Ser Arg
                245                 250                 255

Ile Asn Lys Ala Lys Arg Met Leu Val Gln Glu His Gly Arg Glu Ala
            260                 265                 270

Arg Asn Glu Glu Val Ala Glu Leu Val Gly Leu Thr Val Glu Lys Leu
        275                 280                 285

Lys Ser Val Val Lys Ser Ala Lys Ala Pro Gly Ser Met Glu Arg Pro
    290                 295                 300

Ile Gly Lys Asp Gly Asp Thr Thr Leu Gly Glu Leu Val Ala Asp Thr
305                 310                 315                 320

Asp Val Asp Ser Pro Glu Asp Ala Ile Val Lys Gln Leu Met Arg Gln
                325                 330                 335

Asp Ile Glu Gly Val Leu Arg Thr Leu Asn Pro Arg Glu Arg Glu Val
            340                 345                 350

Leu Arg Leu Arg Phe Gly Leu Asp Asp Gly Arg Ser Lys Thr Leu Glu
        355                 360                 365

Glu Ile Gly Gln Ile Phe Lys Ala Thr Arg Glu Arg Ile Arg Gln Ile
    370                 375                 380

Glu Ala Lys Ala Met Arg Lys Leu Arg Gln Pro Ser Arg Asn Ser Ile
385                 390                 395                 400

Leu Arg Glu Tyr Leu Asp Val Lys Ser Asp Ala Ile
                405                 410

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 25
caggaaacag ctatgacc                                                 18

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 26
ctaaagggaa caaaagctg                                                19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 27
tgtaaaacga cggccagt                                                 18
```

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 28
atcccgggca gcgagcacac agctagcaac tctt                               34

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 29
gcgagctcac tccctcacgc ggttgacaat ct                                 32

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
tggcggcctc ggtcttcttc tcagt                                         25

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 31
atcccgggag gaagctgtca gggaagagat gga                                33

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 32
gcgagctctg gccgtaaaat cagttgtggc gctt                               34

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 33
cagcgaagcc caatcgggat cagca                                         25

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Primer

```
<400> SEQUENCE: 34
atcccgggag gaggacttgc ggaatgcaaa tc                                32

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 35
gcgatatcca cctgcttcca ctctctactt atg                               33

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 36
gacacccgat tgagccggca agacg                                        25

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 37
atcccgggca ccagtcccgc ttagtgtgtg tgt                               33

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 38
gcgagctctt gatgcgactc gctctctcga t                                 31

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 39
cggcgagtgc agcagcttct agaacg                                       26

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 40
atcccgggta tcgatctgga gcccgttgca a                                 31

<210> SEQ ID NO 41
<211> LENGTH: 32
```

```
<212> TYPE: DNA
<213> ORGANISM: Artificial Sequence
<220> FEATURE:
<223> OTHER INFORMATION: Description of Artificial Sequence: Primer

<400> SEQUENCE: 41
gcgagctcct ccaaaggact ttgaaatata gc                                    32

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 42
gatatcggaa gaagaatcca agggaatgcg gtt                                   33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 43
gcgagctcta tgcttccgtg ggaggagctt cac                                   33

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 44
ccggctgggt tgcctcagct tgcgca                                           26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 45
cgctccatcg aacctggtgc ctttgc                                           26

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 46
atcccgggct cggaaggact gtgcattgtc ga                                    32

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 47
```

-continued gcgagctcgc agcagaagaa atccacttct ggt                                    33

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 48
gggtgccggt tgatgcgagg gtccag                                            26

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 49
atcccgggct gttgtgtaca gtctgtgga                                         29

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 50
atcccgggct cacggagtaa aggccgtacc tt                                     32

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 51
gcgctgcaga tttcatttgg agaggacacg                                        30

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 52
cgcggccggc ctcagaagaa ctcgtcaaga aggcg                                  35

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 53
gctgacacgc caagcctcgc tagtc                                             25

<210> SEQ ID NO 54
<211> LENGTH: 32
<212> TYPE: DNA
<213> ORGANISM: Artificial Sequence

```
<220> FEATURE:
<223> OTHER INFORMATION: Description of Artificial Sequence: Primer

<400> SEQUENCE: 54
gcgagctcac tccctcacgc ggttgacaat ct                                    32

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 55
gcgagctctg gccgtaaaat cagttgtggc gctt                                  34

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 56
gcgatatcca cctgcttcca ctctctactt atg                                   33

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 57
gcgagctctt gatgcgactc gctctctcga t                                     31

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 58
gcgagctcct ccaaaggact ttgaaatata gc                                    32

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 59
gcgagctcta tgcttccgtg ggaggagctt cac                                   33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 60
gcgagctcgc agcagaagaa atccacttct ggt                                   33
```

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 61
atcccgggct cacggagtaa aggccgtacc tt					32

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 62
atcccgggca gcgagcacac agctagcaac tctt					34

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 63
gcgagctcac tccctcacgc ggttgacaat ct					32

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 64
gcccgttgtg tcgcacgagt gtggga						26

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 65
gccgctggac cagacctcgg aatgt						25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 66
gaggcagtca tgcaatcgac cccaa						25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 67
gcgaagccca atcgggatca gcagca                          26

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 68
atcccgggca ccagtcccgc ttagtgtgtg tgt                  33

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 69
gcgagctctt gatgcgactc gctctctcga t                    31

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 70
cgcatcgcat ctggcgaact ttgtg                           25

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 71
cgtaccacga ttgctctagc gcacgt                          26

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 72
gcgatatcgg aagaagaatc caagggaatg cggtt                35

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 73
gcgagctcta tgcttccgtg ggaggagctt cac                  33

<210> SEQ ID NO 74

<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 74
atcccgggca gcgagcacac agctagcaac tctt                   34

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 75
gcgagctcac tccctcacgc ggttgacaat ct                     32

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 76
gcccgttgtg tcgcacgagt gtggga                            26

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 77
gccgctggac cagacctcgg aatgt                             25

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 78
gaggcagtca tgcaatcgac cccaa                             25

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 79
gcgaagccca atcgggatca gcagca                            26

US 7,709,698 B2

TRANSCRIPTION FACTOR STRESS-RELATED PROTEINS AND METHODS OF USE IN PLANTS

CROSS REFERENCE TO RELATED APPLICATIONS

This application is a divisional of U.S. Nonprovisional patent application Ser. No. 09/828,303 filed Apr. 6, 2001, and is copending with allowed U.S. Nonprovisional application Ser. No. 11/566,282, filed Dec. 4, 2006, which is a continuation application of allowed U.S. Nonprovisional application Ser. No. 10/716,089, filed Nov. 18, 2003 and now U.S. Pat. No. 7,161,063, which is a divisional application of U.S. Nonprovisional patent application Ser. No. 09/828,303 filed Apr. 6, 2001 and now U.S. Pat. No. 6,677,504, which claims the priority benefit of U.S. Provisional Application Ser. No. 60/196,001 filed Apr. 7, 2000, each of which is hereby incorporated in its entirety.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

One model plant used in the study of stress tolerance is *Arabidopsis thaliana*. There are at least four different signal-transduction pathways leading to stress tolerance in the model plant *Arabidopsis thaliana*. These pathways are under the control of distinct transcription factors (Shinozaki et al., 2000 Curr. Op. Pl. Biol. 3:217-23). Regulators of genes, especially transcription factors, involved in these tolerance pathways are particularly suitable for engineering tolerance into plants because a single gene can activate a whole cascade of genes leading to the tolerant phenotype. Consequently, transcription factors are important targets in the quest to identify genes conferring stress tolerance to plants.

One transcription factor that has been identified in the prior art is the *Arabidopsis thaliana* transcription factor CBF (Jaglo-Ottosen et al., 1998 Science 280:104-6). Over-expression of this gene in *Arabidopsis* conferred drought tolerance to this plant (Kasuga et al., 1999 Nature Biotech. 17:287-91). However, CBF is the only example to date of a transcription factor able to confer drought tolerance to plants upon over-expression.

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique transcription factors capable of conferring stress tolerance to plants upon over-expression. The present invention provides a transgenic plant cell transformed by a Transcription Factor Stress-Related Protein (TFSRP) coding nucleic acid, wherein expression of the nucleic acid sequence in the plant cell results in increased tolerance to environmental stress as compared to a wild type variety of the plant cell. Namely, described herein are the transcription factors 1) CAAT-Box like Binding Factor-3 (CABF-3); 2) Zinc Finger-2 (ZF-2) 3) Zinc Finger-3 (ZF-3); 4) Zinc Finger-4 (ZF-4); 5) Zinc Finger-5 (ZF-5); 6) AP2 Similar Factor-2 (APS-2); 7) Sigma Factor Like Factor-1 (SFL-1); and 8) MYB Factor-1 (MYB-1), all from *Physcomitrella patens*.

The invention provides in some embodiments that the TFSRP and coding nucleic acid are that found in members of the genus *Physcomitrella*. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought or cold temperature.

The invention further provides a seed produced by a transgenic plant transformed by a TFSRP coding nucleic acid, wherein the plant is true breeding for increased tolerance to environmental stress as compared to a wild type variety of the plant. The invention further provides a seed produced by a transgenic plant expressing a TFSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated TFSRP as described below. The invention further provides an isolated TFSRP coding nucleic acid, wherein the TFSRP coding nucleic acid codes for a TFSRP as described below.

The invention further provides an isolated recombinant expression vector comprising a TFSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a TFSRP coding nucleic acid, wherein expression of the nucleic acid in the plant results in increased tolerance to environmental stress as compared to a wild type variety of the plant comprising: (a) transforming a plant cell with an expression vector comprising a TFSRP coding nucleic acid, and (b) generating from the plant cell a transgenic plant with an increased tolerance to environmental stress as compared to a wild type variety of the plant. In preferred embodiments, the TFSRP and TFSRP coding nucleic acid are as described below.

The present invention further provides a method of identifying a novel TFSRP, comprising (a) raising a specific antibody response to a TFSRP, or fragment thereof, as described below; (b) screening putative TFSRP material with the antibody, wherein specific binding of the antibody to the material indicates the presence of a potentially novel TFSRP; and (c) identifying from the bound material a novel TFSRP in comparison to known TFSRP. Alternatively, hybridization with nucleic acid probes as described below can be used to identify novel TFSRP nucleic acids.

The present invention also provides methods of modifying stress tolerance of a plant comprising, modifying the expression of a TFSRP in the plant, wherein the TFSRP is as described below. The invention provides that this method can be performed such that the stress tolerance is either increased or decreased. Preferably, stress tolerance is increased in a plant via increasing expression of a TFSRP.

BRIEF DESCRIPTION OF THE DRAWINGS

FIG. 2 shows the results of a drought stress test with over-expressing PpZF-2 transgenic plants and wild-type *Arabidopsis* lines. The transgenic lines display a tolerant phenotype. Individual transformant lines are shown.

FIG. 3 shows the results of a drought stress test with over-expressing PpZF-3 transgenic plants and wild-type *Arabidopsis* lines. The transgenic lines display a tolerant phenotype. Individual transformant lines are shown.

FIG. 4 shows the results of a drought stress test with over-expressing PpZF-4 transgenic plants and wild-type *Arabidopsis* lines. The transgenic lines display a tolerant phenotype. Individual transformant lines are shown.

FIG. 5 shows the results of a drought stress test with over-expressing PpZF-5 transgenic plants and wild-type *Arabidopsis* lines. The transgenic lines display a tolerant phenotype. Individual transformant lines are shown.

FIG. 6 shows the results of a drought stress test with over-expressing PpCABF-3 transgenic plants and wild-type *Arabidopsis* lines. The transgenic lines display a tolerant phenotype. Individual transformant lines are shown.

FIG. 7 shows the results of a drought stress test with over-expressing PpAPS-2 transgenic plants and wild-type *Arabidopsis* lines. The transgenic lines display a tolerant phenotype. Individual transformant lines are shown.

FIG. 9 shows the results of a drought stress test with over-expressing PpMYB-1 transgenic plants and wild-type *Arabidopsis* lines. The transgenic lines display a tolerant phenotype. Individual transformant lines are shown.

FIG. 10 shows the results of a freezing stress test with over-expressing PpCABF-3 transgenic plants and wild-type *Arabidopsis* lines. The transgenic lines display a tolerant phenotype. Individual transformant lines are shown.

FIG. 11 shows the results of a freezing stress test with over-expressing PpZF-2 transgenic plants and wild-type *Arabidopsis* lines. The transgenic lines display a tolerant phenotype. Individual transformant lines are shown.

FIG. 12 shows the results of a freezing stress test with over-expressing PpZF-3 transgenic plants and wild-type *Arabidopsis* lines. The transgenic lines display a tolerant phenotype. Individual transformant lines are shown.

DETAILED DESCRIPTION OF THE INVENTION

Figure 1:
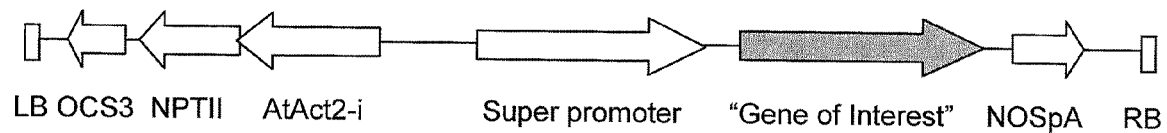
FIG. 1 shows a diagram of the plant expression vector pBPSSC022 containing the super promoter driving the expression of SEQ ID NOs: 9, 10, 11, 12, 13, 14, 15, and 16 ("Desired Gene"). The components are: NPTII kanamycin resistance gene (Hajdukiewicz et al. 1994 Pl. Mol Biol. 25:989-98), AtAct2-i promoter (An et al. 1996 Plant J. 10:107-21), OCS3 terminator (Weigel et al. 2000 Pl. Physiol. 122: 1003-13).
Figure 8:
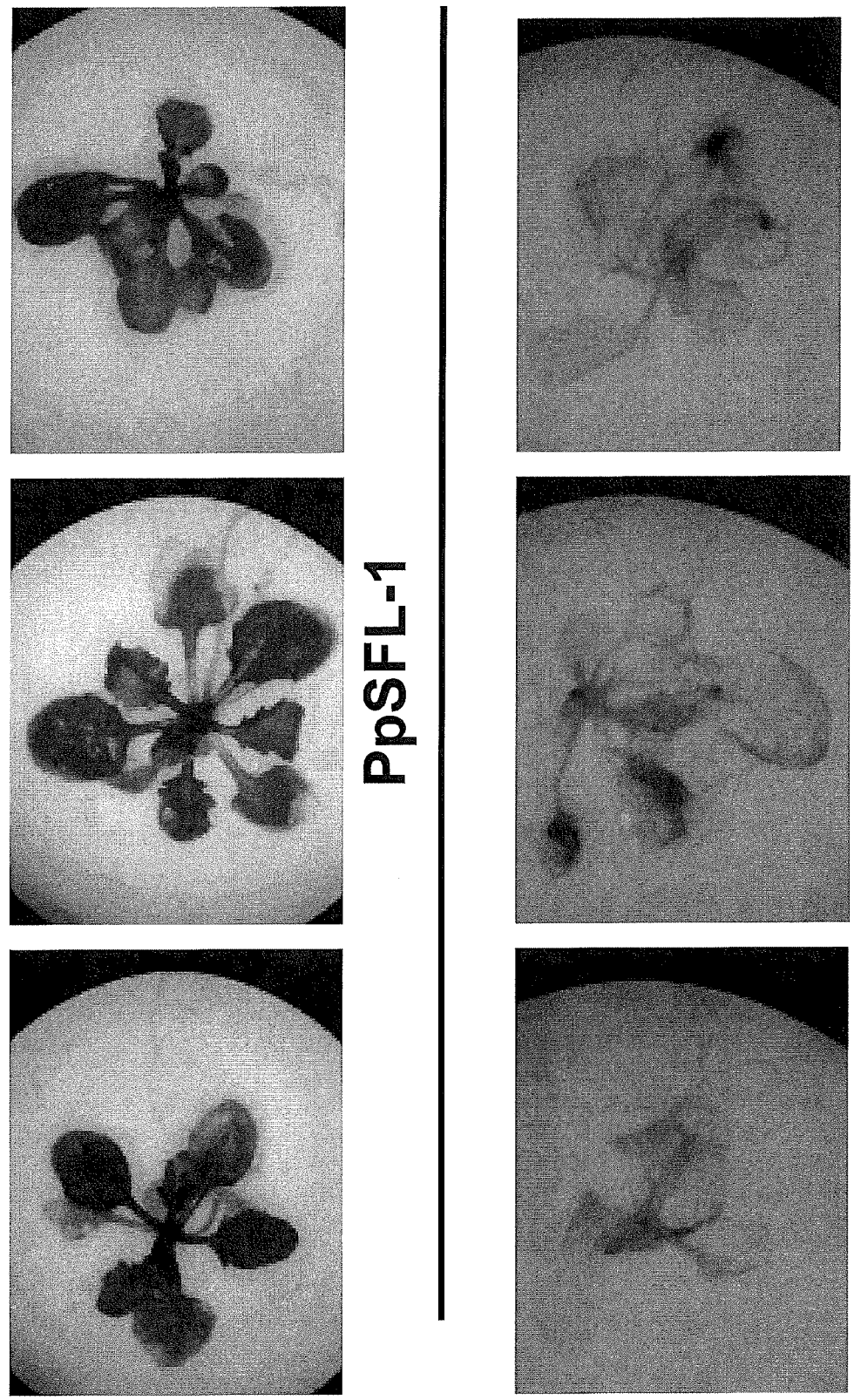
FIG. 8 shows the results of a drought stress test with over-expressing PpSFL-1 transgenic plants and wild-type *Arabidopsis* lines. The transgenic lines display a tolerant phenotype. Individual transformant lines are shown.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as protein "Transcription Factor Stress-Related Proteins" (TFSRPs), in no way limits the functionality of those sequences.

The present invention provides a transgenic plant cell transformed by a TFSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Also provided is a plant seed produced by a transgenic plant transformed by a TFSRP coding nucleic acid, wherein the seed contains the TFSRP coding nucleic acid, and wherein the plant is true breeding for increased tolerance to environmental stress as compared to a wild type variety of the plant. The invention further provides a seed produced by a transgenic plant expressing a TFSRP, wherein the seed contains the TFSRP, and wherein the plant is true breeding for increased tolerance to environmental stress as compared to a wild type variety of the plant. The invention also provides an agricultural product produced by any of the below-described transgenic plants, plant parts and plant seeds.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* TFSRPs, APS-2, ZF-2, ZF-3, ZF-4, ZF-5, MYB-1, CABF-3 and SFL-1, are useful for increasing a plant's tolerance to environmental stress. The PpAPS-2 protein (AP2 Similar) contains a region of similarity with the AP2 domain present in some plant transcription factors. Apetala-2 (AP2) is a homeotic gene in *Arabidopsis* and mutations in this gene result in the generation of flowers without petals. The AP2 domain is found in not only homeotic genes in plants, but also in proteins with diverse function.

Another group of novel predicted proteins described herein are PpZF-2, PpZF-3, PpZF-4 and PpZF-5, which show sequence similarity to the Zinc-Finger class of transcription factors. Zinc-finger transcription factors share in common a specific secondary structure wherein a zinc molecule is sequestered by the interaction with cysteine or histidine amino acid residues. Through these "fingers," the proteins interact with their specific DNA targets and regulate transcription of the target genes. Zinc-finger factors are associated with a multitude of biological phenomena. For example, in yeast zinc fingers are related with the regulation of multiple genes, e.g. genes involved in general metabolism. In plants, a zinc-finger protein, CONSTANS, is responsible for determining flowering time (Putterill et al. 1995 Cell 80:847-57). Sakamoto et al. (2000 Gene 248:23-32) also report the activation of the gene expression of three zinc finger proteins in *Arabidopsis* during water-stress treatments. They did not, however, present any data linking this increased expression with stress tolerance. Finally, Lippuner et al. (1996 JBC 271: 12859-66) have reported that a particular class of zinc-finger proteins was able to confer salt tolerance to yeast mutants, however no data showing increased salt tolerance to whole plants was presented.

Another novel predicted protein described herein is a PpMYB-1 protein that shares sequence homology with transcription factors from the MYB family. This group of transcription factors have the highest degree of homology in the "MYB domain". In addition to being involved in pigment formation in maize (Shinozaki et al. 2000. Curr. Op. Pl. Biol. 3: 217-23), it has also been proposed that a MYB-containing protein is involved in regulating stress-related gene expression in plants. In particular, a MYB-containing protein, AtMYB2 has been shown to be stress-induced (PCT Application No. WO 99/16878). However, no data has been presented, demonstrating that the over-expression of AtMYB2 leads to stress tolerance in a plant.

Yet another novel predicted protein described herein is PpCABF-3, which is similar to the domain "B" of other CAAT-Box Binding Factors (Johnson and McKnight, 1989. Ann. Rev. Biochem. 58:799-840). In general, CABFs are parts of multi-component transcription activation complexes and act as general transcriptional regulators and activators. The particular combination of the different CABFs and other sub-units in the complex determines the target genes. PpCABF-3 seems to be important for the activation of stress-related genes upon over-expression in *Arabidopsis thaliana*. PpCABF-3 is homologous to other two CAAT-Box Binding Factors from *Physcomitrella patens*, namely PpCABF-1 and PpCABF-2. Based upon a phylogenic analysis, it is believed that these proteins belong to an exclusive class of CAAT-Box Binding proteins.

A final group of novel predicted proteins described herein includes the PpSFL-1 (Sigma Factor Like) protein. The SFL-1 shares a high degree of sequence with prokaryotic and plant chloroplast sigma factors. Sigma factors are essential for determining promoter recognition and consequently correct transcription initiation in prokaryotes as well as in chloroplasts. Chloroplasts are a major target for engineering stress tolerance, since these organelles are heavily impaired during stress conditions. Attenuation of chloroplast damage can lead to increased stress tolerance in plants.

Accordingly, the present invention provides isolated TFSRPs selected from the group consisting of APS-2, ZF-2, ZF-3, ZF-4, ZF-5, MYB-1, CABF-3, SFL-1 and homologs thereof. In preferred embodiments, the TFSRP is selected from 1) an AP2 Similar-2 (APS-2) protein as defined in SEQ ID NO:17; 2) a Zinc-Finger Factor-2 (ZF-2) protein as defined in SEQ ID NO:18; 3) a Zinc-Finger Factor-3 (ZF-3) protein as defined in SEQ ID NO:19; 4) a Zinc-Finger Factor-4 (ZF-4) protein as defined in SEQ ID NO:20; 5) a Zinc-Finger Factor-5 (ZF-5) protein as defined in SEQ ID NO:21; 6) an MYB-1 (MYB-1) protein as defined in SEQ ID NO:22; 7) a CAAT-Box Binding Factor-3 (CABF-3) protein as defined in SEQ ID NO:23; 8) a Sigma Factor Like (SFL-1) protein as defined in SEQ ID NO:24, and homologs and orthologs thereof. Homologs and orthologs of the amino acid sequences are defined below.

The TFSRPs of the present invention are preferably produced by recombinant DNA techniques. For example, a nucleic acid molecule encoding the protein is cloned into an expression vector (as described below), the expression vector is introduced into a host cell (as described below) and the TFSRP is expressed in the host cell. The TFSRP can then be isolated from the cells by an appropriate purification scheme using standard protein purification techniques. Alternative to recombinant expression, a TFSRP polypeptide, or peptide can be synthesized chemically using standard peptide synthesis techniques. Moreover, native TFSRP can be isolated from cells (e.g., *Physcomitrella patens*), for example using an anti-TFSRP antibody, which can be produced by standard techniques utilizing a TFSRP or fragment thereof.

The invention further provides an isolated TFSRP coding nucleic acid. The present invention includes TFSRP coding nucleic acids that encode TFSRPs as described herein. In preferred embodiments, the TFSRP coding nucleic acid is selected from 1) an AP2 Similar-2 (APS-2) nucleic acid as defined in SEQ ID NO:9; 2) a Zinc-Finger Factor-2 (ZF-2) nucleic acid as defined in SEQ ID NO:10; 3) a Zinc-Finger Factor-3 (ZF-3) nucleic acid as defined in SEQ ID NO:11; 4)

a Zinc-Finger Factor-4 (ZF-4) nucleic acid as defined in SEQ ID NO:12; 5) a Zinc-Finger Factor-5 (ZF-5) nucleic acid as defined in SEQ ID NO:13; 6) an MYB-1 nucleic acid as defined in SEQ ID NO:14; 7) a CAAT-Box Binding Factor-3 (CABF-3) nucleic acid as defined in SEQ ID NO:15; 8) a Sigma Factor Like (SFL-1) nucleic acid as defined in SEQ ID NO:16 and homologs and orthologs thereof. Homologs and orthologs of the nucleotide sequences are defined below. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated TFSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:9, SEQ ID NO:10, SEQ ID NO:11, SEQ ID NO:12, SEQ ID NO:13, SEQ ID NO:14, SEQ ID NO:15, SEQ ID NO:16, or a portion thereof, can be isolated using standard molecular biology techniques and the sequence information provided herein. For example, a *P. patens* TFSRP cDNA can be isolated from a *P. patens* library using all or portion of one of the sequences of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. Moreover, a nucleic acid molecule encompassing all or a portion of one of the sequences of SEQ ID NO:1, SEQ ID NO:2, SEQ ID NO:3, SEQ ID NO:4, SEQ ID NO:5, SEQ ID NO:6, SEQ ID NO:7 and SEQ ID NO:8 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2, SEQ ID NO:3, SEQ ID NO:4, SEQ ID NO:5, SEQ ID NO:6, SEQ ID NO:7 and SEQ ID NO:8. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a TFSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16. These cDNAs comprise sequences encoding the TFSRPs (i.e., the "coding region", indicated in Table 1), as well as 5' untranslated sequences and 3' untranslated sequences. It is to be understood that SEQ ID NO:9, SEQ ID NO:10, SEQ ID NO:11, SEQ ID NO:12, SEQ ID NO:13, SEQ ID NO:14, SEQ ID NO:15 and SEQ ID NO:16 comprise both coding regions and 5' and 3' untranslated regions. Alternatively, the nucleic acid molecules of the present invention can comprise only the coding region of any of the sequences in SEQ ID NO:9, SEQ ID NO:10, SEQ ID NO:11, SEQ ID NO:12, SEQ ID NO:13, SEQ ID NO:14, SEQ ID NO:15 or SEQ ID NO:16 or can contain whole genomic fragments isolated from genomic DNA. A coding region of these sequences is indicated as "ORF position". The present invention also includes TFSRP coding nucleic acids that encode TFSRPs as described herein. Preferred is a TFSRP coding nucleic acid that encodes a TFSRP selected from the group consisting of, APS-2 (SEQ ID NO:17), ZF-2 (SEQ ID NO:18), ZF-3 (SEQ ID NO:19), ZF-4 (SEQ ID NO:20), ZF-5 (SEQ ID NO:21), MYB-1 (SEQ ID NO:22), CABF-3 (SEQ ID NO:23) and SFL-1 (SEQ ID NO:24).

Moreover, the nucleic acid molecule of the invention can comprise only a portion of the coding region of one of the sequences in SEQ ID NO:9, SEQ ID NO:10, SEQ ID NO:11, SEQ ID NO:12, SEQ ID NO:13, SEQ ID NO:14, SEQ ID NO:15 and SEQ ID NO:16, for example, a fragment which can be used as a probe or primer or a fragment encoding a biologically active portion of a TFSRP. The nucleotide sequences determined from the cloning of the TFSRP genes from *P. patens* allow for the generation of probes and primers designed for use in identifying and/or cloning TFSRP homologs in other cell types and organisms, as well as TFSRP homologs from other mosses and related species.

Portions of proteins encoded by the TFSRP nucleic acid molecules of the invention are preferably biologically active portions of one of the TFSRPs described herein. As used herein, the term "biologically active portion of" a TFSRP is intended to include a portion, e.g., a domain/motif, of a TFSRP that participates in a stress tolerance response in a plant, has an activity as set forth in Table 1, or participates in the transcription of a protein involved in a stress tolerance response in a plant. To determine whether a TFSRP, or a biologically active portion thereof, can participate in transcription of a protein involved in a stress tolerance response in a plant, or whether repression of a TFSRP results in increased stress tolerance in a plant, a stress analysis of a plant comprising the TFSRP may be performed. Such analysis methods are well known to those skilled in the art, as detailed in Example 7. More specifically, nucleic acid fragments encoding biologically active portions of a TFSRP can be prepared by isolating a portion of one of the sequences in SEQ ID NO:17, SEQ ID NO:18, SEQ ID NO:19, SEQ ID NO:20, SEQ ID NO:21, SEQ ID NO:22, SEQ ID NO:23 and SEQ ID NO:24, expressing the encoded portion of the TFSRP or peptide (e.g., by recombinant expression in vitro) and assessing the activity of the encoded portion of the TFSRP or peptide.

Biologically active portions of a TFSRP are encompassed by the present invention and include peptides comprising amino acid sequences derived from the amino acid sequence of a TFSRP, e.g., an amino acid sequence of SEQ ID NO:17, SEQ ID NO:18, SEQ ID NO:19, SEQ ID NO:20, SEQ ID NO:21, SEQ ID NO:22, SEQ ID NO:23 or SEQ ID NO:24, or the amino acid sequence of a protein homologous to a TFSRP, which include fewer amino acids than a full length TFSRP or the full length protein which is homologous to a TFSRP, and exhibit at least one activity of a TFSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a TFSRP. Moreover, other biologically active portions in which other regions of the protein are deleted, can be prepared by recombinant techniques and evaluated for one or more of the activities described herein. Preferably, the biologically active portions of a TFSRP include one or more selected domains/motifs or portions thereof having biological activity.

The invention also provides TFSRP chimeric or fusion proteins. As used herein, a TFSRP "chimeric protein" or "fusion protein" comprises a TFSRP polypeptide operatively linked to a non-TFSRP polypeptide. A TFSRP polypeptide refers to a polypeptide having an amino acid sequence corresponding to a TFSRP, whereas a non-TFSRP polypeptide refers to a polypeptide having an amino acid sequence corresponding to a protein which is not substantially homologous to the TFSRP, e.g., a protein that is different from the TFSRP and is derived from the same or a different organism. Within the fusion protein, the term "operatively linked" is intended to indicate that the TFSRP polypeptide and the non-TFSRP polypeptide are fused to each other so that both sequences fulfill the proposed function attributed to the sequence used. The non-TFSRP polypeptide can be fused to the N-terminus or C-terminus of the TFSRP polypeptide. For example, in one embodiment, the fusion protein is a GST-TFSRP fusion protein in which the TFSRP sequences are fused to the C-terminus of the GST sequences. Such fusion proteins can facilitate the purification of recombinant TFSRPs. In another embodiment, the fusion protein is a TFSRP containing a heterologous signal sequence at its N-terminus. In certain host cells (e.g., mammalian host cells), expression and/or secretion of a TFSRP can be increased through use of a heterologous signal sequence.

Preferably, a TFSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A TFSRP encoding nucleic acid can be cloned into such an expression vector such that the fusion moiety is linked in-frame to the TFSRP.

In addition to fragments and fusion proteins of the TFSRPs described herein, the present invention includes homologs and analogs of naturally occurring TFSRPs and TFSRP encoding nucleic acids in a plant. "Homologs" are defined herein as two nucleic acids or proteins that have similar, or "homologous", nucleotide or amino acid sequences, respectively. Homologs include allelic variants, orthologs, paralogs, agonists and antagonists of TFSRPs as defined hereafter. The term "homolog" further encompasses nucleic acid molecules that differ from one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16 (and portions thereof) due to degeneracy of the genetic code and thus encode the same TFSRP as that encoded by the nucleotide sequences shown in SEQ ID NO:9, SEQ ID NO:10, SEQ ID NO:11, SEQ ID NO:12, SEQ ID NO:13, SEQ ID NO:14, SEQ ID NO:15 or SEQ ID NO:16. As used herein a "naturally occurring" TFSRP refers to a TFSRP amino acid sequence that occurs in nature. Preferably, a naturally occurring TFSRP comprises an amino acid sequence selected from the group consisting of SEQ ID NO:17, SEQ ID NO:18, SEQ ID NO:19, SEQ ID NO:20, SEQ ID NO:21, SEQ ID NO:22, SEQ ID NO:23 and SEQ ID NO:24.

An agonist of the TFSRP can retain substantially the same, or a subset, of the biological activities of the TFSRP. An antagonist of the TFSRP can inhibit one or more of the activities of the naturally occurring form of the TFSRP. For example, the TFSRP antagonist can competitively bind to a downstream or upstream member of the cell membrane component metabolic cascade that includes the TFSRP, or bind to a TFSRP that mediates transport of compounds across such membranes, thereby preventing translocation from taking place.

Nucleic acid molecules corresponding to natural allelic variants and analogs, orthologs and paralogs of a TFSRP cDNA can be isolated based on their identity to the *Physcomitrella patens* TFSRP nucleic acids described herein using TFSRP cDNAs, or a portion thereof, as a hybridization probe according to standard hybridization techniques under stringent hybridization conditions. In an alternative embodiment, homologs of the TFSRP can be identified by screening combinatorial libraries of mutants, e.g., truncation mutants, of the TFSRP for TFSRP agonist or antagonist activity. In one embodiment, a variegated library of TFSRP variants is generated by combinatorial mutagenesis at the nucleic acid level and is encoded by a variegated gene library. A variegated library of TFSRP variants can be produced by, for example, enzymatically ligating a mixture of synthetic oligonucleotides into gene sequences such that a degenerate set of potential TFSRP sequences is expressible as individual polypeptides, or alternatively, as a set of larger fusion proteins (e.g., for phage display) containing the set of TFSRP sequences therein. There are a variety of methods that can be used to produce libraries of potential TFSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential TFSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the TFSRP coding regions can be used to generate a variegated population of TFSRP fragments for screening and subsequent selection of homologs of a TFSRP. In one embodiment, a library of coding sequence fragments can be generated by treating a double stranded PCR fragment of a TFSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the TFSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TFSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify TFSRP homologs (Arkin and Yourvan, 1992 PNAS 89:7811-7815; Delgrave et al., 1993 Protein Engineering 6(3):327-331). In another embodiment, cell based assays can be exploited to analyze a variegated TFSRP library, using methods well known in the art. The present invention further provides a method of identifying a novel TFSRP, comprising (a) raising a specific antibody response to a TFSRP, or a fragment thereof, as described above; (b) screening putative TFSRP material with the antibody, wherein specific binding of the antibody to the material indicates the presence of a potentially novel TFSRP; and (c) analyzing the bound material in comparison to known TFSRP, to determine its novelty.

To determine the percent homology of two amino acid sequences (e.g., one of the sequences of SEQ ID NO:17, SEQ ID NO:18, SEQ ID NO:19, SEQ ID NO:20, SEQ ID NO:21, SEQ ID NO:22, SEQ ID NO:23 and SEQ ID NO:24 and a mutant form thereof), the sequences are aligned for optimal comparison purposes (e.g., gaps can be introduced in the sequence of one protein or nucleic acid for optimal alignment with the other protein or nucleic acid). The amino acid residues at corresponding amino acid positions are then compared. When a position in one sequence (e.g., one of the sequences of SEQ ID NO:17, SEQ ID NO:18, SEQ ID NO:19, SEQ ID NO:20, SEQ ID NO:21, SEQ ID NO:22, SEQ ID NO:23 and SEQ ID NO:24) is occupied by the same amino acid residue at the corresponding position in the other sequence (e.g., a mutant form of the sequence selected from the polypeptide of SEQ ID NO:17, SEQ ID NO:18, SEQ ID NO:19, SEQ ID NO:20, SEQ ID NO:21, SEQ ID NO:22, SEQ ID NO:23 and SEQ ID NO:24), then the molecules are homologous at that position (i.e., as used herein amino acid or nucleic acid "homology" is equivalent to amino acid or nucleic acid "identity"). The same type of comparison can be made between two nucleic acid sequences.

The percent homology between the two sequences is a function of the number of identical positions shared by the sequences (i.e., % homology=numbers of identical positions/total numbers of positions×100). Preferably, the amino acid sequences included in the present invention are at least about 50-60%, preferably at least about 60-70%, and more preferably at least about 70-80%, 80-90%, 90-95%, and most preferably at least about 96%, 97%, 98%, 99% or more homologous to an entire amino acid sequence shown in SEQ ID NO:17, SEQ ID NO:18, SEQ ID NO:19, SEQ ID NO:20, SEQ ID NO:21, SEQ ID NO:22, SEQ ID NO:23 or SEQ ID NO:24. In yet another embodiment, at least about 50-60%, preferably at least about 60-70%, and more preferably at least about 70-80%, 80-90%, 90-95%, and most preferably at least about 96%, 97%, 98%, 99% or more homologous to an entire amino acid sequence encoded by a nucleic acid sequence shown in SEQ ID NO:9, SEQ ID NO:10, SEQ ID NO:11, SEQ ID NO:12, SEQ ID NO:13, SEQ ID NO:14, SEQ ID NO:15 or SEQ ID NO:16. In other embodiments, the preferable length of sequence comparison for proteins is at least 15 amino acid residues, more preferably at least 25 amino acid residues, and most preferably at least 35 amino acid residues.

In another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:9, SEQ ID NO:10, SEQ ID NO:11, SEQ ID NO:12, SEQ ID NO:13, SEQ ID NO:14, SEQ ID NO:15 or SEQ ID NO:16, or a portion thereof. The preferable length of sequence comparison for nucleic acids is at least 75 nucleotides, more preferably at least 100 nucleotides and most preferably the entire coding region.

It is also preferable that the homologous nucleic acid molecule of the invention encodes a protein or portion thereof which includes an amino acid sequence which is sufficiently homologous to an amino acid sequence of SEQ ID NO:17, SEQ ID NO:18, SEQ ID NO:19, SEQ ID NO:20, SEQ ID NO:21, SEQ ID NO:22, SEQ ID NO:23 or SEQ ID NO:24 such that the protein or portion thereof maintains the same or a similar function as the amino acid sequence to which it is compared. Functions of the TFSRP amino acid sequences of the present invention include the ability to participate in a stress tolerance response in a plant, or more particularly, to participate in the transcription of a protein involved in a stress tolerance response in a *Physcomitrella patens* plant. Examples of such activities are described in Table 1.

In addition to the above described methods, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873-5877). Such an algorithm is incorporated into the NBLAST and XBLAST programs of Altschul, et al. (1990 J. Mol. Biol. 215:403-410).

BLAST nucleic acid searches can be performed with the NBLAST program, score=100, wordlength=12 to obtain nucleic acid sequences homologous to the TFSRP nucleic acid molecules of the invention. Additionally, BLAST protein searches can be performed with the XBLAST program, score=50, wordlength=3 to obtain amino acid sequences homologous to TFSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the TFSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

Finally, homology between nucleic acid sequences can also be determined using hybridization techniques known to those of skill in the art. Accordingly, an isolated nucleic acid molecule of the invention comprises a nucleotide sequence which hybridizes, e.g., under stringent conditions, to one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16, or a portion thereof. More particularly, an isolated nucleic acid molecule of the invention is at least 15 nucleotides in length and hybridizes under stringent conditions to the nucleic acid molecule comprising a nucleotide sequence of SEQ ID NO:9, SEQ ID NO:10, SEQ ID NO:11, SEQ ID NO:12, SEQ ID NO:13, SEQ ID NO:14, SEQ ID NO:15 or SEQ ID NO:16. In other embodiments, the nucleic acid is at least 30, 50, 100, 250 or more nucleotides in length.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1-6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of SEQ ID NO:9, SEQ ID NO:10, SEQ ID NO:1, SEQ ID NO:12, SEQ ID NO:13, SEQ ID NO:14, SEQ ID NO:15 or SEQ ID NO:16 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Physcomitrella patens* TFSRP.

Using the above-described methods, and others known to those of skill in the art, one of ordinary skill in the art can isolate homologs of the TFSRPs comprising amino acid sequences shown in SEQ ID NO:17, SEQ ID NO:18, SEQ ID NO:19, SEQ ID NO:20, SEQ ID NO:21, SEQ ID NO:22, SEQ ID NO:23 or SEQ ID NO:24 and the TFSRP nucleic acids comprising the nucleotide sequences shown in SEQ ID NO:9, SEQ ID NO:10, SEQ ID NO:11, SEQ ID NO:12, SEQ ID NO:13, SEQ ID NO:14, SEQ ID NO:15 or SEQ ID NO:16. One subset of these homologs are allelic variants. As used herein, the term "allelic variant" refers to a nucleotide sequence containing polymorphisms that lead to changes in the amino acid sequences of a TFSRP and that exist within a natural population (e.g., a plant species or variety). Such natural allelic variations can typically result in 1-5% variance in a TFSRP nucleic acid. Allelic variants can be identified by sequencing the nucleic acid sequence of interest in a number of different plants, which can be readily carried out by using hybridization probes to identify the same TFSRP genetic locus in those plants. Any and all such nucleic acid variations and resulting amino acid polymorphisms or variations in a TFSRP that are the result of natural allelic variation and that do not alter the functional activity of a TFSRP, are intended to be within the scope of the invention.

Moreover, nucleic acid molecules encoding TFSRPs from the same or other species such as TFSRP analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631-637). Analogs, orthologs and paralogs of a naturally occurring TFSRP can differ from the naturally occurring TFSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 90%, and most preferably 95%, 96%, 97%, 98% or even 99% identity or homology with all or part of a naturally occurring TFSRP amino acid sequence and will exhibit a function similar to a TFSRP. Orthologs of the present invention are also preferably capable of participating in the stress response in plants. In one embodiment, the TFSRP orthologs maintain the ability to participate in the metabolism of compounds necessary for the construction of cellular membranes in *Physcomitrella patens*, or in the transport of molecules across these membranes.

In addition to naturally-occurring variants of a TFSRP sequence that may exist in the population, the skilled artisan will further appreciate that changes can be introduced by mutation into a nucleotide sequence, such as the sequences of SEQ ID NO:9, SEQ ID NO:10, SEQ ID NO:11, SEQ ID NO:12, SEQ ID NO:13, SEQ ID NO:14, SEQ ID NO:15 or SEQ ID NO:16, thereby leading to changes in the amino acid sequence of the encoded TFSRP, without altering the functional ability of the TFSRP. For example, nucleotide substitutions leading to amino acid substitutions at "non-essential" amino acid residues can be made in the proteins including a sequence of SEQ ID NO:9, SEQ ID NO:10, SEQ ID NO:11, SEQ ID NO:12, SEQ ID NO:13, SEQ ID NO:14, SEQ ID NO:15 or SEQ ID NO:16. A "non-essential" amino acid residue is a residue that can be altered from the wild-type sequence of one of the TFSRPs without altering the activity of said TFSRP, whereas an "essential" amino acid residue is required for TFSRP activity. Other amino acid residues, however, (e.g., those that are not conserved or only semi-conserved in the domain having TFSRP activity) may not be essential for activity and thus are likely to be amenable to alteration without altering TFSRP activity.

Accordingly, another aspect of the invention pertains to nucleic acid molecules encoding TFSRPs that contain changes in amino acid residues that are not essential for TFSRP activity. Such TFSRPs differ in amino acid sequence from a sequence contained in SEQ ID NO:17, SEQ ID NO:18, SEQ ID NO:19, SEQ ID NO:20, SEQ ID NO:21, SEQ ID NO:22, SEQ ID NO:23 or SEQ ID NO:24, yet retain at least one of the TFSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:17, SEQ ID NO:18, SEQ ID NO:19, SEQ ID NO:20, SEQ ID NO:21, SEQ ID NO:22, SEQ ID NO:23 or SEQ ID NO:24. Preferably, the protein encoded by the nucleic acid molecule is at least about 50-60% homologous to one of the sequences of SEQ ID NO:17, SEQ ID NO:18, SEQ ID NO:19, SEQ ID NO:20, SEQ ID NO:21, SEQ ID NO:22, SEQ ID NO:23 or SEQ ID NO:24, more preferably at least about 60-70% homologous to one of the sequences of SEQ ID NO:17, SEQ ID NO:18, SEQ ID NO:19, SEQ ID NO:20, SEQ ID NO:21, SEQ ID NO:22, SEQ ID NO:23 or SEQ ID NO:24, even more preferably at least about 70-80%, 80-90%, 90-95% homologous to one of the sequences of SEQ ID NO:17, SEQ ID NO:18, SEQ ID NO:19, SEQ ID NO:20, SEQ ID NO:21, SEQ ID NO:22, SEQ ID NO:23 or SEQ ID NO:24, and most preferably at least about 96%, 97%, 98%, or 99% homologous to one of the sequences of SEQ ID NO:17, SEQ ID NO:18, SEQ ID NO:19, SEQ ID NO:20, SEQ ID NO:21, SEQ ID NO:22, SEQ ID NO:23 or SEQ ID NO:24. The preferred TFSRP homologs of the present invention are preferably capable of participating in the stress tolerance response in a plant, or more particularly, participating in the transcription of a protein involved in a stress tolerance response in a *Physcomitrella patens* plant, or have one or more activities set forth in Table 1.

An isolated nucleic acid molecule encoding a TFSRP homologous to a protein sequence of SEQ ID NO:17, SEQ ID NO:18, SEQ ID NO:19, SEQ ID NO:20, SEQ ID NO:21, SEQ ID NO:22, SEQ ID NO:23 or SEQ ID NO:24 can be created by introducing one or more nucleotide substitutions, additions or deletions into a nucleotide sequence of SEQ ID NO:9, SEQ ID NO:10, SEQ ID NO:11, SEQ ID NO:12, SEQ ID NO:13, SEQ ID NO:14, SEQ ID NO:15 or SEQ ID NO:16 such that one or more amino acid substitutions, additions or deletions are introduced into the encoded protein. Mutations can be introduced into one of the sequences of SEQ ID NO:9, SEQ ID NO:10, SEQ ID NO:11, SEQ ID NO:12, SEQ ID NO:13, SEQ ID NO:14, SEQ ID NO:15 and SEQ ID NO:16 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a TFSRP is preferably replaced with another amino acid residue from the same side chain family. Alternatively, in another embodiment, mutations can be introduced randomly along all or part of a TFSRP coding sequence, such as by saturation mutagenesis, and the resultant mutants can be screened for a TFSRP activity described herein to identify mutants that retain TFSRP activity. Following mutagenesis of one of the sequences of SEQ ID NO:9, SEQ ID NO:10, SEQ ID NO:11, SEQ ID NO:12, SEQ ID NO:13, SEQ ID NO:14, SEQ ID NO:15 and SEQ ID NO:16, the encoded protein can be expressed recombinantly and the activity of the protein can be determined by analyzing the stress tolerance of a plant expressing the protein as described in Example 7.

In addition to the nucleic acid molecules encoding the TFSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire TFSRP coding strand, or to only a portion thereof. In one embodiment, an antisense nucleic acid molecule is antisense to a "coding region" of the coding strand of a nucleotide sequence encoding a TFSRP. The term "coding region" refers to the region of the nucleotide sequence comprising codons that are translated into amino acid residues (e.g., the entire coding region of , , , comprises nucleotides 1 to . . . ). In another embodiment, the antisense nucleic acid molecule is antisense to a "noncoding region" of the coding strand of a nucleotide sequence encoding a TFSRP. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16, or a portion thereof. A nucleic acid molecule that is complementary to one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16 is one which is sufficiently complementary to one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16 such that it can hybridize to one of the nucleotide sequences shown in SEQ ID NO:9, SEQ ID NO:10, SEQ ID NO:11, SEQ ID NO:12, SEQ ID NO:13, SEQ ID NO:14, SEQ ID NO:15 and SEQ ID NO:16, thereby forming a stable duplex.

Given the coding strand sequences encoding the TFSRPs disclosed herein (e.g., the sequences set forth in SEQ ID NO:9, SEQ ID NO:10, SEQ ID NO:11, SEQ ID NO:12, SEQ ID NO:13, SEQ ID NO:14, SEQ ID NO:15 and SEQ ID NO:16), antisense nucleic acids of the invention can be designed according to the rules of Watson and Crick base pairing. The antisense nucleic acid molecule can be complementary to the entire coding region of TFSRP mRNA, but more preferably is an oligonucleotide which is antisense to only a portion of the coding or noncoding region of TFSRP mRNA. For example, the antisense oligonucleotide can be complementary to the region surrounding the translation start site of TFSRP mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a TFSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585-591) can be used to catalytically cleave TFSRP mRNA transcripts to thereby inhibit translation of TFSRP mRNA. A ribozyme having specificity for a TFSRP-encoding nucleic acid can be designed based upon the nucleotide sequence of a TFSRP cDNA, as disclosed herein (i.e., SEQ ID NO:9, SEQ ID NO:10, SEQ ID NO:11, SEQ ID NO:12, SEQ ID NO:13, SEQ ID NO:14, SEQ ID NO:15 or SEQ ID NO:16) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in a TFSRP-encoding mRNA. See, e.g., Cech et al. U.S. Pat. No. 4,987,071 and Cech et al. U.S. Pat. No. 5,116,742. Alternatively, TFSRP mRNA can be used to select a catalytic RNA having a specific ribonuclease activity from a pool of RNA molecules. See, e.g., Bartel, D. and Szostak, J. W., 1993 Science 261:1411-1418.

Alternatively, TFSRP gene expression can be inhibited by targeting nucleotide sequences complementary to the regulatory region of a TFSRP nucleotide sequence (e.g., a TFSRP promoter and/or enhancer) to form triple helical structures that prevent transcription of a TFSRP gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12):807-15.

In addition to the TFSRP nucleic acids and proteins described above, the present invention encompasses these nucleic acids and proteins attached to a moiety. These moieties include, but are not limited to, detection moieties, hybridization moieties, purification moieties, delivery moieties, reaction moieties, binding moieties, and the like. One typical group of nucleic acids attached to a moiety are probes and primers. The probe/primer typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:9, SEQ ID NO:10, SEQ ID NO:11, SEQ ID NO:12, SEQ ID NO:13, SEQ ID NO:14, SEQ ID NO:15 and SEQ ID NO:16, an anti-sense sequence of one of the sequences set forth in SEQ ID NO:9, SEQ ID NO:10, SEQ ID NO:11, SEQ ID NO:12, SEQ ID NO:13, SEQ ID NO:14, SEQ ID NO:15 and SEQ ID NO:16, or naturally occurring mutants thereof. Primers based on a nucleotide sequence of SEQ ID NO:9, SEQ ID NO:10, SEQ ID NO:11, SEQ ID NO:12, SEQ ID NO:13, SEQ ID NO:14, SEQ ID NO:15 or SEQ ID NO:16 can be used in PCR reactions to clone TFSRP homologs. Probes based on the TFSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a TFSRP, such as by measuring a level of a TFSRP-encoding nucleic acid, in a sample of cells, e.g., detecting TFSRP mRNA levels or determining whether a genomic TFSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a TFSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., TFSRPs, mutant forms of TFSRPs, fusion proteins, etc.).

The recombinant expression vectors of the invention can be designed for expression of TFSRPs in prokaryotic or eukaryotic cells. For example, TFSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583-586); Plant Molecular Biology and Biotechnology, C Press, Boca Raton, Fla., chapter 6/7, S. 71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, *Gene Expression Technology. Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of a recombinant protein; 2) to increase the solubility of a recombinant protein; and 3) to aid in the purification of a recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the TFSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant TFSRP unfused to GST can be recovered by cleavage of the fusion protein with thrombin.

Examples of suitable inducible non-fusion *E. coli* expression vectors include pTrc (Amann et al., 1988 Gene 69:301-315) and pET 11d (Studier et al., *Gene Expression Technology. Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111-2118). Such alteration of nucleic acid sequences of the invention can be carried out by standard DNA synthesis techniques.

In another embodiment, the TFSRP expression vector is a yeast expression vector. Examples of vectors for expression in yeast *S. cerevisiae* include pYepSec1 (Baldari, et al., 1987 Embo J. 6:229-234), pMFa (Kurjan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

Alternatively, the TFSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell Biol. 3:2156-2165) and the pVL series (Lucklow and Summers, 1989 Virology 170:31-39).

In yet another embodiment, a TFSRP nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268-277), lymphoid-specific promoters (Calame and Eaton, 1988 Adv. Immunol. 43:235-275), in particular promoters of T cell receptors (Winoto and Baltimore, 1989 EMBO J. 8:729-733) and immunoglobulins (Banerji et al., 1983 Cell 33:729-740; Queen and Baltimore, 1983 Cell 33:741-748), neuron-specific promoters (e.g., the neurofilament promoter; Byrne and Ruddle, 1989 *PNAS* 86:5473-5477), pancreas-specific promoters (Edlund et al., 1985 Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990 Science 249:374-379) and the fetoprotein promoter (Campes and Tilghman, 1989 Genes Dev. 3:537-546).

In another embodiment, the TFSRPs of the invention may be expressed in unicellular plant cells (such as algae) (see Falciatore et al., 1999 Marine Biotechnology 1(3):239-251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195-1197; and Bevan, M. W., 1984 Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693-8711).

Plant gene expression has to be operably linked to an appropriate promoter conferring gene expression in a timely, cell or tissue specific manner. Preferred are promoters driving constitutive expression (Benfey et al., 1989 EMBO J. 8:2195-2202) like those derived from plant viruses like the 35S CAMV (Franck et al., 1980 Cell 21:285-294), the 19S CaMV (see also U.S. Pat. No. 5,352,605 and PCT Application No. WO 8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Also, suitable promoters responding to biotic or abiotic stress conditions are those such as the pathogen inducible PRP1-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331-340).

Especially preferred are those promoters that confer gene expression in specific tissues and organs, such as guard cells and the root hair cells. Suitable promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce-4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, maize zein gene, oat glutelin gene, *Sorghum* kasirin-gene and rye secalin gene).

Also especially suited are promoters that confer plastid-specific gene expression since plastids are the compartment where lipid biosynthesis occurs. Suitable promoters are the viral RNA-polymerase promoter described in PCT Application No. WO 95/16783 and PCT Application No. WO 97/06250 and the clpP-promoter from *Arabidopsis* described in PCT Application No. WO 99/46394.

The invention further provides a recombinant expression vector comprising a TFSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a TFSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a TFSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crop plants are also preferred target plants for a genetic engineering as one further embodiment of the present invention.

In particular, the invention provides a method of producing a transgenic plant with a TFSRP coding nucleic acid, wherein expression of the nucleic acid(s) in the plant results in increased tolerance to environmental stress as compared to a wild type variety of the plant comprising: (a) transforming a plant cell with an expression vector comprising a TFSRP nucleic acid, and (b) generating from the plant cell a transgenic plant with a increased tolerance to environmental stress as compared to a wild type variety of the plant. The invention also provides a method of increasing expression of a gene of interest within a host cell as compared to a wild type variety of the host cell, wherein the gene of interest is transcribed in response to a TFSRP, comprising: (a) transforming the host cell with an expression vector comprising a TFSRP coding nucleic acid, and (b) expressing the TFSRP within the host cell, thereby increasing the expression of the gene transcribed in response to the TFSRP, as compared to a wild type variety of the host cell.

For such plant transformation, binary vectors such as pBinAR can be used (Höfgen and Willmitzer, 1990 Plant Science 66:221-230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4 (15):285-423). The signal peptide is cloned 5-prime in frame to the cDNA to archive subcellular localization of the fusion protein. Additionally, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of an mRNA which encodes a polypeptide. Alternatively, the RNA can be an antisense RNA for use in affecting subsequent expression of the same or another gene or genes.

Alternate methods of transfection include the direct transfer of DNA into developing flowers via electroporation or *Agrobacterium* mediated gene transfer. *Agrobacterium* mediated plant transformation can be performed using for example the GV3101(pMP90) (Koncz and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993.—360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using for example a technique described in European Patent No. 0424 047, U.S. Pat. No. 5,322,783, European Patent No. 0397 687, U.S. Pat. Nos. 5,376,543 or 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a TFSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a TFSRP gene into which a deletion, addition or substitution has been introduced to thereby alter, e.g., functionally disrupt, the TFSRP gene. Preferably, the TFSRP gene is a *Physcomitrella patens* TFSRP gene, but it can be a homolog from a related plant or even from a mammalian, yeast, or insect source. In a preferred embodiment, the vector is designed such that, upon homologous recombination, the endogenous TFSRP gene is functionally disrupted (i.e., no longer encodes a functional protein; also referred to as a knock-out vector). Alternatively, the vector can be designed such that, upon homologous recombination, the endogenous TFSRP gene is mutated or otherwise altered but still encodes a functional protein (e.g., the upstream regulatory region can be altered to thereby alter the expression of the endogenous TFSRP). To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the TFSRP gene is flanked at its 5' and 3' ends by an additional nucleic acid molecule of the TFSRP gene to allow for homologous recombination to occur between the exogenous TFSRP gene carried by the vector and an endogenous TFSRP gene, in a microorganism or plant. The additional flanking TFSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368-4373 for cDNA based recombination in *Physcomitrella patens*). The vector is introduced into a microorganism or plant cell (e.g., via polyethylene glycol mediated DNA), and cells in which the introduced TFSRP gene has homologously recombined with the endogenous TFSRP gene are selected using art-known techniques.

In another embodiment, recombinant microorganisms can be produced that contain selected systems which allow for regulated expression of the introduced gene. For example, inclusion of a TFSRP gene on a vector placing it under control of the lac operon permits expression of the TFSRP gene only in the presence of IPTG. Such regulatory systems are well known in the art.

A host cell of the invention, such as a prokaryotic or eukaryotic host cell in culture, can be used to produce (i.e., express) a TFSRP. Accordingly, the invention further provides methods for producing TFSRPs using the host cells of the invention. In one embodiment, the method comprises culturing the host cell of invention (into which a recombinant expression vector encoding a TFSRP has been introduced, or into which genome has been introduced a gene encoding a wild-type or altered TFSRP) in a suitable medium until TFSRP is produced. In another embodiment, the method further comprises isolating TFSRPs from the medium or the host cell.

Another aspect of the invention pertains to isolated TFSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of TFSRP in which the protein is separated from some of the cellular components of the cells in which it is naturally or recombinantly produced. In one embodiment, the language "substantially free of cellular material" includes preparations of a TFSRP having less than about 30% (by dry weight) of non-TFSRP material (also referred to herein as a "contaminating protein"), more preferably less than about 20% of non-TFSRP material, still more preferably less than about 10% of non-TFSRP material, and most preferably less than about 5% non-TFSRP material.

When the TFSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of TFSRP in which the protein is separated from chemical precursors or other chemicals that are involved in the synthesis of the protein. In one embodiment, the language "substantially free of chemical precursors or other chemicals" includes preparations of a TFSRP having less than about 30% (by dry weight) of chemical precursors or non-TFSRP chemicals, more preferably less than about 20% chemical precursors or non-TFSRP chemicals, still more preferably less than about 10% chemical precursors or non-TFSRP chemicals, and most preferably less than about 5% chemical precursors or non-TFSRP chemicals. In preferred embodiments, isolated proteins, or biologically active portions thereof, lack contaminating proteins from the same organism from which the TFSRP is derived. Typically, such proteins are produced by recombinant expression of, for example, a *Physcomitrella patens* TFSRP in plants other than Physcomitrellapatens or microorganisms such as *C. glutamicum*, ciliates, algae or fungi.

The nucleic acid molecules, proteins, protein homologs, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of TFSRP regions required for function; modulation of a TFSRP activity; modulation of the metabolism of one or more cell functions; modulation of the trans-membrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The TFSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a TFSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example.

In particular, the present invention describes using the expression of APS-2, ZF-2, ZF-3, ZF-4, ZF-5, MYB-1, CABF-3 and SFL-1 of *Physcomitrella patens* to engineer drought-tolerant, salt-tolerant and/or cold-tolerant plants. This strategy has herein been demonstrated for *Arabidopsis thaliana*, Rapeseed/Canola, soybeans, coin and wheat but its application is not restricted to these plants. Accordingly, the invention provides a transgenic plant containing a TFSRP selected from APS-2 (SEQ ID NO:17), ZF-2 (SEQ ID NO:18), ZF-3 (SEQ ID NO:19), ZF-4 (SEQ ID NO:20), ZF-5 (SEQ ID NO:21), MYB-1 (SEQ ID NO:22), CABF-3 (SEQ ID NO:23) and SFL-1 (SEQ ID NO:24), wherein the environmental stress is drought, increased salt or decreased or increased temperature. In preferred embodiments, the environmental stress is drought or decreased temperature The present invention also provides methods of modifying stress tolerance of a plant comprising, modifying the expression of a TFSRP in the plant. The invention provides that this method can be performed such that the stress tolerance is either increased or decreased. In particular, the present invention provides methods of producing a transgenic plant having an increased tolerance to environmental stress as compared to a wild type variety of the plant comprising increasing expression of a TFSRP in a plant.

The methods of increasing expression of TFSRPs can be used wherein the plant is either transgenic or not transgenic. In cases when the plant is transgenic, the plant can be transformed with a vector containing any of the above described TFSRP coding nucleic acids, or the plant can be transformed with a promoter that directs expression of native TFSRP in the plant, for example. The invention provides that such a promoter can be tissue specific. Furthermore, such a promoter can be developmentally regulated. Alternatively, non-transgenic plants can have native TFSRP expression modified by inducing a native promoter.

The expression of APS-2 (SEQ ID NO:17), ZF-2 (SEQ ID NO:18), ZF-3 (SEQ ID NO:19), ZF-4 (SEQ ID NO:20), ZF-5 (SEQ ID NO:21), MYB-1 (SEQ ID NO:22), CABF-3 (SEQ ID NO:23) or SFL-1 (SEQ ID NO:24) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the APS-2 (SEQ ID NO:17), ZF-2 (SEQ ID NO:18), ZF-3 (SEQ ID NO:19), ZF-4 (SEQ ID NO:20), ZF-5 (SEQ ID NO:21), MYB-1 (SEQ ID NO:22), CABF-3 (SEQ ID NO:23) or SFL-1 (SEQ ID NO:24) homologs in the target plant as well as from its promoter. Zinc-finger-containing recombinant transcription factors are engineered to specifically interact with the APS-2 (SEQ ID NO:17), ZF-2 (SEQ ID NO:18), ZF-3 (SEQ ID NO:19), ZF-4 (SEQ ID NO:20), ZF-5 (SEQ ID NO:21), MYB-1 (SEQ ID NO:22), CABF-3 (SEQ ID NO:23) or SFL-1 (SEQ ID NO:24) homolog and transcription of the corresponding gene is activated.

In addition to introducing the TFSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those fragments that bind the protein may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The TFSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein that are essential for the functioning of the enzyme. This type of determination is of value for protein engineering studies and may give an indication of what the protein can tolerate in terms of mutagenesis without losing function.

Manipulation of the TFSRP nucleic acid molecules of the invention may result in the production of TFSRPs having functional differences from the wild-type TFSRPs. These proteins may be improved in efficiency or activity, may be present in greater numbers in the cell than is usual, or may be decreased in efficiency or activity.

There are a number of mechanisms by which the alteration of a TFSRP of the invention may directly affect stress response and/or stress tolerance. In the case of plants expressing TFSRPs, increased transport can lead to improved salt and/or solute partitioning within the plant tissue and organs. By either increasing the number or the activity of transporter molecules which exportionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as Arahidopsis, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more TFSRP genes of the invention may also result in TFSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more TFSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for TFSRPs resulting in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated TFSRP nucleic acid and protein molecules such that the stress tolerance is improved.

The present invention also provides antibodies that specifically bind to a TFSRP, or a portion thereof, as encoded by a nucleic acid described herein. Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refer to a binding reaction that is determinative of the presence of the protein in a heterogeneous population of proteins and other biologics. Thus, under designated immunoassay conditions, the specified antibodies bound to a particular protein do not bind in a significant amount to other proteins present in the sample. Selective binding of an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia.

After fertilization, the diploid sporophyte with a short seta and the spore capsule resulted, in which the meiospores matured.

Culturing was carried out in a climatic chamber at an air temperature of 25° C. and light intensity of 55 micromol $s^{-1}m^{-2}$ (white light; Philips T L 65 W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of H₂O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)⁺ RNA were isolated. The total RNA was obtained from wild-type 9 day old protonemata following the GTC-method (Reski et al. 1994, Mol. Gen. Genet., 244:352-359). The Poly(A)+ RNA was isolated using Dyna Beads® (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands.) Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'     SEQ ID NO: 25

5'-CTAAAGGGAACAAAAGCTG-3'    SEQ ID NO: 26

5'-TGTAAAACGACGGCCAGT-3'     SEQ ID NO: 27
```

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpgde. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63-98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10; PREDATOR: High-accuracy secondary structure prediction from single and multiple sequences. Frishman, D. and Argos, P. (1997) 75% accuracy in protein secondary structure prediction. Proteins, 27:329-335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182-192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221-226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921; BLIMPS: Similarity searches against a database of ungapped blocks. J. C. Wallace and Henikoff S., (1992); PATMAT: A searching and extraction program for sequence, pattern and block queries and databases, CABIOS 8:249-254. Written by Bill Alford.

Example 5

Identification of *Physcomitrella patens* ORFs Corresponding to APS-2, ZF-2, ZF-3, ZF-4, ZF-5, MYB-1, CABF-3 and SFL-1

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: APS-2 (SEQ ID NO:1), ZF-2 (SEQ ID NO:2), ZF-3 (SEQ ID NO:3), ZF-4 (SEQ ID NO:4), ZF-5 (SEQ ID NO:5), MYB-1 (SEQ ID NO:6), CABF-3 (SEQ ID NO:7) and SFL-1 (SEQ ID NO:8).

TABLE 1

| Name | Functional categories | Function | Sequence code | ORF position |
|---|---|---|---|---|
| PpAPS-2 | CBF/Transcription factor | AP2 domain containing protein RAP2.11 | c_pp001007077f | 592-92 |
| PpZF-2 | Transcription factor | zinc finger protein | c_pp004033187r | 1688-765 |
| PpZF-3 | Transcription factor | BRCA1-associated RING domain protein | c_pp004042321r | 1-500 |
| PpZF-4 | Transcription factor | zinc finger protein ZNF216 | c_pp004059097r | 701-1216 |
| PpZF-5 | Transcription factor | transcription factor-like protein | c_pp004046041r | 1-675 |
| PpMYB-1 | Transcription factor | transcription factor | s_pp002016030r | 2-505 |
| PpCABF-3 | Transcription factor | transcription factor, CCAAT-binding, chain A | c_pp004040113r | 221-535 |
| PpSFL-1 | Transcription factor | transcription initiation factor sigma A | s_pp001105041r | 598-158 |

TABLE 2

Degree of amino acid identity and similarity of PpCBF-3 and other homologous proteins (Pairwise comparison program was used: gap penalty: 10; gap extension penalty: 0.1; score matrix: blosum62)

| Swiss-Prot # | O23310 | P25209 | Q9LFI3 | O23633 | Q9ZQC3 |
|---|---|---|---|---|---|
| Protein name | CCAAT-binding transcription factor subunit a | CCAAT-binding transcription factor subunit a | Transcription factor NF-Y, CCAAT-binding-like protein | Transcription factor | Putative CCAAT-binding transcription factor |
| Species | *Arabidopsis thaliana* (Mouse-ear cress) | *Zea mays* (Maize) | *Arabidopsis thaliana* (Mouse-ear cress) | *Arabidopsis thaliana* (Mouse-ear cress) | *Arabidopsis thaliana* (Mouse-ear cress) |
| Identity % | 53% | 49% | 42% | 43% | 62% |
| Similarity % | 58% | 58% | 53% | 51% | 66% |

TABLE 3

Degree of amino acid identity and similarity of PpZF-2 and other homologous proteins (Pairwise comparison program was used: gap penalty: 10; gap extension penalty: 0.1; score matrix: blosum62)

| Swiss-Prot # | O24008 | Q9LUR1 | Q9XF63 | Q9XF64 | Q9LZJ6 |
|---|---|---|---|---|---|
| Protein name | Zinc finger protein | Ring zinc finger protein-like | Ring-h2 zinc finger protein (atl3) | Ring-h2 zinc finger protein atl5 | Ring-h2 zinc finger protein atl5 |
| Species | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 27% | 26% | 25% | 20% | 19% |
| Similarity % | 35% | 35% | 34% | 28% | 28% |

TABLE 4

Degree of amino acid identity and similarity of PpZF-3 and other homologous proteins (Pairwise comparison program was used: gap penalty: 10; gap extension penalty: 0.1; score matrix: blosum62)

| Swiss-Prot # | Q9SMX5 | O04097 | Q9UQR3 | Q9XZQ1 | Q9XZQ2 |
|---|---|---|---|---|---|
| Protein name | Gcn4-complementing protein (gcp1) | Brca1-associated ring domain protein isolog | Centaurin beta2 | Centaurin beta 1a | Centaurin beta 1b |
| Species | Arabidopsis thaliana (Mouse-ear cress) | Arabidopsis thaliana (Mouse-ear cress) | Homo sapiens (Human) | Caenorhabditis elegans | Caenorhabditis elegans |
| Identity % | 41% | 37% | 24% | 21% | 22% |
| Similarity % | 54% | 49% | 32% | 31% | 34% |

TABLE 5

Degree of amino acid identity and similarity of PpZF-4 and other homologous proteins (Pairwise comparison program was used: gap penalty: 10; gap extension penalty: 0.1; score matrix: blosum62)

| Swiss-Prot # | Q9LXI5 | O88878 | O76080 | Q9ZNU9 | O96038 |
|---|---|---|---|---|---|
| Protein name | Zinc finger-like protein | Zinc finger protein znf216 | Zinc finger protein 216 | Putative zinc finger protein | Pem-6 |
| Species | Arabidopsis thaliana (Mouse-ear cress) | Mus musculus (Mouse) | Homo sapiens (Human) | Arabidopsis thaliana (Mouse-ear cress) | Ciona savignyi |
| Identity % | 39% | 34% | 34% | 35% | 32% |
| Similarity % | 53% | 45% | 45% | 50% | 49% |

TABLE 6

Degree of amino acid identity and similarity of PpZF-5 and other homologous proteins (Pairwise comparison program was used: gap penalty: 10; gap extension penalty: 0.1; score matrix: blosum62)

| Swiss-Prot # | Q9SZW1 | Q9ZTR9 | Q9SYQ6 | Q9ZTX9 | O23661 |
|---|---|---|---|---|---|
| Protein name | Transcription factor-like protein | Auxin response factor 8 | Auxin response factor 7 | Auxin response factor 4 | Ettin protein |
| Species | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 39% | 23% | 25% | 25% | 25% |
| Similarity % | 50% | 32% | 33% | 32% | 35% |

TABLE 7

Degree of amino acid identity and similarity of PpAPS-2 and other homologous proteins (Pairwise comparison program was used: gap penalty: 10; gap extension penalty: 0.1; score matrix: blosum62)

| Swiss-Prot # | Q9SJR0 | O22174 | O04682 | Q9SW63 | Q9SGJ6 |
|---|---|---|---|---|---|
| Protein name | Putative AP2 domain transcription factor | Putative AP2 domain containing protein | Pathogenesis-related genes transcriptional activator pti6 | Tiny-like protein | Transcription factor dreb1a |
| Species | Arabidopsis thaliana (Mouse-ear cress) | Arabidopsis thaliana (Mouse-ear cress) | Lycopersicon esculentum (Tomato) | Arabidopsis thaliana (Mouse-ear cress) | Arabidopsis thaliana (Mouse-ear cress) |
| Identity % | 18% | 19% | 15% | 15% | 16% |
| Similarity % | 23% | 29% | 20% | 25% | 24% |

TABLE 8

Degree of amino acid identity and similarity of PpSFL-1 and other homologous proteins (Pairwise comparison program was used: gap penalty: 10; gap extension penalty: 0.1; score matrix: blosum62)

| Swiss-Prot # | Q59965 | Q9L4T2 | O22455 | O22056 | Q9MTH3 |
|---|---|---|---|---|---|
| Protein name | RNA polymerase sigma factor | RNA polymerase sigma factor | RNA polymerase sigma factor | RNA polymerase sigma factor | RNA polymerase sigma factor |
| Species | Synechococcus sp. | Nostoc punctiforme | Arabidopsis thaliana (Mouse-ear cress) | Arabidopsis thaliana (Mouse-ear cress) | Sinapis alba (White mustard) |
| Identity % | 49% | 49% | 32% | 42% | 30% |
| Similarity % | 62% | 61% | 44% | 59% | 42% |

TABLE 9

Degree of amino acid identity and similarity of PpMYB-1 and other homologous proteins (Pairwise comparison program was used: gap penalty: 10; gap extension penalty: 0.1; score matrix: blosum62).

| Swiss-Prot # | Q9LLM9 | Q9ZTD9 | Q9SEZ4 | Q9ZTD7 | Q9MBG3 |
|---|---|---|---|---|---|
| Protein name | Myb-like protein | Putative transcription factor | Putative Myb family transcription factor | Putative transcription factor | Myb transcription factor-like protein |
| Species | Oryza sativa (Rice) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 37% | 37% | 32% | 36% | 29% |
| Similarity % | 47% | 44% | 38% | 44% | 37% |

Example 6

Cloning of the Full-Length *Physcomitrella patens* cDNA Encoding for APS-2, ZF-2, ZF-3, ZF-4, ZF-5, MYB-1, CABF-3 and SFL-1

Full-length clones corresponding to CABF-3 (SEQ ID NO:15) and APS-2 (SEQ ID NO:9) were obtained by performing polymerase chain reaction (PCR) with gene-specific primers (see Table 10) and the original EST as the template since they were full-length. The conditions for the reaction are described below under "Full-length Amplification."

To isolate the clones encoding for PpZF-2, PpZF-3, PpZF-4, PpZF-5 PpAPS-1, PpSFL-1 and PpMYB-1 from *Physcomitrella patens*, cDNA libraries were created with SMART RACE cDNA Amplification kit (Clontech Laboratories) following the manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points above. RNA was then pulled and used for isolation.

5' RACE Protocol

The EST sequences PpZF-2 (SEQ ID NO:2), PpZF-3 (SEQ ID NO:3), PpZF-4 (SEQ ID NO:4), PpZF-5 (SEQ ID NO:5), PpMYB-1 (SEQ ID NO:6) and PpSFL-1 (SEQ ID NO:8) identified from the database search as described in Example 5 were used to design oligos for RACE (see Table 1). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions.

The sequences obtained from the RACE reactions contained the 5' end of the full-length coding regions of for PpZF-2, PpZF-3, PpZF-4, PpZF-5 PpAPS-1, PpSFL-1 and PpMYB-1 and were used to design oligos for full-length cloning of the respective genes (see below under "Full-length Amplification).

Full-length Amplification

Full-length clones corresponding to PpCABF-3 (SEQ ID NO:15) and PpAPS-2 (SEQ ID NO:9) were obtained by performing polymerase chain reaction (PCR) with gene-specific primers (see Table 10) and the original EST as the template. The conditions for the reaction were standard conditions with PWO DNA polymerase (Roche). PCR was performed according to standard conditions and to manufacture's protocols (Sambrook et al. 1989. Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C.

Full-length clones for PpZF-2 (SEQ ID NO:10), PpZF-3 (SEQ ID NO:11), PpZF-4 (SEQ ID NO:12), PpZF-5 (SEQ ID NO:13), PpMYB-1 (SEQ ID NO:14) and PpSFL-1 (SEQ ID NO:16) and were isolated by repeating the RACE method but using the gene-specific primers as given in Table 10.

The amplified fragments were extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

TABLE 10

| Gene | Sites in the final product | Isolation Method | Primers Race | Primer Full-length PCR |
|---|---|---|---|---|
| PpCABF-3 | XmaI/ SacI | PCR of original EST clone | N/A | RC405 (SEQ ID NO: 28) ATCCCGGGCAGCGAGCACACAGCTAGCAACTCTT RC406 (SEQ ID NO: 29) GCGAGCTCACTCCCTCACGCGGTTGACAATCT |
| PpZF-2 | XmaI/ SacI | 5' RACE and RT-PCR for Full-length clone | RC189 (SEQ ID NO: 30) TGGCGGCCTC GGTCTTCTTC TCAGT | RC606 (SEQ ID NO: 31) ATCCCGGGAGGAAGCT GTCAGGGAAGAGATGG A RC607 (SEQ ID NO: 32) GCGAGCTCTGGCCGTA AAATCAGTTGTGGCGC TT |
| PpZF-3 | XmaI/ EcoRV | 5' RACE and RT-PCR for Full-length clone | RC188 (SEQ ID NO: 33) CAGCGAAGCCC AATCGGGATCA GCA | RC604 (SEQ ID NO: 34) ATCCCGGGAGGAGGAC TTGCGGAATGCAAATC RC605 (SEQ ID NO: 35) GCGATATCCACCTGCTT CCACTCTCTACTTATG |
| PpZF-4 | XmaI/ SacI | 5' RACE and RT-PCR for Full-length clone | RC185 (SEQ ID NO: 36) GACACCCGAT TGAGCCGGCA AGACG | RC564 (SEQ ID NO: 37) ATCCCGGGCACCAGTC CCGCTTAGTGTGTGT RC565 (SEQ ID NO: 38) GCGAGCTCTTGATGCG ACTCGCTCTCTCGAT |
| PpZF-5 | XmaI/ SacI | 5' RACE and RT-PCR for Full-length clone | RC187 (SEQ ID NO: 39) CGGCGAGTGCA GCAGCTTCTAG AACG | RC612 (SEQ ID NO: 40) ATCCCGGGTATCGATC TGGAGCCCGTTGCAA RC613 (SEQ ID NO: 41) GCGAGCTCCTCCAAAG GACTTTGAAATATAGC |
| PpAPS-2 | EcoRV/ SacI | PCR of original EST clone | N/A | RC395 (SEQ ID NO: 42) GATATCGGAAGAAGAA TCCAAGGGAATGCGGT T RC396 (SEQ ID NO: 43) GCGAGCTCTATGCTTCC GTGGGAGGAGCTTCAC |
| PpSFL-1 | XmaI/ SacI | 5' RACE and RT-PCR for Full-length clone | RC172 (SEQ ID NO: 44) CCGGCTGGGTT GCCTCAGCTTG CGCA RC538 (SEQ ID NO: 45) CGCTCCATCGA ACCTGGTGCCT TTGC | RC884 (SEQ ID NO: 46) ATCCCGGGCTCGGAAG GACTGTGCATTGTCGA RC885 (SEQ ID NO: 47) GCGAGCTCGCAGCAGA AGAAATCCACTTCTGG T |
| PpMYB-1 | SmaI/ SmaI | 5' RACE and RT-PCR for Full-length clone | RC170 (SEQ ID NO: 48) GGGTGCCGGTT GATGCGAGGGT CCAG | RC701 (SEQ ID NO: 49) ATCCCGGGCTGTTGTGT ACAGTCTGTGGA RC702 (SEQ ID NO: 50) ATCCCGGGCTCACGGA GTAAAGGCCGTACCTT |

Example 7

Engineering Stress-tolerant *Arabidopsis* Plants by Over-expressing the Genes APS-2, ZF-2, ZF-3, ZF-4, ZF-5, MYB-1, CABF-3 and SFL-1

Binary Vector Construction:

The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator. Primers for PCR amplification of the NPTII gene were designed as follows:

5'NPT-Pst:
(SEQ ID NO: 51)
GCG-CTG-CAG-ATT-TCA-TTT-GGA-GAG-GAC-ACG

3'NPT-Fse:
(SEQ ID NO: 52)
CGC-GGC-CGG-CCT-CAG-AAG-AAC-TCG-TCA-AGA-AGG-CG.

The 0.9 kilobase NPTII gene was amplified via PCR from pCambia 2301 plasmid DNA (94° C. for 60 seconds, {94° C. for 60 seconds, 61° C. (−0.1° C. per cycle) for 60 seconds, 72° C. for 2 minutes)×25 cycles, 72° C. for 10 minutes on Biometra T-Gradient machine), and purified via the Qiaquick PCR Extraction kit (Qiagen) as per manufacturer's instructions. The PCR DNA was then subcloned into the pCR-BluntII TOPO vector (Invitrogen) pursuant to the manufacturer's instructions (NPT-Topo construct). These ligations were transformed into Top10 cells (Invitrogen) and grown on LB plates with 50 µg/ml kanamycin sulfate overnight at 37° C. Colonies were then used to inoculate 2 ml LB media with 50 µg/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using Vector NTI software revealed no PCR errors present in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation was then transformed into Top10 cells (Invitrogen) under standard conditions, creating pBPSsc019 construct. Colonies were selected on LB plates with 50 µg/ml kanamycin sulfate and grown overnight at 37° C. These colonies were then used to inoculate 2 ml LB media with 50 µg/ml kanamycin sulfate and grown overnight at 37° C. Plasmid DNA was recovered using the Qiaprep Spin Miniprep kit (Qiagen) following the manufacturer's instructions.

The pBPSSC019 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the *Arabidopsis* Actin2 promoter with internal intron, the NPTII gene and the OCS3 terminator.

The pBPSJH001 vector was digested with SpeI and ApaI (Roche) and blunt-end filled with Klenow enzyme and 0.1 mM dNTPs (Roche) according to manufacture's instructions. This produced a 10.1 kilobase vector fragment minus the Gentamycin cassette, which was recirculated by self-ligating with T4 DNA Ligase (Roche), and transformed into Top10 cells (Invitrogen) via standard conditions. Transformed cells were selected for on LB agar containing 50 µg/ml kanamycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacture's instructions. The recirculated plasmid was then digested with KpnI (Roche) and extracted from agarose gel via the Qiaex II DNA Extraction kit (Qiagen) as per manufacturer's instructions.

The Act-NPT Kpn-cut insert and the Kpn-cut pBPSJH001 recirculated vector were then ligated together using T4 DNA Ligase (Roche) and transformed into Top10 cells (Invitrogen) as per manufacturers' instructions. The resulting construct, pBPSsc022, now contained the Super Promoter, the GUS gene, the NOS terminator, and the Act-NPT cassette. Transformed cells were selected for on LB agar containing 50 µg/ml kanamycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPSsc022 plasmid DNA was further propagated and recovered using the Plasmid Midiprep Kit (Qiagen) following the manufacturer's instructions.

Subcloning of APS-2, ZF-2, ZF-3, ZF-4, ZF-5, MYB-1, CABF-3 and SFL-1 into the Binary Vector The fragments containing the different *Physcomitrella patens* transcription factors were subcloned from the recombinant PCR2.1 TOPO vectors by double digestion with restriction enzymes (see Table 11) according to manufacturer's instructions. The subsequence fragment was excised from agarose gel with a QIAquick Gel Extraction Kit (QIAgen) according to manufacture's instructions and ligated into the binary vectors pBPSSC022, cleaved with XmaI and Ecl136II and dephosphorylated prior to ligation. The resulting recombinant pBPSSC022 contained the corresponding transcription factor in the sense orientation under the constitutive super promoter.

TABLE 11

Listed are the names of the various constructs of the *Physcomitrella patens* transcription factors used for plant transformation

| Gene | Enzymes used to generate gene fragment | Enzymes used to restrict pBPSJH001 | Binary Vector Construct |
|---|---|---|---|
| PpCABF-3 | XmaI/SacI | XmaI/SacI | pBPSLVM185 |
| PpZF-2 | XmaI/SacI | XmaI/SacI | pBPSSY008 |
| PpZF-3 | XmaI/EcoRV | XmaI/Ecl136 | pBPSSY017 |
| PpZF-4 | XmaI/SacI | XmaI/SacI | pBPSLVM163 |
| PpZF-5 | XmaI/SacI | XmaI/SacI | pBPSERG006 |
| PpAPS-2 | EcoRV/SacI | SmaI/SacI | pBPSLVM161 |
| PpSFL-1 | XmaI/SacI | XmaI/SacI | pBPSERG001 |
| PpMYB-1 | SmaI/SmaI | SmaI/Ecl136 | pBPSERG020 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194-1199; Bent et al. 1994, Science 265:1856-1860).

Screening of Transformed Plants

T1 seeds were sterilized according to standard protocols (Xiong et al. 1999, Plant Molecular Biology Reporter 17: 159-170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino]ethansulfonic acid (MES) (Sigma-Aldrich), 50 µg/ml kanamycin (Sigma-Aldrich), 500 µg/ml carbenicillan (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1}m^{-2}$ (white light; Philips TL 65 W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 g/L MES (Sigma-Aldrich), and 2 µg/ml benomyl (Sigma-Aldrich) and allowed to recover for five-seven days.

Drought Tolerance Screening

T1 seedlings were transferred to dry, sterile filter paper in a petri dish and allowed to desiccate for two hours at 80% RH (relative humidity) in a Percival Growth CU3615, micromole $s^{-1}m^{-2}$ (white light; Philips TL 65 W/25 fluorescent tube). The RH was then decreased to 60% and the seedlings were desiccated further for eight hours. Seedlings were then removed and placed on ½ MS 0.6% agar plates supplemented with 2 µg/ml benomyl (Sigma-Aldrich) and 0.5 g/L MES ((Sigma-Aldrich) and scored after five days.

Under drought stress conditions, PpCABF-3 over-expressing *Arabidopsis thaliana* plants showed a 70% (39 survivors from 56 stressed plants) survival rate to the stress screening; PpZF-2, 98% (39 survivors from 40 stressed plants); PpZF-3, 94% (59 survivors from 63 stressed plants); PpZF-4, 94% (16 survivors from 17 stressed plants); PpZF-5, 80% (8 survivors from 10 stressed plants); PpAPS-2 65% (13 survivors from 20 stressed plants); and PpMYB-1 80% (8 survivors from 10 stressed plants); whereas the untransformed control a 28% (16 survivors from 57 stressed plants) survival rate. It is noteworthy that the analyses of these transgenic lines were performed with T1 plants, and therefore, the results will be better when a homozygous, strong expresser is found.

TABLE 12

Summary of the drought stress tests

Drought Stress Test

| Gene Name | Number of survivors | Total number of plants | Percentage of survivors |
|---|---|---|---|
| PpCABF-3 | 39 | 56 | 70% |
| PpZF-2 | 39 | 40 | 98% |
| PpZF-3 | 59 | 63 | 94% |
| PpZF-4 | 16 | 17 | 94% |
| PpZF-5 | 8 | 10 | 80% |
| PpAPS-2 | 13 | 20 | 65% |
| PpMYB-1 | 8 | 10 | 80% |
| Control | 16 | 57 | 28% |

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing 1° C./hour. The seedlings were then incubated at −5.0° C. for 24 hours and then allowed to thaw at 5° C. for 12 hours. The water was poured off and the seedlings were scored after 5 days.

Under freezing stress conditions, PpCABF-3 over-expressing *Arabidopsis thaliana* plants showed an 98% (41 survivors from 42 stressed plants) survival rate to the stress screening; PpZF-2, 86% (19 survivors from 22 stressed plants); and PpZF-3, 74% (14 survivors from 19 stressed plants); whereas the untransformed control a 28% (16 survivors from 57 stressed plants) survival rate. It is noteworthy that the analyses of these transgenic lines were performed with T1 plants, and therefore, the results will be better when a homozygous, strong expresser is found.

TABLE 13

Summary of the freezing stress tests

Freezing Stress Test

| Gene Name | Number of survivors | Total number of plants | Percentage of survivors |
|---|---|---|---|
| PpCABF-3 | 41 | 42 | 98% |
| PpZF-2 | 19 | 22 | 86% |
| PpZF-3 | 14 | 19 | 74% |
| Control | 1 | 48 | 2% |

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days.

The transgenic plants are screened for their improved salt tolerance demonstrating that transgene expression confers salt tolerance.

Example 8

Detection of the APS-2, ZF-2, ZF-3, ZF-4, ZF-5, MYB-1, CABF-3 and SFL-1 Transgenes in the Transgenic *Arabidopsis* Lines One leaf from a wild type and a transgenic *Arabidopsis* plant was homogenized in 250 µl Hexadecyltrimethyl ammonium bromide (CTAB) buffer (2% CTAB, 1.4 M NaCl, 8 mM EDTA and 20 mM Tris pH 8.0) and 1 µl β-mercaptoethanol. The samples were incubated at 60-65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol, dried, and resuspended in 20 µl TE. 4 µl of above suspension was used in a 20 µl PCR reaction using Taq DNA polymerase (Roche Molecular Biochemicals) according to the manufacturer's instructions. Binary vector plasmid with each gene cloned in was used as positive control, and the wild type C24 genomic DNA was used as negative control in the PCR reactions. 10 µl PCR reaction was analyzed on 0.8% agarose/ethidium bromide gel. The PCR program used was as follows: 30 cycles of 1 minute at 94° C., 1 minute at 62° C. and 4 minutes at 70° C., followed by 10 minutes at 72° C. The following primer was used as 5' primer: Bfwd: 5'GCTGACACGCCAAGCCTCGCTAGTC3'. (SEQ ID NO:53) The gene-specific primers and the size of the amplified bands (Gene Product Size) are listed below.

```
PpCABF-3
Primer:  RC406:   GCGAGCTCACTCCCTCACGCGGTTGACAATCT
Gene      800 bp  (SEQ ID NO: 54)
Product
Size:

PpZF-2
Primer:  RC607:   GCGAGCTCTGGCCGTAAAATCAGTTGTGGCGCTT
Gene     1800 bp  (SEQ ID NO: 55)
Product
Size:

PpZF-3
Primer:  RC605:   GCGATATCCACCTGCTTCCACTCTCTACTTATG
Gene     2000 bp  (SEQ ID NO: 56)
Product
Size:

PpZF-4
Primer:  RC565:   GCGAGCTCTTGATGCGACTCGCTCTCTCGAT
Gene      800 bp  (SEQ ID NO: 57)
Product
Size:

PpZF-5
Primer:  RC613:   GCGAGCTCCTCCAAAGGACTTTGAAATATAGC
Gene     2700 bp  (SEQ ID NO: 58)
Product
Size:

PpAPS-2
Primer:  RC396:   GCGAGCTCTATGCTTCCGTGGGAGGAGCTTCAC
Gene     1000 bp  (SEQ ID NO: 59)
Product
Size:

PpSFL-1
Primer:  RC885:   GCGAGCTCGCAGCAGAAGAAATCCACTTCTGGT
Gene     1700 bp  (SEQ ID NO: 60)
Product
Size:

PpMYB-1
Primer:  RC702:   ATCCCGGGCTCACGGAGTAAAGGCCGTACCTT
Gene     2400 bp  (SEQ ID NO: 61)
Product
Size:
```

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis thaliana* control which could be amplified by this method.

Example 9

Detection of the APS-2, ZF-2, ZF-3, ZF-4, ZF-5, MYB-1, CABF-3 and SFL-1 Transgene mRNA in Transgenic *Arabidopsis* Lines Transgene expression was detected using RT-PCR. Total RNA was isolated from stress-treated plants using a procedure adapted from (Verwoerd et al., 1989 NAR 17:2362). Leaf samples (50-100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water.

To remove contaminating DNA from the samples, each was treated with RNase-free DNase (Roche) according to the manufacturer's recommendations. cDNA was synthesized from total RNA using the $1^{st}$ Strand cDNA synthesis kit (Boehringer Mannheim) following manufacturer's recommendations. PCR amplification of a gene-specific fragment from the synthesized cDNA was performed using Taq DNA polymerase (Roche) and gene-specific primers (see Table 4 for primers) in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad). Expression of the transgenes was detected in the T1 transgenic line.

These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

TABLE 14

Primers used for the amplification of respective transgene mRNA in PCR using RNA isolated from transgenic *Arabidopsis thaliana* plants as template

| Gene | 5' primer | 3' primer |
|---|---|---|
| PpCABF-2 | RC405:<br>(SEQ ID NO: 62)<br>ATCCCGGGCAGCGAGCA<br>CACAGCTAGCAACTCTT | RC406:<br>(SEQ ID NO: 63)<br>GCGAGCTCACTCCCTCAC<br>GCGGTTGACAATCT |

TABLE 14-continued

Primers used for the amplification of respective transgene mRNA in PCR using RNA isolated from transgenic *Arabidopsis thaliana* plants as template

| Gene | 5' primer | 3' primer |
|---|---|---|
| PpZF-2 | RC1191:<br>(SEQ ID NO: 64)<br>GCCCGTTGTGTCGCACGA<br>GTGTGGGA | RC1192:<br>(SEQ ID NO: 65)<br>GCCGCTGGACCAGACCTC<br>GGAATGT |
| PpZF-3 | RC1203:<br>(SEQ ID NO: 66)<br>GAGGCAGTCATGCAATC<br>GACCCCAA | RC1204:<br>(SEQ ID NO: 67)<br>GCGAAGCCCAATCGGGA<br>TCAGCAGCA |
| PpZF-4 | RC564:<br>(SEQ ID NO: 68)<br>ATCCCGGGCACCAGTCCC<br>GCTTAGTGTGTGT | RC565:<br>(SEQ ID NO: 69)<br>GCGAGCTCTTGATGCGAC<br>TCGCTCTCTCGAT |
| PpZF-5 | RC1209:<br>(SEQ ID NO: 70)<br>CGCATCGCATCTGGCG<br>AACTTTGTG | RC1210:<br>(SEQ ID NO: 71)<br>3' primer for EST281<br>at#1368 GC = 58%<br>CGTACCACGATTGCTCTA<br>GCGCACGT |
| PpAPS-1 | RC395:<br>(SEQ ID NO: 72)<br>GCGATATCGGAAGAAGA<br>ATCCAAGGGAATGCGGTT | RC396:<br>(SEQ ID NO: 73)<br>GCGAGCTCTATGCTTCCG<br>TGGGAGGAGCTTCAC |
| PpAPS- | RC405:<br>(SEQ ID NO: 74)<br>ATCCCGGGCAGCGAGCA<br>CACAGCTAGCAACTCTT | RC406:<br>(SEQ ID NO: 75)<br>GCGAGCTCACTCCCTCAC<br>GCGGTTGACAATCT |
| PpSFL-1 | RC1191:<br>(SEQ ID NO: 76)<br>GCCCGTTGTGTCGCACGA<br>GTGTGGGA | RC1192:<br>(SEQ ID NO: 77)<br>GCCGCTGGACCAGACCTC<br>GGAATGT |
| PpMYB-1 | RC1203:<br>(SEQ ID NO: 78)<br>GAGGCAGTCATGCAAT<br>CGACCCCAA | RC1204:<br>(SEQ ID NO: 79)<br>GCGAAGCCCAATCGGG<br>ATCAGCAGCA |

Example 10

Engineering Stress-tolerant Soybean Plants by Over-expressing the APS-2, ZF-2, ZF-3, ZF-4, ZF-5, MYB-1, CABF-3 and SFL-1 Gene The constructs pBPSLVM185, pBPSSY008, pBPSSY017, pBPSLVM163, pBPSERG006, pBPSLVM161, pBPSERG001 and pBPSERG020 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 µmol m$^{-2}$sec$^{-1}$ and 12 hours photoperiod. Once the seedlings produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 µmol m$^{-2}$sec$^{-1}$ light intensity and 12 hours photoperiod for about 80 days.

The transgenic plants are then screened for their improved drought, salt and/or cold tolerance according to the screening method described in Example 7 to demonstrate that transgene expression confers stress tolerance.

Example 11

Engineering Stress-tolerant Rapeseed/Canola Plants by Over-expressing the APS-2, ZF-2, ZF-3, ZF-4, ZF-5, MYB-1, CABF-3 and SFL-1 Genes The constructs pBPSLVM185, pBPSSY008, pBPSSY017, pBPSLVM163, pBPSERG006, pBPSLVM161, pBPSERG001 and pBPSERG020 are used to transform rapeseed/canola as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 to demonstrate that transgene expression confers drought tolerance.

Example 12

Engineering Stress-tolerant Corn Plants by Over-expressing the APS-2, ZF-2, ZF-3, ZF-4, ZF-5, MYB-1, CABF-3 or SFL-1 Genes The constructs pBPSLVM185, pBPSSY008, pBPSSY017, pBPSLVM163, pBPSERG006, pBPSLVM161, pBPSERG001 and pBPSERG020 are used to transform corn as described below.

Transformation of maize (Zea Mays L.) is performed with the method described by Ishida et al. 1996. Nature Biotch 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 to demonstrate that transgene expression confers stress tolerance.

Example 13

Engineering Stress-tolerant Wheat Plants by Over-expressing the APS-2, ZF-2, ZF-3, ZF-4, ZF-5, MYB-1, CABF-3 or SFL-1 Genes The constructs pBPSLVM185, pBPSSY008, pBPSSY017, pBPSLVM163, pBPSERG006, pBPSLVM161, pBPSERG001, pBPSERG020 are used to transform wheat as described below.

Transformation of wheat is performed with the method described by Ishida et al. 1996 Nature Biotch. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 to demonstrate that transgene expression confers drought tolerance.

Example 14

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 μg/ml denatured salmon sperm DNA
0.1% nonfat dried milk During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15

Identification of Homologous Genes by Screening Expression Libraries with Antibodies cDNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257-262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M. (1994) Strategies 7: 32-34. Transfer of mutated DNA molecules into plants is preferably done after selection and testing in microorganisms. Transgenic plants are generated according to various examples within the exemplification of this document.

Example 17

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J*. 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199-234 and 270-322, Springer: Heidelberg (1989).

Example 18

Purification of the Desired Product from Transformed Organisms

Recovery of the desired product from plant material (i.e., *Physcomitrella* patents or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133-140; Malalhova et al., 1996 *Biotekhnologiya* 11:27-32; and Schmidt et al., 1998 *Bioprocess Engineer.* 19:67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

APPENDIX

Nucleotide sequence of the partial APS-2 from
*Physcomitrella patens* (SEQ ID NO: 1)

TCAAGCCACTCATCCGAGCATAGAACATCACAACCCACCTTGATGATCATTCTCT
CAGCCGACCAGCGTCAATTACGCTGCGTATCGCTCTAGCTTGAGGAAGGCACCCT

APPENDIX-continued

```
CGCCCTCTTCGCCGCGGAAGTAGCCCTCTGCTTCACGAGGGCGGCAAAACTCTCC
CAAGGCAGTTCCGGGGGATGGGATATAGCTGCAGCTGCTGTGGGGAATCCTCA
AAATTGTACGGGATCTTCTTCTTTGTGTAGAAGATGCCAACATCGTAGGCCCGGG
CAGCTTCTTCCGGAGTTTCATATGTTCCCAGCCATATCTTACGTTTCTGAGATGTG
GGTCGAATTTCTGTCACCCATTTGTTTAGCTCGGGCCGGTGCCGAACCCCCCTAA
AACTGGTCGTATCGCCAGTGTTGCTAGCAGAAACTTCTTCGGTATCCCATGCCGA
TGGGGCCTTATTTAAATCAATATTCCGAAATTTAAAGGCATTCCGACCGCTAGTG
TCTTTCGCCGCTAACCGCATTCCCTTGGATTCTTCTTCCAAACTAGATTCAGACTT
GCTCTCCTGCCAACTTCTTTTTTCACTTTCGGGGATTCTATTTTAGTCGTTAACTG
CAACGCCTGTTCTTTGACCTTGCCACCACAAGGATCCCACTTCTTTGTTTTGGGCT
TCCCCTGTTCAATAATGCTGGAAATTGTCAAATTCATGAACTACCCAATTGCAAC
CCCTCCCACCGGGATGGATTGATCGCCAAAATTTCGTAGTAACTTAACTTTCATA
CAACAACTTGAGTTCCTTCGCTATTAGGGACACGTGGCAGAAACTTGGACGTGC
AAGCGTATGTACTCATCAGAGTTTGACAGCGCATAAAATCATATAAAAGTCTTG
AAGAAGCGTTGTTTAATTCATGGGTAACCACGAGTTACGCGGAGCGTCGGCAGC
AAGGAGAGGACGACCAGGCGGCAAGAAGATGCGTCGGCAAGAGCTCGTGC
```

Nucleotide sequence of the partial ZF-2 from
*Physcomitrella patens* (SEQ ID NO: 2)

```
TTTTTTTTGGCGAAAATGGGTAAAAATTTCCGTGGCCGTAAAATCAGTTGTGGCG
CTTGCCTTGCAATAAGCTGGTTATCGTAAAATGGCAATTACCTTGATATGTTCAC
TAGGTTCGTGTCAGTGAGATGCCTTGCAGAAGGCGATTTCCCGTTTATTTACAAC
TCTACATGTTACTGAAGCACTGTGGCATTCAATCTCCTAACCTAGAGATGCTTAA
CTGCTTCGTGCATGATCTATATTACATCTTGAGCCTCAGACTGTGGCGTCTTATTG
CACATCTAGCGCTATATATTACACTACGGTACACCATCGGAAGAAGTGAAGAAG
GAATAGCTACTATTTTGCATCTCCAGTGTCAAATGTGATGCTGACCTGACCTAAT
CGGCAGAGACGCAGATCTCCAATGCTCACACTTCACATCCTAAAACGCACTTGC
AGTGTACCCTGCTCTCAATTCCCATTGCAATTCCACATCTGGATCTAAGGGCAT
GCTTTGTGGGCACTAAAGCGCCGATTTCCTCCTCAATGCGAAGGTTGACCTTACT
GAGGAAAGTGCGCATCGTAATCGGCGATGTAGGCTTAGGGATTTCGCCGGGTAA
CACTCAACGCAATCGTGACGTTCGCTAGATAGCTTGGTTGATATCAGGTGCAAAT
CCCACACAAAATCCTTTGCATGGTCGGGCATTTATGTCTACCAGGGAAGTATCAGTT
TTCTTCCAGAATAAAATTTCCACTTTAACAGCACCTGCTCACGAAATCCTCAGGC
ATGTGGTGGTGGTGGACGGGGTGAAGAAGAAG
GCCCGCCCTCGTCAACACCATCTTCTCCAGTTTGGGGCGACACCACACTCTTCCC
TCGGCTCAACAAACGTCGGAAGCTCGCTGAAGCACGCGCCATCGGCGCAAAAC
ATTCGACGAATTGCTGACAGCCGCTGGACCAGACCTCGGAATGTCGATAGTAAC
CTGAAACGGCGCACGAATACTGGACGCCGCCCTCGCTTCTGCACTCCTCCTGCA
CCTGCACTGCTCATCTGCGCATGATTCCCCCAGAATAACACATTGGACGGGATTC
CGGACGGTGTCTCGTAATCTTTATGTTTGCTGCTGATCAACCGCAACGGCCGT
TTCCGACGTACCACTTCGGCGATGATTCTCCCCGCCCTGATCCTCCGCAGTGCGG
GGCAAACTATTGCCTCTTGGGGAACTATTCAACGCCGGCAACTGTCCCCGGCTCC
GTTGGCTCCTCCTGGAAGCTCGCATGGCCGCCATGAACGGCGCTCCTACGTCACC
CATAACGGGCGCTTCCATC
TGAGGAGGCTCGCTTATCTGCATCACGGTGGCGGCCTCGGTCTTCTTCTCAGTTT
CATCAGCTCCCACACTCGTGCGACACAACGGGCATGTCGAGTGCGAGTGCAACC
ACATGTCAATACAATCCAAGTGGAAACTATGGTCACACTTCGGCAACGTGCGGC
CTTTCTCACCCAACTCAAATTCTTCCAAACAAACCGCGCACTCGAACCCACGCTT
TGCCCTCTCACCGTCGAATTCGAAAGTGGGCAGAGCTTCAATAACAGCCCGCTCA
AGCCCCACTGCCTGCGTCACCGGAGTAGCGTTCACAGGGACAGTGTAACGGCGT
CTTCGCCATGATAACGTACGCAAGGTGCCATCGCTTGCGACGATCTGGTGC
```

Nucleotide sequence of the partial ZF-3 from
*Physcomitrella patens* (SEQ ID NO: 3)

```
GCACCAGCGCTTTTAAACAATCAAATATCTGAGCAGGTTGATGGCGAAGATTCA
GATGTATCAAGAAGTGGCGCTAGTGATCAATCTGGGCATGAAAGACCCCTTGAC
GTTTTACGCAAGGTGAAAGGAAATGATGCTTGTGCCGACTGCGGTGCTGCTGATC
CCGATTGGGCTTCGCTGAATCTTGGGATTCTTCTGTGTATTGAGTGCTCAGGAGT
ACACAGAAACATGAGCGTTCAGATTTCTAAGGTCCGTTCGTTGACGTTAGATGTC
AAAGTTTGGGAGCCTTCTGTAATGAGCTATTTTCAATCTGTCGGAAACTCCTACG
CTAATTCTATATGGGAAGAGCTTTTGAATCCCAAGTCCTCAGAGGAGTCAAGTGA
GAGAAACGTTAATGACGAGGGACAATGGGCGTTTTAAGTGCTAGCAGAGCAAG
GCCAAGACCTAGAGACCCCATACCTATCAAAGAAAGATTTATCAATGCAAAGTA
TGTGGAGAAAA
```

Nucleotide sequence of the partial ZF-4 from
*Physcomitrella patens* (SEQ ID NO: 4)

```
GCACGAGCTGCCCCATTCGAGCCCACTCGCACGAGAAGATACGAGCCGCGCTTT
GGCCGAGTGGTCGTAAGTAGAAGTAAAGGTCCGCGGCCGCTGCGGTCTGTGAAA
TTCTCTCGCACGGAGAGAAGCGTGTTCTGCTGGTTTCTTCGCACAGAGACTTCTC
CTGCACCTTTTCTTCTTCCTCTACATCGTCTCCTGCGACGACTACATTGTGTGGGA
GCAGTGGCAACCTTCCTGGCCACCCCGGGCTTCCTCTCAGTCAGTGGCTCACGTC
TCCCAGCTAGGCCTCCCATCGCGTCTTGCCGGCTCAATGGGTGTCTTGCTCTGTT
TTTTAACCTCTCTCCCTTCCGGCCCTCTTATTCCTCTCCAGTCACTTCCGCCGGAT
CGCGACTTTTGTACCCATTTGGGGGTTGGGTGTTATAAGTTTGCCCTCAGGGTGT
GAGTTGCTTTGTGTGTCTTTTGTAGTAGTACTTTGCTTGITGGGTGCGGAAGGGA
```

APPENDIX-continued

```
ACCTTTGAGAAGTCGACCCATTCTCTAGTTTTGCACCAGTCCCGCTTAGTGTGTGT
GTCATTAGTGTTGGTTGCAAGTCTGAAGCCTTGAGCGAGATTTGCAGGATTTTCT
CATACGCTTCTGATTAGGAAAGATACATCCTTATTAGTCTGTTAAAGATGGCCAC
CGAGCGTGTGTCTCAGGAGACGACCTCGCAGGCCCCTGAGGGTCCAGTTATGTG
CAAGAACCTTTGCGGCTTCTTCGGCAGCCAAGCTACCATGGGGTTGTGCTGAAG
TGCTACCGAGAGACAGTCATGCAGCGAAGATGACGGCTYfAGCTGAGCAAGCCA
CTCAGGCTGCTCAGGCGACATCTGCCACAGCTGCTGCTGTTCAGCCCCCCGCTCC
TGTACATGAGACCAAGCTCACATGCGAGGTTGAGAGAACAATGATTGTGCCGCA
TCAATCTTCCAGCTATCAACAAGACCTGGTTACCCCCGCTGCAGCTGCCCCTCAG
GCAGTGAAGTCCTCTATCGCAGCTCCCTCTAGACCCGAGCCCAATCGATGCGGAT
CTTGCAGGAAGCGTGTTGGATTGACAGGATTTAAGTGTCGCTGTGGCAACCTCTA
CTGCGCTTTACATCGGTACTCGGACAAACACACTTGCACATATGACTACAAAGCC
GCAGGGCAGGAAGCGATTGCGAAAGCTAATCCTCTTGTCGTGGCCGAGAAGGTT
GTCAAGTTTTGATGAGCATCCGTTAAGCTTTTCTGCCGACGATTTAGGCTTCATA
CATTGAGTAACTCTACATCTTTCTTCTTTATCGAGAGAGCGAGTCGCATCA
AGATGAAGTCGAGGGGTGCGCGTCGGTTTTGGGGAGAGGGGATTTCTTTCCCCTT
TCCCCCCTTGGCGGCATCGTGTTTTATGTGTACAGAAGTAGGTTAGGACAAGATA
GAATCATATGCCAGATCAATTGATAGTCCTCTTTAAGGAGGACACTTATTACACA
ATAAAAAATCCTGGGTAATGCATGCCTTGATTGTGTTGTTTTTTCCTCGTGC
```

Nucleotide sequence of the partial ZF-5 from
*Physcomitrella patens* (SEQ ID NO: 5)

```
GCGTGGGGCGTCTACACTAGTTTATCCCCGGGCTGAGGAATTCGGCACCAGATTT
GTCAATCAAAAGAAGTTAGTTGCGGGTGATGCTATTGTATTTCTTCGCATCGCAT
CTGGCGAACTTTGTGTCGGCGTGCGCCGTTCAATGAGGGGTGTCAGCAACGGAG
AATCCTCATCTTGGCACTCCTCAATCAGTAATGCTTCAACGATTCGGCCATCTCG
ATGGGAGGTGAAGGGCACAGAAAGTTTCTCGGACTTTTTAGGTGGCGTTGGTGA
TAATGGGTACGCACTGAATAGCTCAATTCGGTCTGAAAACCAGGGCTCTCCAAC
AACGAGTAGCTTTGCACGGGACCGTGCTCGTGTTACTGCGAAGTCCGTTCTAGAA
GCTGCTGCACTCGCCGTCTCCGGTGAACGTTTTGAGGTTGTGTATTATCCTCGTGC
TAGCACAGCTGAGTTCTGTGTCAAAGCTGGGCTTGTTAAACGTGCGCTAGAGCA
ATCGTGGTACGCTGGAATGCGCTTCAAAATGGCATTTGAAACTGAAGACTCCTCG
AGGATAAGCTGGTTTATGGGAACTATTGCTGCTGTTCAAGCAGCAGATCCAGTAA
CTTGTGGCCTAGTTCTCCATGGCGGGTCTGCAGGTCACCTTGGGATGAGCGGACC
TATTGCAGGAGTGATCGTGTAGCCATGGAGTA
```

Nucleotide sequence of the partial MYB-1 from
*Physcomitrella patens* (SEQ ID NO: 6)

```
GCACCAGTGTTCCCTTTCATATGCTCAGCATGTCCGCCAATGAGCGCGCCTGTTG
TGTACAGTCTGTGGAGAGCTGTAGAAAATTCAATTCCGATTTCAAAATATCCAGC
GACGATGACACGGAACATGGGAGTTTGGAGGACGACATGAAGGAGTTGAACGA
AGACATGGAAATTCCCTTAGGTCGAGATGGCGAGGGTATGCAGTCAAAGCAGTG
CCCGCGCGGCCACTGGCGTCCAGCGGAAGACGACAAGCTGCGAGAACTAGTGTC
CCAGTTTGGACCTCAAAACTGGAATCTCATAGCAGAGAAACTTCAGGGTCGATC
AGGGAAAAGCTGCAGGCTACGGTGGTTCAATCAGCTGGACCCTCGCATCAACCG
GCACCCATTCTCGGAAGAAGAGGAAGAGCGGCTGCTTATAGCACACAAGCGCTA
CGGCAACAAGTGGGCATTGATCGCGCGCCTCTTTCCGGGCCGCACAGACAACGC
GGTGAAGAATCACTGGCCC
```

Nucleotide sequence of the partial CABF-3 from
*Physcomitrella patens* (SEQ ID NO: 7)

```
GCACCAGGTCTTCGACTTTGCTTCAGCACGCGCGCGTTGTGGTCGATCTCTCGCT
GGAGCAACAGGTTGTCTTGTCGCTGCCATTGCTAAAGCCATTCTTACTTCTAGCA
CTTCTCGGAGGTTATTGATTTCTCGCAAATTGCTCTTCCACCTGCCCTCTTTCGTG
AGGGAGTTCGAAGCTGAAAAGTAATGAGCTGAAGATTAAGGTCTTTTACGAGTG
AACAGCGAGCACACAGCTAGCAACTCTTTCGGAGAATACTCCAGGCGAAATTGG
TCGGATGGCCGATAGCTACGGTCACAACGCAGGTTCACCAGAGAGCAGCCCGCA
TTCTGATAACGAGTCCGGGGGTCATTACCGAGACCAGGATGCTTCTGTACGGGA
ACAGGATCGGTTCCTGCCCATCGCGAACGTGAGCCGAATCATGAAGAAGGCGTT
GCCGTCTAATGCAAAAATTTCGAAGGACGCGAAAGAGACTGTGCAGGAGTGTGT
GTCCGAGTTCATCAGCTTCATCACTGGTGAGGCGTCAGATAAGTGC
```

Nucleotide sequence of the partial SFL-1 from
*Physcomitrella patens* (SEQ ID NO: 8)

```
GCACGAGTTTTCTTGTGTCAAAGCAGCAGAAGAAATCCACTTCTGGTAGTATTCA
AACATAAAAGAATGGAAACTTATGTAACAGTCTACTTTCTGATCGAAACATTACC
AAATGCCTTTTTCCTGGTTTGGTAGGTACTATCAATCAGCAGCAATTAAATAGCG
TCAGATTTCACATCTAAGTACTCTCGTAGAATGCTGTTCCGGCTGGGTTGCCTCA
GCTTGCGCATCGCTTTTGCCTCAATTTGTCTTATCCTTTCCCGAGTAACTTTAAAG
ATTTGACCTATTTCTTCTAAAGTCTTGGACCGCCCATCGTCCAATCCAAAACGCA
GTCTTAGCACCTCCCTCTCTCTTGGGTTCAATGTGCGTAGAACGCCCTCTATATCT
TGTCGCATCAATTGCTTTACGATTGCGTCCTCAGGTGAATCCACATCTGTGTCTGC
GACAAGTTCCCCAAGTGTANTGTCCCCATCTTTGCCAATGGGCCGCTCCATCGAA
CCTGGTGCCTTTGCTGATTTCACTACAGATTTCAGTTTCTCAACAGTCAAGCCCAC
TAGCTCAGCCACTTCCTCGTTACGTGCTTCCCGCCCATGCTCCTG
```

APPENDIX-continued

Nucleotide sequence of the full-length APS-2 from
*Physcomitrella patens* (SEQ ID NO: 9)

GCGATATCGGAAGAAGAACCAAGGGAATGCGGTTAGCGGCGAAAGACACTAGC
GGTCGGAATGCCTTTAAATTTCGGAATATTGATTTAAATAAGGCCCCATCGGCAT
GGGATACCGAAGAAGTTTCTGCTAGCAACACTGGCGATACGACCAGTTTTAGGG
GGGTTCGGCACCGGCCCGAGCTAAACAAATGGGTGACAGAAATTCGACCCACAT
CTCAGAAACGTAAGATATGGCTGGGAACATATGAAACTCCGGAAGAAGCTGCCC
GGGCCTACGATGTTGGCATCTTCTACACAAAGAAGAAGATCCCGTACAATTTTGA
GGATTCCCCACAGCAGCTGCAGCTATATCCCATCCCCCCGGAACTGCCTTGGGAG
AGTTTTGCCGCCCTCGTGAAGCAGAGGGCTACTTCCGCGGCGAAGAGGGCGAGG
GTGCCTTCCTCAAGCTAGAGCGATACGCAGCGTAATTGACGCTGGTCGGCTGAG
AGAATGATCATCAAGGTGGGTTGTGATGTTCTATGCTCGGATGAGTGGCTTGAAG
GGTTCTGGTTCCAACCATGAGAGCATGACGCGAGTCCCACACGGATGGAGCTTG
TGAATGGAGTGGTAGACTGTAGATGGTTTTTGTAACGGCTTGAGTAATAACGGA
AGCTTCATGGCTTGAATGACCAGCCATGGTGGTGTGCAAGTGAAGATCGCTGCTT
GTGTGAAGGTTTCCATCTTTCCCATCCCCGTCTTCCACTTTGCTACACGTTGCTAG
TGTCACTTGAACAATTCATTCATGGACCCTGCTCTCCTTTCCCCTGTTACGAAGTT
CTTATGGTAGAGTTCACCGAACGCAAGCTGTCTAGGAAGTTGACAGTTTGTGGGA
GCCAAAAACTCTACTTGAGCTACTGTGTGCACGCCTTCTGAGTCCTCCAGCGAGG
AGCCTGTATATTATTGGATGGTGCAGGATGGGTCGCTTGGTGCCTTTCTCTTTTTC
CTTTTCCTCTTTTTGTAAATGGTTTTCCTTCTATGAATATGTGAAGCTCCTCCCAC
GGAAGCATAGAGCTCGC

Nucleotide sequence of the full-length ZF-2 from
*Physcomitrella patens* (SEQ ID NO: 10)

ATCCCGGGATCAGGAAGCTGTCAAGGAAGAGATGGAAATCTTGCTCCATACAAT
TACTACGGGCCGCCACCGGGCAGTAACAATTATGTCGTCAACAGCAAGATTATG
GTCGTGGCTGTCGCGGTTCTCTTCGCTGTCGTCCTCTTCATCCTCTGCCTCCACAT
CTACGCCAAGTGGTTCTGGCGCAATCAAGGTGCCATCGTCGCAAGCGATGGCAC
CTTGCGTACGTTTATCATGGCGAAGACGCCGTTACACTGTCCCTGTGAACGCTACT
CCGGTGACGCAGGCAGTGGGGCTTGAGCGGGCTGTTATTGAAGCTCTGCCCACTT
TCGAATTCGACGGTGAGAGGGCAAAGCGTGTGTTCGAGTGCGCGGTTTGTTTGG
AAGAATTTGAGTTGGGTGAGAAAGGCCGCACGTTGCCGAAGTGTGACCATAGTT
TCCACTTGGATTGTATTGACATGTGGTTGCACTCGCACTCGACATGCCCGTTGTG
TCGCACGAGTGTGGGAGCTGATGAAACTGAGAAGAAGACCGAGGCCGCCACCGT
GATGCAGATAAGCGAGCCTCCTCAGATGGAAGCGCCCGTTATGGGTGACGTAGG
AGCGCCGTTCATGGCGGCCATGCGAGCTTCCAGGAGGAGCCAACGGAGCCGGGG
ACAGTTGCCGGCGTTGAATAGTTCCCCAAGAGGCAATAGTTTGCCCCGCACTGCG
GAGGATCAGGGCGGGGAGAATCATCGCCGAAGTGGTACGTCGGAAACGGCCGTT
GCGGTTGATCAGCAGCAAAACATAAAAGATTACGAGACACCGTCCGGAATCCCG
TCCAATGTGTTATTCTGGGGGAATCATGCGCAGATGAGCAGTGCAGGTGCAGGA
GGGAGTGCAGAAGCGAGGGCGGCGTCCAGTATTCGTGCGCCGTTTCAGGTTACT
ATCGACATTCCGAGGTCTGGTCCAGCGGCTGTCAGCAATTCGTCGAATGTTTTGT
CGCCGATGGCGCGTGCTTCAGCGAGCTTCCGACGTTTGTTGAGCCGAGGGAAGA
GTGTGGTGTCGCCCCAAACTGGAGAAGATGGTGTTGACGAGGGCGGGCCTTCTT
CTTCACCCCGTCCACCACCACCACATGCCTGAGGATTTCGTGAGCAGGTGCTGTT
AAAGTGGAAATTTTATTCTGGAAGAAAACTGATACTTCCCTGGTAGAACATAAATG
CCCGACCATGCAAAGGATTTTGTGGGATTTGCACCTGATATCAACCAAGCTATCT
AGCGAACGTCACGATTGCGTTGAGTGTTACCCGGCGAAATCCCTAAGCCTACA
TCGCCGATTACGATGCGCACTTTCCTCAGTAAGGTCAACCTTCGCATTGAGGAGG
AAATCGGCGCTTTAGTGCCCACAAAGCATGCCCTTAGATCCCAGATGTGGAATTG
CAATGGGAATTGAGAGCAGGGTACACTGCAAGTGCGTTTTAGGATGTGAAGTGT
GAGCATTGGAGATCTGCGTCTCTGCCGATTAGGTCAGGTCAGCATCACATTTGAC
ACTGGAGATGCAAAATAGTAGCTATTCCTTCTTCACTTCTTCCGATGGTGTACCG
TAGTGTAATATATAGCGCTAGATGTGCAATAAGACGCCACAGTCTGAGGCTCAA
GATGTAATATAGATCATGCACGAAGCAGTTAAGCATCTCTAGGTTAGGAGATTG
AATGCCACAGTGCTTCAGTAACATGTAGAGTTGTAAATAAACGGGAAATCGCCT
TCTGCAAGGCATCTCACTGACACGAACCTAGTGAACATATCAAGGTAATTGCCAT
TTTACGATAACCAGCTTATTGCAAGGCAAGCGCCAGAGCTCGC

Nucleotide sequence of the full-length ZF-3 from
*Physcomitrella patens* (SEQ ID NO: 11)

ATCCCGGGAGGAGGACTTGCGGAATGCAAAATCACAATTTGAGCAGGCTCGATT
CAATTTGATGACAGCACTTACCAATAGTGAGGCAAAAAGAAGTTCGAGTTCCT
TGAAGCCGTGAGTGGTACAATGGATGCACATCTCAGGTACTTCAAGCAGGGCTA
TGAGTTGCTACATCAAATGGAACCTTACATCCATCAGGTGTTAACATATGCTCAA
CAGTCCAGAGAAAGGGCCAACTACGAGCAAGCAGCACTTGCAGATCGTATGCAG
GAGTACAGGCAGGAAGTTGAGAGAGAGAGCCAAAGGTCGATTGATTTTGACAGC
TCTTCTGGAGATGGTATTCAAGGTGTTGGCCGCAGTTCACATAAGATGATTGAGG
CAGTCATGCAATCGACCCCAAAAGGGCAGATCCAGACTCTTAAGCAGGGATACC
TGTTAAAGCGTTCAACAAATTTGCGAGGTGACTGGAAGCGGAGGTTTTTTGTGTT
GGATAGCAGAGGAATGCTGTATTATTATCGGAAACAGTGGGGCAAGCCTACAGA
CGAGAAAAATGTAGCACATCACACTGTGAATCTGCTGACGTCTACAATCAAGAT
AGACGCAGAACAATCAGATCTTCGTTTCTGCTTTCGGATTATTTCTCCAGCTAAA
AGTTATACCCTCCAGGCAGAAAATGCCATTGACAGAATGGATTGGATGGACAAA

APPENDIX-continued

```
ATTACAGGGGTGATTTCGTCGCTTTTAAACAATCAAATATCTGAGCAGGTTGATG
GCGAAGATTCAGATGTATCAAGAAGTGGCGCTAGTGATCAATCTGGGCATGAAA
GACCCCTTGACGTTTTACGCAAGGTGAAAGGAAATGATGCTTGTGCCGACTGCG
GTGCTGCTGATCCCGATTGGGCTTCGCTGAATCTTGGGATTCTTCTGTGTATTGAG
TGCTCAGGAGTACACAGAAACATGAGCGTTCAGATTTCTAAGGTCCGTTCGTTGA
CGTTAGATGTCAAAGTTTGGGAGCCTTCTGTAATGAGCTATTTTCAATCTGTCGG
AAACTCCTACGCTAATTCTATATGGGAAGAGCTTTTGAATCCCAAGTCCTCAGAG
GAGTCAAGTGAGAGAAACGTTAATGACGAGGGACAATCGGGCGTTTTAAGTGCT
AGCAGAGCAAGGCCAAGACCTAGAGACCCCATACCTATCAAAGAAAGATTTATC
AATGCAAAGTATGTGGAGAAAAAATTTGTCCAAAAGTTGAAGGTGGATTCTCGA
GGCCCGTCAGTGACACGGCAGATCTGGGATGCTGTCCAGAACAAAAAAG
TGCAGCTTGCTCTTCGTCTTCTTATCACTGCTGATGCTAACGCCAACACAACCTTC
GAGCAAGTAATGGGTGGTACCGAGTCTTCGTGGTCGTCTCCACTTGCAAGCCTCG
CTGGAGCTCTCTTACGAAAGAACTCTCTCAGTGCCTCTCAGAGTGGTCGCAGGAA
CTGGAGCGTACCTTCACTATTGTCTTCTCCAGACGATCCGGGGTCCCGTTCAGGA
GCTTTAAGCCCTGTTTCGAGAAGTCCTGATGCAGCAGGCAGCGAGGGATTGAT
GAGAAAGATTTGCGGGGCTGCAGTTTGCTCCATGTTGCCTGCCAAATCGGAGAT
ATTAGCCTGATCGAGCTGCTACTTCAATACGGGGCGCAAATCAATTGTGTGGATA
CCCTGGGTCGAACTCCTCTTCATCACTGTGTCTTGTGCGGCAACAATTCGTGTGC
AAAGCTCCTGCTCACAAGAGGGGCGAAGGCGGGTGCCGTAGACAAAGAGGGAA
AAACTCCGCTGGAGTGTGCAGTGGAGAAGCTAGGTGCTATCACGGATGAAGAAT
TGTTCATAATGCTTTCTGAAACCAGTAGATGACACCACATTTGTGCCTGAGTTGC
TTTGTGTATAAATCTCAACATCAACTTGTTTCCTAGCACCTGTAAGGCTAGTTTGT
TTGGGTAGTTTGCATTCTTGTTCTACCGTTTTATCTTCCCATTACGTCAGCATAAG
TAGAGAGTGGAAGCAGGTGGATATCGC
```

Nucleotide sequence of the full-length ZF-4 from
*Physcomitrella patens* (SEQ ID NO: 12)

```
ATCCCGGGCACCAGTCCCGCTTAGTGTGTGTGTCATTAGTGTTGGTTGCAAGTCT
GAAGCCTTGAGCGAGATTTGCAGGATTTTCTCATACGCTTCTGATTAGGAAAGAT
ACACCCTTATTAGTCTGTTAAAGATGGCCACCGAGCGTGTGTCTCAGGAGACGAC
CTCGCAGGCCCTGAGGGTCCAGTTATGTGCAAGAACCTTTGCGGCTTCTTCGGC
AGCCAAGCTACCATGGGGTTGTGCTCGAAGTGCTACCGAGAGACAGTCATGCAA
GCGAAGATGACGGCTTTAGCTGAGCAAGCCACTCAGGCTGCTCAGGCGACATCT
GCCACAGCTGCTGCTGTTCAGCCCCCCGCTCCTGTACATGAGACCAAGCTCACAT
GCGAGGTTGAGAGAACAATGATTGTGCCGCATCAATCTTCCAGCTATCAACAAG
ACCTGGTTACCCCGCTGCAGCTGCCCCTCAGGCAGTGAAGTCCTCTATCGCAGC
TCCCTCTAGACCCGAGCCCAATCGATGCGGATCTTGCAGGAAGCGTGTTGGATTG
ACAGGATTTAAGTGTCGCTGTGGCAACCTCTACTGCGCTTTACATCGGTACTCGG
ACAAACACACTTGCACATATGACTACAAAGCCGCAGGGCAGGAAGCGATTGCGA
AAGCTAATCCTCTTGTCGTGGCCGAGAAGGTTGTCAAGTTTTGATGAGCATCCGT
TAAGCTTTTCTGCCGACGATTTAGGCTTCATACATTGAGTAACTCTACATCTTTCT
TCTTTATCGAGAGAGCGAGTCGCATCAAGAGCTCGCC
```

Nucleotide sequence of the full-length ZF-5 from
*Physcomitrella patens* (SEQ ID NO: 13)

```
ATCCCGGGTATCGATCTGGAGCCCGTTGCAAACTCAATGGTGTATTTTATAGGGC
AAAAGTCTGATCTATATGGAATGCATCCTCTCAGAGTTGCAAATCATGGACTGCA
TGTCACTCTGGGTTATTCTCGATCACCTAGCTTTGCTGGAGTTCAAATTGGTGAGT
ACGAGTATTATGAGTGATCTCGAGTTTATGGTCCCCTTCTTTCATGATCAAGGGT
AATTTATATCAAGGGTGTATATGAGAGATACGCACTTATTGAGTGGACCTTTTCT
CATACTGCATTTACACCCCTGTCAGTTGCAGCATCCTGGTTTGGAATGCCGGGTC
CAGTCCCTCTATTATCCATGAGTGTAAAATCGGAGAGTCTCGATGACATTGGAGG
TCACGAGAAAAAATCTGTAACTGGGTCGGAAGTGGGTGGCCTCGATGCTCAGCT
GTGGCATGCCTGTGCTGGGGGTATGGTTCAACTGCCTCATGTGGGTGCTAAGGTT
GTCTATTTTCCCCAAGGCCATGGCGAACAAGCTGCTTCAACTCCCGAGTTCCCCC
GCACTTTGGTTCCAAATGGAAGTGTTCCCTGCCGAGTTGTGTCAGTTAACTTTCT
GGCTGATACAGAAACAGACGAGGTATTTGCTCGTATTTGCCTGCAGCCTGAGATT
GGCTCCTCCGCTCAGGATTAACAGATGATTCTCTTGCGTCTCCGCCTCTAGAGA
AACCAGCTTCATTTGCCAAAACGCTCACTCAAAGTGATGCAAACAACGGTGGAG
GCTTTTCAATACCTCGTTATTGTGCTGAAACTATTTTCCCACCTCTCGATTACTGT
ATCGATCCTCCTGTTCAAACTGTTCTTGCAAAAGATGTCCATGGAGAGGTGTGGA
AATTTCGTCACAYITACAGGGGGACTCCACGTCGACATTTGTTAACCACAGGATG
GAGCACATTTGTCAATCAAAAGAAGTTAGTTGCGGGTGATGCTATTGTATTTCTT
CGCATCGCATCTGGCGAACTTTGTGTCGGCGTGCGCCGTTCAATGAGGGGTGTCA
GCAACGGAGAATCCTCATCTTGGCACTCCTCAATCAGTAATGCTTCAACGATTCG
GCCATCTCGATGGGAGGTGAAGGGCACAGAAAGTTTCTCGGACTTTTTAGGTGG
CGTTGGTGATAATGGGTACGCACTGAATAGCTCAATTCGGTCTGAAAACCAGGG
CTCTCCAACAACGAGTAGCTTTGCACGGGACCGTGCTCGTGTTACTGCGAAGTCC
GTTCTAGAAGCTGCTGCACTCGCCGTCTCCGGTGAACGTTTTGAGGTTGTGTAT
TATCCTCGTGCTAGCACAGCTGAGTTCTGTGTCAAAGCTGGGCTTGTTAAACGTG
CGCTAGAGCAATCGTGGTACGCTGGAATGCGCTTCAAAATGGCATTTGAAACTG
AAGACTCCTCGAGGATAAGCTGGTTTATGGGAACTATTGCTGCTGTTCAAGCAGC
AGATCCAGTACTTTGGCCTAGTTCTCCATGGCGGGTTCTGCAGGTCACTTGGGAT
GAGCCGGACCTATTGCAGGGAGTGAATCGTGTAAGCCCATGGCAGTTAGAGCTT
GTGGCGACACTTCCTATGCAGCTGCCCCCTGTCTCTCTTCCCAAAAAGAAACTGC
GCACTGTCCAGCCTCAAGAGCTTCCACTTCAGCCCCCTGGACTGCTAAGCCTGCC
```

APPENDIX-continued

```
GTTGGCAGGGACTAGCAACTTTGGTGGGCACTTGGCCACCCCCTGGGGCAGCTCT
GTTCTTTTGGATGACGCCTCTGTTGGCATGCAGGGGGCCAGGCATGATCAATTCA
ACGGGCTTCCAACTGTGGATTTCCGAAATAGTAACTACAAACATCCTCGGGAGTT
TTCTAGGGACAATCAGTACCAGATTCAAGATCATCAAGTCTTCCATCCTAGACCT
GTATTAAATGAGCCCCCTGCGACAAACACTGGCAACTACTTCTCTCTTTTACCTA
GTCTCCAGCGACGGCCAGATATCTCTCCTAGTATTCAGCCCTTAGCCTTCATGTCT
GCTTCTGGAAGCTCACAGCTGGAGACTTCTTCAACTAAGACAGCGGCCACCTCTT
TTTTCCTATTTGGCCAATTCATTGACCCTTCTTGCACCTCCAAACCTCAGCAGCGT
TCCACAGTTATTAATAACGCTTCCGTTGCTGGGGATGGTAAGCATCCTGGCACTA
ATAACTCATCCTCGGATAACAAATCAGAGGACAAGGACAATTGTAGGGATGTTC
AACCCATTCTGAATGGGATTGCTGTAAGATCTGGATTTCGAGCAGATATAGCCGC
GAAGAAGTTTCAACAGAGCGACTCTGCACATCCCACGGAAGCATCACGTGGAAG
CCAAGTTAGCAGCTTACCGTGGTGGCAAACACAGGACGCTCACAAGGATCAGGA
ATTCCATGGAGACAGTCAGACGCCTCATACTCCTGCATCTGGTAGCCAATGAGGC
TAAAGCTTGATCATAGCTCATAACCCTCTCACAGGACGTAATGGGGGTGACAAC
ATGCTAACAGAATTGCACGGTAAAGGAAAACTGTACTAGGCATGTTATATGGGA
ATTCGGATCGCTTCTTGCAATTAAACACGCTAGCGCCGTTTGGTGCCAA
TGTTATTCTGGCATTTGTTTTGTTTCCTTTGGAAACAAATTGCTATATTTCAAAGT
CCTTTGGAGGAGCTCGC
```

Nucleotide sequence of the full-length MYB-1 from
*Physcomitreia patens* (SEQ ID NO: 14)

```
ATCCCGGGCTGTTGTGTACAGTCTGTGGAGAGCTGTAGAAAATTCAATTCCGATT
TCAAAATATCCAGCGACGATGACACGGAACATGGGAGTTTGGAGGACGACATGA
AGGAGTTGAACGAAGCATGGAAATTCCCTTAGGTCGAGATGGCGAGGGTATGC
AGTCAAAGCAGTGCCCGCGCGGCCACTGGCGTCCAGCGGAAGACGACAAGTTGC
GAGAACTAGTGTCCCAGTTTGGACCTCAAAACTGGAATCTCATAGCAGAGAAAC
TTCAGGGTCGATCAGGGAAAAGCTGCAGGCTACGGTGGTTCAATCAGCTGGACC
CTCGCATCAACCGGCACCCATTCTCGGAAGAAGAGGAAGAGCGGCTGCTTATAG
CACACAAGCGCTACGGCAACAAGTGGGCATTGATCGCGCGCCTCTTTCCCGGCC
GCACAGACAACGCGGTGAAGAATCACTGGCACGTTGTGACGGCAAGACAGTCCC
GTGAACGGACACGGAACTTACGGCCGTATCAAAGGTCCGGTACATCGAAGAGGCA
AGGGTAACCGTATCAATACCTCCGCACTTGGAAATTACCATCACGATTCGAAGG
GAGCTCTCACAGCCTGGATTGAGTCGAAGTATGCGACAGTCGAGCAGTCTGCGG
AAGGGCTCGCTAGGTCTCCTTGTACCGGCAGAGGCTCTCCTCCTCTACCCACCGG
TTTCAGTATACCGCAGATTTCCGGCGGCGCCTTCCATCGACCGACAAACATGAGT
ACTAGTCCTCTTAGCGATGTGACTATCGAGTCGCCAAAGTTTAGCAACTCCGAAA
ATGCGCAAATAATAACCGCGCCGTCCTGCAAAAGCCAATGGGAGATCCCAGGT
CAGTATGCTTGCCGAATTCGACTGTTTCCGACAAGCAGCAAGTGCTGCAGAGTA
ATTCCATCGACGGTCAGATCTCCTCCGGGCTCCAGACAAGCGCAATAGTAGCGC
ATGATGAGAAATCGGGCGTCATTTCAATGAATCATCAAGCACCGGATATGTCCT
GTGTTGGATTGAAGTCAAATTTTCAGGGGAGTCTCCATCCTGGCGCTGTTAGATC
TTCTTGGAATCAATCCCTTCCCCACTGTTTTGGCCACAGTAACAAGTTGGTGGAG
GAGTGCAGGAGTTCTACAGGCGCATGCACTGAACGCTCTGAGATTCTGCAAGAA
CAGCATTCTAGCCTTCAGTTTAAATGCAGCACTGCGTACAATACTGGAAGATATC
AACATGAAAACCTTTGTGGGCCAGCATTCTCGCAACAAGACACAGCGAACG
AGGTTGCGAATTTTTCTACGTTGGCATTCTCCGGCCTAGTGAAGCATCGCCAAGA
GAGGTTGTGCAAAGATAGTGGATCTGCTCTCAAGCTGGGACTATCATGGGTTACA
TCCGATAGCACTCTTGACTTGAGTGTTGCCAAAATGTCAGCATCGCAGCCAGAGC
AGTCTGCGCCGGTTGCATTCATTGATTTTCTAGGCGTGGGAGCGGCCTGAAGGCT
GCGGAAAGATTTTAGCAAAGCTTTTATAACGTTTTTTTTGCACAGGGCTGTTTTA
GCTTGTATACCAGTAGGCACTTCTACTTCTTTTTCTTCTTTTCTTTTTCCCCTTTTC
TTCTCCCCCCACTTTCACCATTTCCGCCATAGCAGCCTTTGAATCACGTAATGGA
ACCTTTGGCGGCCTGTATGAGGCACTTTTGGAGGCATCCCTGGACGAAGAATGG
ATCAAACCGTACTGCGGATGTCATGCTTTGAAGCTGCAATCCGAATTCAGTAGCA
TGCTGTGGATGACTCAAAAGGAGTAGCTGCTTTGTGAAACTAATACTATACAGCG
GATTTTGAAGACCCAAGTTTCATGTGGACAAGTCTGAAAAACTTATACGCCACCT
CCATGGGCTTCTACGATGAATATGCGCTTTCGGCTTACACTGCGGCTCTTTTTTGC
ATATATATACTTCCATTCAATTTTATTTGGAAATGTTTTGAATCTACCTTCTCG
TACAAAACTGGGATCAGAAATCTTCCAGGTTGTGGGTCGCAAGTTAACTCTGCA
GATTGTGGCTGACACTTGGGCAATCGGCAACTTTATCTTTTTGTTTTTTACGCTTG
AACGGACCTCAGCTGTACAGACACTCATCATGTACATTCGATGCCATCTCTTGGC
TTTCATGGAAGTTCAGATATCGGAAACTGTGACAGAGACAGAGAGAGAGAGA
GAGAGAGAGAGAGATTCTTGATGCACTGTGCGCCGAGTTTGAGACTAGTTTA
GAAAGATTGATGAAGCTAGCAGTAAATTGTTGGCCTCATCTGAAAGGTACGGCC
TTTACTCCGTGAGCCCGGGAT
```

Nucleotide sequence of the full-length CABF-3 from
*Physcomitrella patens* (SEQ ID NO: 15)

```
ATCCCGGGCAGCGAGCACACAGCTAGCAACTCTTTCGGAGAATACTCCAGGCGA
AATTGGTCGGATGGCCGATAGCTACGGTCACAACGCAGGTTCACCAGAGAGCAG
CCCGCATTCTGATAACGAGTCCGGGGGTCATTACCGAGACCAGGATGCTTCTGTA
CGGGAACAGGATCGGTTCCTGCCCATCGCGAACGTGAGCCGAATCATGAAGAAG
GCGTTGCCGTCTAATGCAAAAATTTCGAAGGACGCGAAAGAGACTGTGCAGGAG
TGTGTGTCCGAGTTCATCAGCTTCATCACTGGTGAGGCGTCAGATAAGTGCCAGA
GGGAGAAGAGAAAGACGATCAACGGTGACGACTTGCTGTGGGCCATGAGTACAC
TTGGTTTCGAAGATTACGTGGAGCCTCTGAAGGTTTACCTACACAAATACCGGGA
```

```
GCTAGAGGGAGAGAAGGCTTCCACGGCCAAGGGTGGTGACCAGCAAGGAGGGA
AAGAAGGGAGTCAAGGTGTTATGGGGTCCATGGGTATGTCGGGCGGAATGAACG
GTATGAACGGTACGATGAACGGGAATATGCATGGACATGGAATCCCGGTGTCGA
TGCAGATGCTGCAGCAGTCGTACGACAGCAGGCACCTCCAGGGATGATGTATT
CCCCTCATCAGATGATGCCGCAATACCAGATGCCAATGCAGTCTGGTGGAAACC
AGCCTCGTGGAGTGTAGGAGGTTCCACGGCGAGGAGAATTTGAAATTGGGGAGA
TTGTCAACCGCGTGAGGGAGTGAGCTCGC
```

Nucleotide sequence of the full-length SFL-1- from
*Physcomitrella patens* (SEQ ID NO: 16)

```
ATCCCGGGCTCGGAAGGACTGTGCATTGTCGAGCGCTGAAGGTGGATGATGCTT
TGGTGACCGAGAGCGGTCTTATCAGTGAAGAAGGAGTTTCTCGTGCTGCAGCTG
AGGAGGCGATGACGTTAGCTTTAGCAGCTGCAAAGGCCGCCATGGAGGCTGCCT
CGTACGCTGATGCGATGCCGTGGAACAGGAGGAGTTTCCGACGGAATTTGATCT
GCTGAGACTAGAGAGGGCCAGGTTGAGCGATGTTGAGCATTCTTTTCGGGTTGA
ATTGGATACAGAGGCTGCCATGATGGAGGCCGAGCAGAGTTATGTGCAGAAGCT
AGAATCGTTGTTGGGAGGTGTTTCCACGCTCGTCCGTGAGGAAGAGGAAACTGC
ATCCGTTTCAGAAGATGAAGATGATTCAAACAGCTTACCTCAAATTCAAGTAGCC
GTTAAATCGAAGCGGAAGGGAGAGAGGAGGAAGAGGCGGGAGCGAGCGTTGGA
AAGGGCAGAGAAGGTTGCCACCGATCTTGCATCAGCACCCCCTCTCCCAAAACC
TAAGAAACCACAGCTTGCGGCGGATCCTTCAGACCCAGTCCGTGCATATTTGCGA
GACATAGGAAGGACGAAGTTGCTAACAGCAAGAGAAGAAGTCGATCTCTCTCAT
CAAATTCAGGATCTTTTGAAGTTGGAGAATATCAAGTCTAACCTTGAGCGAGAG
ATAGGAAGGAATGCCACAATTGGAGAGTGGAGTAGAGCGGTAGGAATGGAACA
GAATGCATTTGAAGCGCGGCTTAAGAAGGGTCGATTCGCCAAGGACAAAATGGT
GAATTCGAATTTGCGGTTGGTTGTCTCGATTGCGAAAAACTACCAGGGCCGAGG
CATGACTCTTCAAGATTTAATTCAGGAAGGGAGCATGGGATTGGTGAGAGGAGC
GGAGAAGTTCGACCCGACCAAGGGGTTTAAGTTCAGCACTTACGCACATTGGTG
GATTAGGCAGGCTGTAACGCGATCAATTGCGGATCAATCTAGGACTTTTCGTTTA
CCTATTCATTTATACGAAGTTATCTCACGTATCAACAAAGCAAAGCGAATGCTGG
TTCAGGAGCATGGGCGGGAAGCACGTAACGAGGAAGTGGCTGAGCTAGTGGGCT
TGACTGTTGAGAAACTGAAATCTGTAGTGAAATCAGCAAAGGCACCAGGTTCGA
TGGAGCGGCCCATTGGCAAAGATGGGGACACTACACTTGGGGAACTTGTCGCAG
ACACAGATGTGGATTCACCTGAGGACGCAATCGTAAAGCAATTGATGCGACAA
GATATAGAGGGCGTTCTACGCACATTGAACCCAAGAGAGAGGGAGGTGCTAAGA
CTGCGTTTTGGATTGGACGATGGGCGGTCCAAGACTTTAGAAGAAATAGGTCAA
ATCTTTAAAGCTACTCGGGAAAGGATAAGACAAATTGAGGCAAAAGCGATGCGC
AAGCTGAGGCAACCCAGCCGGAACAGCATTCTACGAGAGTACTTAGATGTGAAA
TCTGACGCTATTTAATTGCTGCTGATTGATAGTACCTACCAAACCAGGAAAAAGG
CATTTGGTAATGTTTCGATCAGAAAGTAGACTGTTACATAAGTTTCCATTCTTTTA
TGTTTGAATACTACCAGAAGTGGATTTCTTCTGCTGCGAGCTCGC
```

Deduced amino acid sequence of APS-2 from
*Physcomitrella patens* (SEQ ID NO: 17)

```
MRLAAKDTSGRNAFKFRNIDLNKAYSAWDTEEVSASNTGDTTSFRGVRHRPELNKW
VTEIRPTSQKRKIWLGTYETPEEAARAYDVGIFYTKKKIPYNFEDSPQQLQLYPIPPEL
PWESFAALVKQRATSAAKRARVPSSS*
```

Deduced amino acid sequence of ZF-2 from
*Physcomitrella patens* (SEQ ID NO: 18)

```
MVVAVAVLFAVVLFILCLHIYAKWFWRNQGAIVASDGTLRTLSWRRRRYTVPVNAT
PVTQAVGLERAVIEALPTFEFDGERAKRVFECAVCLEEFELGEKGRTLPKCDHSFHLD
CIDMWLHSHSTCPLCRTSVGADETEKKTEAATVMQISEPPQMEAPVMGDVGAPFMA
AMRASRRSQRSRGQLPALNSSPRGNSLPRTAEDQGGENHRRSGTSETAVAVDQQQN
IKDYETPSGIPSNVLFWGNHAQMSSAGAGGSAEARAASSIRAPFQVTIDIPRSGPAAV
SNSSNVLSPMARASASFRRLLSRGKSVVSPQTGEDGVDEGGPSSSPRPPPPHA*
```

Deduced amino acid sequence of ZF-3 from
*Physcomitrella patens* (SEQ ID NO: 19)

```
MTALTNSEAKKKEEFLEAVSGTMDAHLRYFKQGYELLHQMEPYIHQVLTYAQQSRE
RANYEQAALADRMQEYRQEVERESQRSIDFDSSSGDGIQGVGRSSHKMIEAVMQST
PKGQIQTLKQGYLLKRSTNLRGDWKRRFFVLDSRGMLYYYRKQWGKPTDEKNVAH
HTVNLLTSTIKIDAEQSDLRFCFRIISPAKSYTLQAENAIDRMDWMDKITGVISSLLNN
QISEQVDGEDSDVSRSGASDQSGHERPLDVLRKVKGNDACADCGAADPDWASLNL
GILLCIECSGVHRNMSVQISKVRSLTLDVKVWEPSVMSYFQSVGNSYANSIWEELLNP
KSSEESSERNVNDEGQSGVLSASRARPRPRDPIPTKERFINAKYVEKKFVQKLKVDSR
GPSVTRQIWDAVQNKKVQLALRLLITADANANTTFEQVMGGTESSWSSPLASLAGA
LLRKNSLSASQSGRRNWSVPSLLSSPDDPGSRSGALSPVSRSPDAAGSGGIDEKDLRG
CSLLHVACQIGDISLIELLLQYGAQINCVDTLGRTPLHHCVLCGNNSCAKLLLTRGAK
AGAVDKEGKTPLECAVEKLGAITDEELFIMISETSR*
```

APPENDIX-continued

Deduced amino acid sequence of ZF-4 from
*Physcomitrella patens* (SEQ ID NO: 20)

MATERVSQETTSQAPEGPVMCKNLCGFFGSQATMGLCSKCYRETVMQAKMTALAE
QATQAAQATSATAAAVQPPAPVHETKLTCEVERTMIVPHQSSSYQQDLVTPAAAAP
QAVKSSIAAPSRPEPNRCGSCRKRVGLTGFKCRCGNLYCALHRYSDKHTCTYDYKA
AGQEAIAKANPLVVAEKVVKF*

Deduced amino acid sequence of ZF-5 from
*Physcomitrella patens* (SEQ ID NO: 21)

MPGPVPLLSMSVKSESLDDIGGHEKKSVTGSEVGGLDAQLWHACAGGMYQLPHVG
AKVVYFPQGHGEQAASTPEFPRTLVPNGSVPCRVVSVNFLADTETDEVFARICLQPEI
GSSAQDLTDDSLASPPLEKPASFAKTLTQSDANNGGGFSIPRYCAETIFPPLDYCIDPP
VQTVLAKDVHGEVWKFRHIYRGTPRRHLLTTGWSTFVNQKKLVAGDAIVFLRIASG
ELCVGVRRSMRGVSNGESSSWHSSISNASTIRPSRWEVKGTESFSDFLGGVGDNGYA
LNSSIRSENQGSPTTSSFARDRARVTAKSVLEAAALAVSGERFEVVYYPRASTAEFCV
KAGLVKRALEQSWYAGMRFKMAFETEDSSRISWFMGTIAAVQAADPVLWPSSPWR
VLQVTWDEPDLLQGVNRVSPWQLELVATLPMQLPPVSLPKKKLRTVQPQELPLQPP
GLLSLPLAGTSNFGGHLATPWGSSVLLDDASVGMQGARHDQFNGLPTVDFRNSNYK
HPREFSRDNQYQIQDHQVFHPRPVLNEPPATNTGNYFSLLPSLQRRPDISPSIQPLAFM
SASGSSQLETSSTKTAATSFFLFGQFIDPSCTSKYQQRSTVINNASVAGDGKHPGTNNS
SSDNKSEDKDNCRDVQPILNGIAVRSGFRADIAAKKFQQSDSAHPTEASRGSQVSSLP
WWQTQDAHKDQEFHGDSQTPHTPASGSQ*

Deduced amino acid sequence of MYB-1 from
*Physcomitrella patens* (SEQ ID NO: 22)

MKELNEDMEIPLGRDGEGMQSKQCPRGHWRPAEDDKLRELVSQFGPQNWNLIAEK
LQGRSGKSCRLRWFNQLDPRINRHPFSEEEEERLLIAHKRYGNKWALIARLFPGRTDN
AVKNHWHVVTARQSRERTRTYGRIKGPVHRRGKGNRINTSALGNYHHDSKGALTA
WIESKYATVEQSAEGLARSPCTGRGSPPLPTGFSIPQISGGAFHRPTNMSTSPLSDVTIE
SPKFSNSENAQIITAPVLQKPMGDPRSVCLPNSTVSDKQQVLQSNSIDGQISSGLQTSA
IVAHDEKSGVISMNHQAPDMSCVGLKSNFQGSLHPGAVRSSWNQSLPHCFGHSNKL
VEECRSSTGACTERSEILQEQHSSLQFKCSTAYNTGRYQHENLCGPAFSQQDTANEV
ANFSTLAFSGLVKHRQERLCKDSGSALKLGLSWVTSDSTLDLSVAKMSASQPEQSAP
VAFIDFLGVGAA*

Deduced amino acid sequence of CABF-3 from
*Physcomitrella patens* (SEQ ID NO: 23)

MADSYGHNAGSPESSPHSDNESGGHYRDQDASVREQDRFLPIANVSRIMKKALPSN
AKISKDAKETVQECVSEFISFITGEASDKCQREKRKTINGDDLLWAMSTLGFEDYVEP
LKVYLHKYRELEGEKASTAKGGDQQGGKEGSQGVMGSMGMSGGMNGMNGTMNG
NMHGHGIPVSMQMLQQSYGQQAPPGMMYSPHQMMPQYQMPMQSGGNQPRGV

Deduced amino acid sequence of SFL-1 from
*Physcomitrella patens* (SEQ ID NO: 24)

MMEAEQSYVQKLESLLGGVSTLVREEEETASVSEDEDDSNSLPQIQVAVKSKIRKGER
RKRRERALERAEKVATDLASAPPLPKPKKPQLAADPSDPVRAYLRDIGRTKLLTARE
EVDLSHQIQDLLKLENIKSNLEREIGRNATIGEWSRAVGMEQNAFEARLKKGRFAKD
KMVNSNLRLVVSIAKNYQGRGMTLQDLIQEGSMGLVRGAEKYDPTKGFKYSTYAH
WWIRQAVTRSIADQSRTFRLPIHLYEVISRINKAKRMLVQEHGREARNEEVAELVGLT
VEKLKSVVKSAKAPGSMERPIGKDGDTTLGELVADTDVDSPEDAIVKQLMRQDIEG
VLRTLNPREREVLRLRFGLDDGRSKTLEEIGQIFKATRERQIEAKAMRKLRQPSRNS
ILREYLDVKSDAI*

---

The invention claimed is:

1. A transgenic plant cell transformed with an isolated polynucleotide selected from the group consisting of:
   a) a polynucleotide having a sequence comprising nucleotides 1 to 2699 of SEQ ID NO:13; and
   b) a polynucleotide encoding a polypeptide having a sequence comprising amino acids 1 to 714 of SEQ ID NO:21.

2. The plant cell of claim 1, wherein the polynucleotide has the sequence comprising nucleotides 1 to 2699 of SEQ ID NO:13.

3. The plant cell of claim 1, wherein the polynucleotide encodes the polypeptide having the sequence comprising amino acids 1 to 714 of SEQ ID NO:21.

4. A transgenic plant transformed with an isolated polynucleotide selected from the group consisting of:
   a) a polynucleotide having a sequence comprising nucleotides 1 to 2699 of SEQ ID NO:13; and
   b) a polynucleotide encoding a polypeptide having a sequence comprising amino acids 1 to 714 of SEQ ID NO:21.

5. The transgenic plant of claim 4, wherein the polynucleotide has the sequence comprising nucleotides 1 to 2699 of SEQ ID NO:13.

6. The transgenic plant of claim 4, wherein polynucleotide encodes the polypeptide having the sequence comprising amino acids 1 to 714 of SEQ ID NO:21.

7. The transgenic plant of claim 4, further defined as a monocot.

8. The transgenic plant of claim 4, further defined as a dicot.

9. The transgenic plant of claim 4, wherein the plant is selected from the group consisting of maize, wheat, rye, oat, triticale, rice, barley, soybean, peanut, cotton, rapeseed, canola, manihot, pepper, sunflower, tagetes, potato, tobacco, eggplant, tomato, *Vicia* species, pea, alfalfa, coffee, cacao, tea, *Salix* species, oil palm, coconut, perennial grasses, and a forage crop plant.

10. The transgenic plant of claim 9, which is maize.

11. The transgenic plant of claim 9, which is soybean.

12. The transgenic plant of claim 9, which is cotton.

13. The transgenic plant of claim 9, which is rapeseed or canola.

14. A seed which is true breeding for a transgene comprising a polynucleotide selected from the group consisting of:
   a) a polynucleotide having a sequence comprising nucleotides 1 to 2699 of SEQ ID NO:13; and
   b) a polynucleotide encoding a polypeptide having a sequence comprising amino acids 1 to 714 of SEQ ID NO:21.

15. The seed of claim 14, wherein the polynucleotide has the sequence comprising nucleotides 1 to 2699 of SEQ ID NO:13.

16. The seed of claim 14, wherein the polynucleotide encodes the polypeptide having the sequence comprising amino acids 1 to 714 of SEQ ID NO:21.

17. An isolated nucleic acid comprising a polynucleotide selected from the group consisting of:
   a) a polynucleotide having a sequence comprising nucleotides 1 to 2699 of SEQ ID NO:13; and
   b) a polynucleotide encoding a polypeptide having a sequence comprising amino acids 1 to 714 of SEQ ID NO:21.

18. The isolated nucleic acid of claim 17, wherein the polynucleotide has the sequence comprising nucleotides 1 to 2699 of SEQ ID NO:13.

19. The isolated nucleic acid of claim 17, wherein the polynucleotide encodes the polypeptide having the sequence comprising amino acids 1 to 714 of SEQ ID NO:21.

20. A method of producing a drought-tolerant transgenic plant, the method comprising the steps of:
   a) transforming a plant cell with an expression vector comprising a polynucleotide encoding a polypeptide having a sequence comprising amino acids 1 to 714 of SEQ ID NO:21;
   b) growing the transformed plant cell to generate transgenic plants; and
   c) screening the transgenic plants generated in step b) to identify a transgenic plant that expresses the polypeptide and exhibits increased tolerance to drought stress as compared to a wild type variety of the plant.

21. The method of claim 20, wherein the polynucleotide has a sequence comprising nucleotides 1 to 2699 of SEQ ID NO:13.

* * * * *